US008529894B2

(12) United States Patent
Burton et al.

(10) Patent No.: US 8,529,894 B2
(45) Date of Patent: Sep. 10, 2013

(54) METHODS OF REDUCING INFLAMMATION IN CARDIOMYOPATHY

(75) Inventors: Paul B. J. Burton, Thousand Oaks, CA (US); Theresa A. Deisher, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 13/533,727

(22) Filed: Jun. 26, 2012

(65) Prior Publication Data
US 2012/0263729 A1   Oct. 18, 2012

Related U.S. Application Data

(63) Continuation of application No. 10/646,308, filed on Aug. 21, 2003, now abandoned.

(60) Provisional application No. 60/494,457, filed on Aug. 12, 2003, provisional application No. 60/406,418, filed on Feb. 28, 2002.

(51) Int. Cl.
*A61K 39/395* (2006.01)

(52) U.S. Cl.
USPC .............. 424/130.1; 530/387.1; 530/350; 530/351

(58) Field of Classification Search
None
See application file for complete search history.

(56) References Cited

U.S. PATENT DOCUMENTS

| | | | |
|---|---|---|---|
| 5,674,704 A | 10/1997 | Goodwin et al. | |
| 5,928,893 A | 7/1999 | Kang et al. | |
| 6,083,906 A | 7/2000 | Troutt | |
| 6,303,121 B1 | 10/2001 | Kwon | |
| 6,355,779 B1 | 3/2002 | Goodwin et al. | |
| 6,362,325 B1 | 3/2002 | Kwon | |
| 6,458,934 B1 | 10/2002 | Hong et al. | |
| 6,569,997 B1 | 5/2003 | Kwon | |
| 6,627,200 B1 | 9/2003 | Schwarz et al. | |
| 6,793,919 B2 * | 9/2004 | Mohler | 530/388.22 |
| 2003/0082157 A1 | 5/2003 | Kwon | |

FOREIGN PATENT DOCUMENTS

WO   WO 2004/055513   7/2004

OTHER PUBLICATIONS

Aukrust et al. Cytokine Network in Congestive Heart Failure Secondary to Ischemic or Idiopathic Dilated Cardiomyopathy. Am J Cardiol 1999;83:376-382.*
Jovanovic et al. IL-17 Stimulates the Production and Expression of Proinflammatory Cytokines, IL-b and TNF-a, by Human Macrophages. J Immunol 1998; 160:3513-3521.*
Melero I et al., "Monoclonal antibodies against the 4-1BB T-cell activation molecule eradicate established tumors," *Nat Med* Jun. 1997; 3(6):682-685.
Miller, RE et al., "4-1BB-Specific monoclonal antibody promotes the generation of tumor-specific immune responses by direct activation of CD8 T cells in a CD40-dependent manner," *J Immunol* 2002; 169:1792-1800.
Murillo O et al., "Potentiation of therapeutic immune responses against malignancies with monoclonal antibodies," *Clin Cancer Res* Nov. 2003; 9:5454-5464.
Seko Y et al., "Expression of tumour necrosis factor (TNF) ligand superfamily co-stimulatory molecules CD30L, CD27L, OX40L, and 4-1BBL in murine hearts with acute myocarditis caused by Coxsackievirus B3," *J Pathol* 2001; 195:593-603.
Seko Y et al., "Expression of tumor necrosis factor ligand superfamily costimulatory molecules CD27L, CD30L, OX40L and 4-1BBL in the heart of patients with acute myocarditis and dilated cardiomyopathy," *Cardiovasc Pathol* 2002; 11:166-170.
Tirapu I et al., "Improving efficacy of interleukin-12-transfected dendritic cells injected into murine colon cancer with anti-CD137 monoclonal antibodies and alloantigens," *Int J Cancer* 2004; 110:51-60.
Wilcox RA et al., "Provision of antigen and CD137 signaling breaks immunological ignorance, promoting regression of poorly immunogenic tumors," *J Clin Invest* Mar. 2002; 109(5):651-659.
Csiszar A. et al., "Aging-induced proinflammatory shift in cytokine expression profile in coronary arteries," *FASEB J* 17(9):1183-1185, 2003.
Yndestad A. et al., "Increased gene expression of tumor necrosis factor superfamily ligands in peripheral blood mononuclear cells during chronic heart failure," *Cardiovasc Res* 54:175-182, 2002.
Frémeaux-Bacchi et al., "Functional properties of soluble CD21," *Immunopharmacology* 42:31-37, 1999.
Gaudin et al., "Myocarditis Associated with Doxorubicin Cardiotoxicity," *Am J Clin Pathol* 100:158-163, 1993.
Kwon et al., "4-1BB: Still in the Midst of Darkness," *Mol Cells* 10(2):119-126, 2000.
Pullerits, "Cytokine Modulation for Anti-Allergic Treatment," *Current Pharmaceutical Design* 8:1845-1853, 2002.
Saltiel et al., "Doxorubicin (Adriamycin) Cardiomyopathy," *West J Med* 3:332-341, 1983.
Supplementary European Search Report dated May 20, 2010.
Signal et al., "Doxorubicin-induced cardiomyopathy", *N. Engl. J. Med.*, 339(13):900-905, 1998.

* cited by examiner

*Primary Examiner* — Dong Jiang
(74) *Attorney, Agent, or Firm* — James E. Klaniecki

(57) ABSTRACT

The invention pertains to methods of treating cardiovascular disease by modulating inflammatory and immunoregulatory responses associated with such pathological conditions. Embodiments of the invention provide methods for the treatment of cardiovascular disease in a subject having cardiovascular disease comprising administering an effective amount of one or more IL-17 antagonists, IL-18 antagonists, 4-1BB antagonists, CD30 antagonists, OX40 antagonists and/or CD39 alone or in any combination. This abstract is provided for the sole purpose of enabling the reader to quickly ascertain the subject matter of the technical disclosure and is not intended to be used to interpret or limit the scope or meaning of the claims. 37 CFR 1.72(b).

3 Claims, 7 Drawing Sheets

```
                        SEQUENCE LISTING

<160> NUMBER OF SEQ ID NOS: 36

<210> SEQ ID NO 1
<211> LENGTH: 1874
<212> TYPE: DNA
<213> ORGANISM: Homo sapiens
<220> FEATURE:
<221> NAME/KEY: CDS
<222> LOCATION: (54)..(518)

<400> SEQUENCE: 1
gaattccggc aggcacaaac tcatccatcc ccagttgatt ggaagaaaca acg atg       56
                                                          Met
                                                          1 act cct ggg aag acc tca ttg gtg tca ctg cta ctg ctg ctg agc ctg    104
Thr Pro Gly Lys Thr Ser Leu Val Ser Leu Leu Leu Leu Leu Ser Leu
        5                   10                  15 gag gcc ata gtg aag gca gga atc aca atc cca cga aat cca gga tgc    152
Glu Ala Ile Val Lys Ala Gly Ile Thr Ile Pro Arg Asn Pro Gly Cys
    20                  25                  30 cca aat tct gag gac aag aac ttc ccc cgg act gtg atg gtc aac ctg    200
Pro Asn Ser Glu Asp Lys Asn Phe Pro Arg Thr Val Met Val Asn Leu
35                  40                  45 aac atc cat aac cgg aat acc aat acc aat ccc aaa agg tcc tca gat    248
Asn Ile His Asn Arg Asn Thr Asn Thr Asn Pro Lys Arg Ser Ser Asp
50                  55                  60                  65 tac tac aac cga tcc acc tca cct tgg aat ctc cac cgc aat gag gac    296
Tyr Tyr Asn Arg Ser Thr Ser Pro Trp Asn Leu His Arg Asn Glu Asp
                70                  75                  80 cct gag aga tat ccc tct gtg atc tgg gag gca aag tgc cgc cac ttg    344
Pro Glu Arg Tyr Pro Ser Val Ile Trp Glu Ala Lys Cys Arg His Leu
            85                  90                  95 ggc tgc atc aac gct gat ggg aac gtg gac tac cac atg aac tct gtc    392
Gly Cys Ile Asn Ala Asp Gly Asn Val Asp Tyr His Met Asn Ser Val
        100                 105                 110 ccc atc cag caa gag atc ctg gtc ctg cgc agg gag cct cca cac tgc    440
```

```
                Pro Ile Gln Gln Glu Ile Leu Val Leu Arg Arg Glu Pro Pro His Cys
                115                 120                 125 ccc aac tcc ttc cgg ctg gag aag ata ctg gtg tcc gtg ggc tgc acc        488
Pro Asn Ser Phe Arg Leu Glu Lys Ile Leu Val Ser Val Gly Cys Thr
130                 135                 140                 145 tgt gtc acc ccg att gtc cac cat gtg gcc taagagctct ggggagccca          538
Cys Val Thr Pro Ile Val His His Val Ala
                150                 155 cactccccaa agcagttaga ctatggagag ccgacccagc ccctcaggaa ccctcatcct      598
tcaaagacag cctcatttcg gactaaactc attagagttc ttaaggcagt ttgtccaatt      658
aaagcttcag aggtaacact tggccaagat atgagatctg aattacctttt ccctctttcc    718 aagaaggaag gtttgactga gtaccaattt gcttcttgtt tacttttta agggctttaa       778 gttatttatg tatttaatat gccctgagat aactttgggg tataagattc cattttaatg     838
aattacctac tttatttttgt ttgtcttttt aaagaagata agattctggg cttgggaatt    898
ttattattta aaaggtaaaa cctgtattta tttgagctat ttaaggatct atttatgttt     958
aagtatttag aaaaaggtga aaagcacta ttatcagttc tgcctaggta aatgtaagat     1018
agaattaaat ggcagtgcaa aatttctgag tctttacaac atacggatat agtatttcct    1078
cctctttgtt tttaaaagtt ataacatggc tgaaagaaa gattaaacct actttcatat     1138
gtattaattt aaattttgca atttgttgag gttttacaag agatacagca agtctaactc    1198
tctgttccat taaaccctta taataaaatc cttctgtaat aataaagttt caaaagaaaa    1258
tgtttatttg ttctcattaa atgtatttta gcaaactcag ctcttcccta ttgggaagag    1318
ttatgcaaat tctcctataa gcaaaacaaa gcatgtcttt gagtaacaat gacctggaaa    1378
tacccaaaat tccaagttct cgatttcaca tgccttcaag actgaacacc gactaaggtt    1438
ttcatactat tagccaatgc tgtagacaga agcattttga taggaataga gcaaataaga    1498
taatggccct gaggaatggc atgtcattat taaagatcat atggggaaaa tgaaaccctc    1558
cccaaaatac aagaagttct gggaggagac attgtcttca gactacaatg tccagtttct    1618
cccctagact caggcttcct ttggagatta aggcccctca gagatcaaca gaccaacatt    1678
tttctcttcc tcaagcaaca ctcctagggc ctggcttctg tctgatcaag gcaccacaca    1738
acccagaaag gagctgatgg ggcagaatga actttaagta tgagaaaagt tcagcccaag    1798
taaaataaaa actcaatcac attcaattcc agagtagttt caagtttcac atcgtaacca    1858
ttttcgcccg gaattc                                                     1874

<210> SEQ ID NO 2
<211> LENGTH: 155
<212> TYPE: PRT
<213> ORGANISM: Homo sapiens

<400> SEQUENCE: 2

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
                35                  40                  45

Leu Asn Ile His Asn Arg Asn Thr Asn Thr Asn Pro Lys Arg Ser Ser
            50                  55                  60

Asp Tyr Tyr Asn Arg Ser Thr Ser Pro Trp Asn Leu His Arg Asn Glu
65                  70                  75                  80
```

```
Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
130                 135                 140

Thr Cys Val Thr Pro Ile Val His His Val Ala
145                 150                 155

<210> SEQ ID NO 3
<211> LENGTH: 3223
<212> TYPE: DNA
<213> ORGANISM: Homo sapiens
<220> FEATURE:
<221> NAME/KEY: CDS
<222> LOCATION: (93)..(2693)

<400> SEQUENCE: 3
gggagaccgg aattccggga aaagaaagcc tcagaacgtt cgctcgctgc gtccccagcc      60
ggggccgagc cctccgcgac gccacccggg cc atg ggg gcc gca cgc agc ccg      113
                                    Met Gly Ala Ala Arg Ser Pro
                                     1               5 ccg tcc gct gtc ccg ggg ccc ctg ctg ggg ctg ctc ctg ctc ctg           161
Pro Ser Ala Val Pro Gly Pro Leu Leu Gly Leu Leu Leu Leu Leu
         10                  15                  20 ggc gtg ctg gcc ccg ggt ggc gcc tcc ctg cga ctc ctg gac cac cgg       209
Gly Val Leu Ala Pro Gly Gly Ala Ser Leu Arg Leu Leu Asp His Arg
     25                  30                  35 gcg ctg gtc tgc tcc cag ccg ggg cta aac tgc acg gtc aag aat agt      257
Ala Leu Val Cys Ser Gln Pro Gly Leu Asn Cys Thr Val Lys Asn Ser
40                  45                  50                  55 acc tgc ctg gat gac agc tgg att cac cct cga aac ctg acc ccc tcc     305
Thr Cys Leu Asp Asp Ser Trp Ile His Pro Arg Asn Leu Thr Pro Ser
                60                  65                  70 tcc cca aag gac ctg cag atc cag ctg cac ttt gcc cac acc caa caa     353
Ser Pro Lys Asp Leu Gln Ile Gln Leu His Phe Ala His Thr Gln Gln
            75                  80                  85 gga gac ctg ttc ccc gtg gct cac atc gaa tgg aca ctg cag aca gac     401
Gly Asp Leu Phe Pro Val Ala His Ile Glu Trp Thr Leu Gln Thr Asp
        90                  95                 100 gcc agc atc ctg tac ctc gag ggt gca gag tta tct gtc ctg cag ctg     449
Ala Ser Ile Leu Tyr Leu Glu Gly Ala Glu Leu Ser Val Leu Gln Leu
    105                 110                 115 aac acc aat gaa cgt ttg tgc gtc agg ttt gag ttt ctg tcc aaa ctg     497
Asn Thr Asn Glu Arg Leu Cys Val Arg Phe Glu Phe Leu Ser Lys Leu
120                 125                 130                 135 agg cat cac cac agg cgg tgg cgt ttt acc ttc agc cac ttt gtg gtt     545
Arg His His His Arg Arg Trp Arg Phe Thr Phe Ser His Phe Val Val
                140                 145                 150 gac cct gac cag gaa tat gag gtg acc gtt cac cac ctg ccc aag ccc     593
Asp Pro Asp Gln Glu Tyr Glu Val Thr Val His His Leu Pro Lys Pro
            155                 160                 165 atc cct gat ggg gac cca aac cac cag tcc aag aat ttc ctt gtg cct     641
Ile Pro Asp Gly Asp Pro Asn His Gln Ser Lys Asn Phe Leu Val Pro
        170                 175                 180 gac tgt gag cac gcc agg atg aag gta acc acg cca tgc atg agc tca     689
Asp Cys Glu His Ala Arg Met Lys Val Thr Thr Pro Cys Met Ser Ser
    185                 190                 195
```

```
ggc agc ctg tgg gac ccc aac atc acc gtg gag acc ctg gag gcc cac       737
Gly Ser Leu Trp Asp Pro Asn Ile Thr Val Glu Thr Leu Glu Ala His
200                 205                 210                 215 cag ctg cgt gtg agc ttc acc ctg tgg aac gaa tct acc cat tac cag       785
Gln Leu Arg Val Ser Phe Thr Leu Trp Asn Glu Ser Thr His Tyr Gln
                220                 225                 230 atc ctg ctg acc agt ttt ccg cac atg gag aac cac agt tgc ttt gag       833
Ile Leu Leu Thr Ser Phe Pro His Met Glu Asn His Ser Cys Phe Glu
            235                 240                 245 cac atg cac cac ata cct gcg ccc aga cca gaa gag ttc cac cag cga       881
His Met His His Ile Pro Ala Pro Arg Pro Glu Glu Phe His Gln Arg
        250                 255                 260 tcc aac gtc aca ctc act cta cgc aac ctt aaa ggg tgc tgt cgc cac       929
Ser Asn Val Thr Leu Thr Leu Arg Asn Leu Lys Gly Cys Cys Arg His
    265                 270                 275 caa gtg cag atc cag ccc ttc ttc agc agc tgc ctc aat gac tgc ctc       977
Gln Val Gln Ile Gln Pro Phe Phe Ser Ser Cys Leu Asn Asp Cys Leu
280                 285                 290                 295 aga cac tcc gcg act gtt tcc tgc cca gaa atg cca gac act cca gaa      1025
Arg His Ser Ala Thr Val Ser Cys Pro Glu Met Pro Asp Thr Pro Glu
                300                 305                 310 cca att ccg gac tac atg ccc ctg tgg gtg tac tgg ttc atc acg ggc      1073
Pro Ile Pro Asp Tyr Met Pro Leu Trp Val Tyr Trp Phe Ile Thr Gly
            315                 320                 325 atc tcc atc ctg ctg gtg ggc tcc gtc atc ctg ctc atc gtc tgc atg      1121
Ile Ser Ile Leu Leu Val Gly Ser Val Ile Leu Leu Ile Val Cys Met
        330                 335                 340 acc tgg agg cta gct ggg cct gga agt gaa aaa tac agt gat gac acc      1169
Thr Trp Arg Leu Ala Gly Pro Gly Ser Glu Lys Tyr Ser Asp Asp Thr
    345                 350                 355 aaa tac acc gat ggc ctg cct gcg gct gac ctg atc ccc cca ccg ctg      1217
Lys Tyr Thr Asp Gly Leu Pro Ala Ala Asp Leu Ile Pro Pro Pro Leu
360                 365                 370                 375 aag ccc agg aag gtc tgg atc atc tac tca gcc gac cac ccc ctc tac      1265
Lys Pro Arg Lys Val Trp Ile Ile Tyr Ser Ala Asp His Pro Leu Tyr
                380                 385                 390 gtg gac gtg gtc ctg aaa ttc gcc cag ttc ctg ctc acc gcc tgc ggc      1313
Val Asp Val Val Leu Lys Phe Ala Gln Phe Leu Leu Thr Ala Cys Gly
            395                 400                 405 acg gaa gtg gcc ctg gac ctg ctg gaa gag cag gcc atc tcg gag gca      1361
Thr Glu Val Ala Leu Asp Leu Leu Glu Glu Gln Ala Ile Ser Glu Ala
        410                 415                 420 gga gtc atg acc tgg gtg ggc cgt cag aag cag gag atg gtg gag agc      1409
Gly Val Met Thr Trp Val Gly Arg Gln Lys Gln Glu Met Val Glu Ser
    425                 430                 435 aac tct aag atc atc gtc ctg tgc tcc cgc ggc acg cgc gcc aag tgg      1457
Asn Ser Lys Ile Ile Val Leu Cys Ser Arg Gly Thr Arg Ala Lys Trp
440                 445                 450                 455 cag gcg ctc ctg ggc cgg ggc gcg cct gtg cgg ctg cgc tgc gac cac      1505
Gln Ala Leu Leu Gly Arg Gly Ala Pro Val Arg Leu Arg Cys Asp His
                460                 465                 470 gga aag ccc gtg ggg gac ctg ttc act gca gcc atg aac atg atc ctc      1553
Gly Lys Pro Val Gly Asp Leu Phe Thr Ala Ala Met Asn Met Ile Leu
            475                 480                 485 ccg gac ttc aag agg cca gcc tgc ttc ggc acc tac gta gtc tgc tac      1601
Pro Asp Phe Lys Arg Pro Ala Cys Phe Gly Thr Tyr Val Val Cys Tyr
        490                 495                 500 ttc agc gag gtc agc tgt gac ggc gac gtc ccc gac ctg ttc ggc gcg      1649
Phe Ser Glu Val Ser Cys Asp Gly Asp Val Pro Asp Leu Phe Gly Ala
    505                 510                 515
```

| | | |
|---|---|---|
| gcg ccg cgg tac ccg ctc atg gac agg ttc gag gag gtg tac ttc cgc<br>Ala Pro Arg Tyr Pro Leu Met Asp Arg Phe Glu Glu Val Tyr Phe Arg<br>520                          525                          530                        535 | 1697 |
| atc cag gac ctg gag atg ttc cag ccg ggc cgc atg cac cgc gta ggg<br>Ile Gln Asp Leu Glu Met Phe Gln Pro Gly Arg Met His Arg Val Gly<br>540                          545                          550 | 1745 |
| gag ctg tcg ggg gac aac tac ctg cgg agc ccg ggc ggc agg cag ctc<br>Glu Leu Ser Gly Asp Asn Tyr Leu Arg Ser Pro Gly Gly Arg Gln Leu<br>555                          560                          565 | 1793 |
| cgc gcc gcc ctg gac agg ttc cgg gac tgg cag gtc cgc tgt ccc gac<br>Arg Ala Ala Leu Asp Arg Phe Arg Asp Trp Gln Val Arg Cys Pro Asp<br>570                          575                          580 | 1841 |
| tgg ttc gaa tgt gag aac ctc tac tca gca gat gac cag gat gcc ccg<br>Trp Phe Glu Cys Glu Asn Leu Tyr Ser Ala Asp Asp Gln Asp Ala Pro<br>585                          590                          595 | 1889 |
| tcc ctg gac gaa gag gtg ttt gag gag cca ctg ctg cct ccg gga acc<br>Ser Leu Asp Glu Glu Val Phe Glu Glu Pro Leu Leu Pro Pro Gly Thr<br>600                          605                          610                          615 | 1937 |
| ggc atc gtg aag cgg gcg ccc ctg gtg cgc gag cct ggc tcc cag gcc<br>Gly Ile Val Lys Arg Ala Pro Leu Val Arg Glu Pro Gly Ser Gln Ala<br>                          620                          625                          630 | 1985 |
| tgc ctg gcc ata gac ccg ctg gtc ggg gag gaa gga gga gca gca gtg<br>Cys Leu Ala Ile Asp Pro Leu Val Gly Glu Glu Gly Gly Ala Ala Val<br>                          635                          640                          645 | 2033 |
| gca aag ctg gaa cct cac ctg cag ccc cgg ggt cag cca gcg ccg cag<br>Ala Lys Leu Glu Pro His Leu Gln Pro Arg Gly Gln Pro Ala Pro Gln<br>650                          655                          660 | 2081 |
| ccc ctc cac acc ctg gtg ctc gcc gca gag gag ggg gcc ctg gtg gcc<br>Pro Leu His Thr Leu Val Leu Ala Ala Glu Glu Gly Ala Leu Val Ala<br>665                          670                          675 | 2129 |
| gcg gtg gag cct ggg ccc ctg gct gac ggt gcc gca gtc cgg ctg gca<br>Ala Val Glu Pro Gly Pro Leu Ala Asp Gly Ala Ala Val Arg Leu Ala<br>680                          685                          690                          695 | 2177 |
| ctg gcg ggg gag ggc gag gcc tgc ccg ctg ctg ggc agc ccg ggc gct<br>Leu Ala Gly Glu Gly Glu Ala Cys Pro Leu Leu Gly Ser Pro Gly Ala<br>                          700                          705                          710 | 2225 |
| ggg cga aat agc gtc ctc ttc ctc ccc gtg gac ccc gag gac tcg ccc<br>Gly Arg Asn Ser Val Leu Phe Leu Pro Val Asp Pro Glu Asp Ser Pro<br>715                          720                          725 | 2273 |
| ctt ggc agc agc acc ccc atg gcg tct cct gac ctc ctt cca gag gac<br>Leu Gly Ser Ser Thr Pro Met Ala Ser Pro Asp Leu Leu Pro Glu Asp<br>                          730                          735                          740 | 2321 |
| gtg agg gag cac ctc gaa ggc ttg atg ctc tcg ctc ttc gag cag agt<br>Val Arg Glu His Leu Glu Gly Leu Met Leu Ser Leu Phe Glu Gln Ser<br>745                          750                          755 | 2369 |
| ctg agc tgc cag gcc cag ggg ggc tgc agt aga ccc gcc atg gtc ctc<br>Leu Ser Cys Gln Ala Gln Gly Gly Cys Ser Arg Pro Ala Met Val Leu<br>760                          765                          770                          775 | 2417 |
| aca gac cca cac acg ccc tac gag gag gag cag cgg cag tca gtg cag<br>Thr Asp Pro His Thr Pro Tyr Glu Glu Glu Gln Arg Gln Ser Val Gln<br>                          780                          785                          790 | 2465 |
| tct gac cag ggc tac atc tcc agg agc tcc ccg cag ccc ccc gag gga<br>Ser Asp Gln Gly Tyr Ile Ser Arg Ser Ser Pro Gln Pro Pro Glu Gly<br>795                          800                          805 | 2513 |
| ctc acg gaa atg gag gaa gag gaa gag gag cag gac cca ggg aag<br>Leu Thr Glu Met Glu Glu Glu Glu Glu Glu Gln Asp Pro Gly Lys<br>                          810                          815                          820 | 2561 |
| ccg gcc ctg cca ctc tct ccc gag gac ctg gag agc ctg agg agc ctc<br>Pro Ala Leu Pro Leu Ser Pro Glu Asp Leu Glu Ser Leu Arg Ser Leu<br>825                          830                          835 | 2609 |

-continued

```
cag cgg cag ctg ctt ttc cgc cag ctg cag aag aac tcg ggc tgg gac    2657
Gln Arg Gln Leu Leu Phe Arg Gln Leu Gln Lys Asn Ser Gly Trp Asp
840                 845                 850                 855 acg atg ggg tca gag tca gag ggg ccc agt gca tga gggcggctcc         2703
Thr Met Gly Ser Glu Ser Glu Gly Pro Ser Ala
                860                 865 ccagggaccg cccagatccc agctttgaga gaggagtgtg tgtgcacgta ttcatctgtg   2763
tgtacatgtc tgcatgtgta tatgttcgtg tgtgaaatgt aggctttaaa atgtaaatgt   2823 ctggattta atcccaggca tccctcctaa cttttctttg tgcagcggtc tggttatcgt    2883
ctatccccag gggaatccac acagcccgct cccaggagct aatggtagag cgtccttgag   2943
gctccattat tcgttcattc agcatttatt gtgcacctac tatgtggcgg catttggga    3003 taccaagata aattgcatgc ggcatggccc cagccatgaa ggaacttaac cgctagtgcc   3063
gaggacacgt taaacgaaca ggatgggccg ggcacggtgg ctcacgcctg taatcccagc   3123
acactgggag gccgaggcag gtggatcact ctgaggtcag gagtttgagc cagcctggcc   3183
aacatggtga aaccccggaa ttcgagctcg gtacccgggg                        3223
```

<210> SEQ ID NO 4
<211> LENGTH: 866
<212> TYPE: PRT
<213> ORGANISM: Homo sapiens

<400> SEQUENCE: 4

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
        210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
```

-continued

```
                        245                 250                 255
Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
            275                 280                 285

Ser Cys Leu Asn Asp Cys Leu Arg His Ser Ala Thr Val Ser Cys Pro
        290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
                355                 360                 365

Asp Leu Ile Pro Pro Pro Leu Lys Pro Arg Lys Val Trp Ile Ile Tyr
            370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
            565                 570                 575

Trp Gln Val Arg Cys Pro Asp Trp Phe Glu Cys Glu Asn Leu Tyr Ser
        580                 585                 590

Ala Asp Asp Gln Asp Ala Pro Ser Leu Asp Glu Val Phe Glu Glu
            595                 600                 605

Pro Leu Leu Pro Pro Gly Thr Gly Ile Val Lys Arg Ala Pro Leu Val
610                 615                 620

Arg Glu Pro Gly Ser Gln Ala Cys Leu Ala Ile Asp Pro Leu Val Gly
625                 630                 635                 640

Glu Glu Gly Gly Ala Val Ala Lys Leu Glu Pro His Leu Gln Pro
            645                 650                 655

Arg Gly Gln Pro Ala Pro Gln Pro Leu His Thr Leu Val Leu Ala Ala
        660                 665                 670
```

-continued

| | | | | | | | | | | | | |
|---|---|---|---|---|---|---|---|---|---|---|---|---|
|Glu|Glu|Gly|Ala|Leu|Val|Ala|Ala|Val|Glu|Pro|Gly|Pro|Leu|Ala|Asp|
| | |675| | | |680| | | |685| | | | | |

Gly Ala Ala Val Arg Leu Ala Leu Ala Gly Glu Gly Glu Ala Cys Pro
    690             695             700

Leu Leu Gly Ser Pro Gly Ala Gly Arg Asn Ser Val Leu Phe Leu Pro
705             710             715             720

Val Asp Pro Glu Asp Ser Pro Leu Gly Ser Ser Thr Pro Met Ala Ser
                725             730             735

Pro Asp Leu Leu Pro Glu Asp Val Arg Glu His Leu Glu Gly Leu Met
            740             745             750

Leu Ser Leu Phe Glu Gln Ser Leu Ser Cys Gln Ala Gln Gly Gly Cys
        755             760             765

Ser Arg Pro Ala Met Val Leu Thr Asp Pro His Thr Pro Tyr Glu Glu
    770             775             780

Glu Gln Arg Gln Ser Val Gln Ser Asp Gln Gly Tyr Ile Ser Arg Ser
785             790             795             800

Ser Pro Gln Pro Pro Glu Gly Leu Thr Glu Met Glu Glu Glu Glu Glu
                805             810             815

Glu Glu Gln Asp Pro Gly Lys Pro Ala Leu Pro Leu Ser Pro Glu Asp
            820             825             830

Leu Glu Ser Leu Arg Ser Leu Gln Arg Gln Leu Leu Phe Arg Gln Leu
        835             840             845

Gln Lys Asn Ser Gly Trp Asp Thr Met Gly Ser Glu Ser Glu Gly Pro
    850             855             860

Ser Ala
865

<210> SEQ ID NO 5
<211> LENGTH: 1626
<212> TYPE: DNA
<213> ORGANISM: Homo sapeins
<220> FEATURE:
<221> NAME/KEY: CDS
<222> LOCATION: (1)..(1626)

<400> SEQUENCE: 5

| | | | | | | | | | | | | | | | |
|---|---|---|---|---|---|---|---|---|---|---|---|---|---|---|---|---|
|atg|aat|tgt|aga|gaa|tta|ccc|ttg|acc|ctt|tgg|gtg|ctt|ata|tct|gta|48|
|Met|Asn|Cys|Arg|Glu|Leu|Pro|Leu|Thr|Leu|Trp|Val|Leu|Ile|Ser|Val| |
|1| | | |5| | | | |10| | | | |15| | | agc act gca gaa tct tgt act tca cgt ccc cac att act gtg gtt gaa    96
Ser Thr Ala Glu Ser Cys Thr Ser Arg Pro His Ile Thr Val Val Glu
            20                  25                  30 ggg gaa cct ttc tat ctg aaa cat tgc tcg tgt tca ctt gca cat gag    144
Gly Glu Pro Phe Tyr Leu Lys His Cys Ser Cys Ser Leu Ala His Glu
        35                  40                  45 att gaa aca acc acc aaa agc tgg tac aaa agc agt gga tca cag gaa    192
Ile Glu Thr Thr Thr Lys Ser Trp Tyr Lys Ser Ser Gly Ser Gln Glu
    50                  55                  60 cat gtg gag ctg aac cca agg agt tcc tcg aga att gct ttg cat gat    240
His Val Glu Leu Asn Pro Arg Ser Ser Ser Arg Ile Ala Leu His Asp
65                  70                  75                  80 tgt gtt ttg gag ttt tgg cca gtt gag ttg aat gac aca gga tct tac    288
Cys Val Leu Glu Phe Trp Pro Val Glu Leu Asn Asp Thr Gly Ser Tyr
                85                  90                  95 ttt ttc caa atg aaa aat tat act cag aaa tgg aaa tta aat gtc atc    336
Phe Phe Gln Met Lys Asn Tyr Thr Gln Lys Trp Lys Leu Asn Val Ile
            100                 105                 110 aga aga aat aaa cac agc tgt ttc act gaa aga caa gta act agt aaa    384
Arg Arg Asn Lys His Ser Cys Phe Thr Glu Arg Gln Val Thr Ser Lys -continued

```
                 115                 120                 125
att gtg gaa gtt aaa aaa ttt ttt cag ata acc tgt gaa aac agt tac      432
Ile Val Glu Val Lys Lys Phe Phe Gln Ile Thr Cys Glu Asn Ser Tyr
    130                 135                 140 tat caa aca ctg gtc aac agc aca tca ttg tat aag aac tgt aaa aag      480
Tyr Gln Thr Leu Val Asn Ser Thr Ser Leu Tyr Lys Asn Cys Lys Lys
145                 150                 155                 160 cta cta ctg gag aac aat aaa aac cca acg ata aag aag aac gcc gag      528
Leu Leu Leu Glu Asn Asn Lys Asn Pro Thr Ile Lys Lys Asn Ala Glu
                165                 170                 175 ttt gaa gat cag ggg tat tac tcc tgc gtg cat ttc ctt cat cat aat      576
Phe Glu Asp Gln Gly Tyr Tyr Ser Cys Val His Phe Leu His His Asn
            180                 185                 190 gga aaa cta ttt aat atc acc aaa acc ttc aat ata aca ata gtg gaa      624
Gly Lys Leu Phe Asn Ile Thr Lys Thr Phe Asn Ile Thr Ile Val Glu
        195                 200                 205 gat cgc agt aat ata gtt ccg gtt ctt ctt gga cca aag ctt aac cat      672
Asp Arg Ser Asn Ile Val Pro Val Leu Leu Gly Pro Lys Leu Asn His
    210                 215                 220 gtt gca gtg gaa tta gga aaa aac gta agg ctc aac tgc tct gct ttg      720
Val Ala Val Glu Leu Gly Lys Asn Val Arg Leu Asn Cys Ser Ala Leu
225                 230                 235                 240 ctg aat gaa gag gat gta att tat tgg atg ttt ggg gaa gaa aat gga      768
Leu Asn Glu Glu Asp Val Ile Tyr Trp Met Phe Gly Glu Glu Asn Gly
                245                 250                 255 tcg gat cct aat ata cat gaa gag aaa gaa atg aga att atg act cca      816
Ser Asp Pro Asn Ile His Glu Glu Lys Glu Met Arg Ile Met Thr Pro
            260                 265                 270 gaa ggc aaa tgg cat gct tca aaa gta ttg aga att gaa aat att ggt      864
Glu Gly Lys Trp His Ala Ser Lys Val Leu Arg Ile Glu Asn Ile Gly
        275                 280                 285 gaa agc aat cta aat gtt tta tat aat tgc act gtg gcc agc acg gga      912
Glu Ser Asn Leu Asn Val Leu Tyr Asn Cys Thr Val Ala Ser Thr Gly
    290                 295                 300 ggc aca gac acc aaa agc ttc atc ttg gtg aga aaa gca gac atg gct      960
Gly Thr Asp Thr Lys Ser Phe Ile Leu Val Arg Lys Ala Asp Met Ala
305                 310                 315                 320 gat atc cca ggc cac gtc ttc aca aga gga atg atc ata gct gtt ttg     1008
Asp Ile Pro Gly His Val Phe Thr Arg Gly Met Ile Ile Ala Val Leu
                325                 330                 335 atc ttg gtg gca gta gtg tgc cta gtg act gtg tgt gtc att tat aga     1056
Ile Leu Val Ala Val Val Cys Leu Val Thr Val Cys Val Ile Tyr Arg
            340                 345                 350 gtt gac ttg gtt cta ttt tat aga cat tta acg aga aga gat gaa aca     1104
Val Asp Leu Val Leu Phe Tyr Arg His Leu Thr Arg Arg Asp Glu Thr
        355                 360                 365 tta aca gat gga aaa aca tat gat gct ttt gtg tct tac cta aaa gaa     1152
Leu Thr Asp Gly Lys Thr Tyr Asp Ala Phe Val Ser Tyr Leu Lys Glu
    370                 375                 380 tgc cga cct gaa aat gga gag gag cac acc ttt gct gtg gag att ttg     1200
Cys Arg Pro Glu Asn Gly Glu Glu His Thr Phe Ala Val Glu Ile Leu
385                 390                 395                 400 ccc agg gtg ttg gag aaa cat ttt ggg tat aag tta tgc ata ttt gaa     1248
Pro Arg Val Leu Glu Lys His Phe Gly Tyr Lys Leu Cys Ile Phe Glu
                405                 410                 415 agg gat gta gtg cct gga gga gct gtt gtt gat gaa atc cac tca ctg     1296
Arg Asp Val Val Pro Gly Gly Ala Val Val Asp Glu Ile His Ser Leu
            420                 425                 430 ata gag aaa agc cga aga cta atc att gtc cta agt aaa agt tat atg     1344
Ile Glu Lys Ser Arg Arg Leu Ile Ile Val Leu Ser Lys Ser Tyr Met
```

```
                    435                 440                 445
tct aat gag gtc agg tat gaa ctt gaa agt gga ctc cat gaa gca ttg       1392
Ser Asn Glu Val Arg Tyr Glu Leu Glu Ser Gly Leu His Glu Ala Leu
    450                 455                 460 gtg gaa aga aaa att aaa ata atc tta att gaa ttt aca cct gtt act       1440
Val Glu Arg Lys Ile Lys Ile Ile Leu Ile Glu Phe Thr Pro Val Thr
465                 470                 475                 480 gac ttc aca ttc ttg ccc caa tca cta aag ctt ttg aaa tct cac aga       1488
Asp Phe Thr Phe Leu Pro Gln Ser Leu Lys Leu Leu Lys Ser His Arg
                485                 490                 495 gtt ctg aag tgg aag gcc gat aaa tct ctt tct tat aac tca agg ttc       1536
Val Leu Lys Trp Lys Ala Asp Lys Ser Leu Ser Tyr Asn Ser Arg Phe
            500                 505                 510 tgg aag aac ctt ctt tac tta atg cct gca aaa aca gtc aag cca ggt       1584
Trp Lys Asn Leu Leu Tyr Leu Met Pro Ala Lys Thr Val Lys Pro Gly
        515                 520                 525 aga gac gaa ccg gaa gtc ttg cct gtt ctt tcc gag tct taa               1626
Arg Asp Glu Pro Glu Val Leu Pro Val Leu Ser Glu Ser
    530                 535                 540

<210> SEQ ID NO 6
<211> LENGTH: 541
<212> TYPE: PRT
<213> ORGANISM: Homo sapeins

<400> SEQUENCE: 6

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Ser Gly Ser Gln Glu
    50                  55                  60

His Val Glu Leu Asn Pro Arg Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Gly Pro Lys Leu Asn His
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
```

```
                245              250              255
Ser Asp Pro Asn Ile His Glu Glu Lys Glu Met Arg Ile Met Thr Pro
            260              265              270

Glu Gly Lys Trp His Ala Ser Lys Val Leu Arg Ile Glu Asn Ile Gly
        275              280              285

Glu Ser Asn Leu Asn Val Leu Tyr Asn Cys Thr Val Ala Ser Thr Gly
    290              295              300

Gly Thr Asp Thr Lys Ser Phe Ile Leu Val Arg Lys Ala Asp Met Ala
305              310              315              320

Asp Ile Pro Gly His Val Phe Thr Arg Gly Met Ile Ile Ala Val Leu
            325              330              335

Ile Leu Val Ala Val Val Cys Leu Val Thr Val Cys Val Ile Tyr Arg
            340              345              350

Val Asp Leu Val Leu Phe Tyr Arg His Leu Thr Arg Arg Asp Glu Thr
        355              360              365

Leu Thr Asp Gly Lys Thr Tyr Asp Ala Phe Val Ser Tyr Leu Lys Glu
    370              375              380

Cys Arg Pro Glu Asn Gly Glu Glu His Thr Phe Ala Val Glu Ile Leu
385              390              395              400

Pro Arg Val Leu Glu Lys His Phe Gly Tyr Lys Leu Cys Ile Phe Glu
            405              410              415

Arg Asp Val Val Pro Gly Gly Ala Val Val Asp Glu Ile His Ser Leu
            420              425              430

Ile Glu Lys Ser Arg Arg Leu Ile Ile Val Leu Ser Lys Ser Tyr Met
        435              440              445

Ser Asn Glu Val Arg Tyr Glu Leu Glu Ser Gly Leu His Glu Ala Leu
    450              455              460

Val Glu Arg Lys Ile Lys Ile Ile Leu Ile Glu Phe Thr Pro Val Thr
465              470              475              480

Asp Phe Thr Phe Leu Pro Gln Ser Leu Lys Leu Leu Lys Ser His Arg
            485              490              495

Val Leu Lys Trp Lys Ala Asp Lys Ser Leu Ser Tyr Asn Ser Arg Phe
            500              505              510

Trp Lys Asn Leu Leu Tyr Leu Met Pro Ala Lys Thr Val Lys Pro Gly
        515              520              525

Arg Asp Glu Pro Glu Val Leu Pro Val Leu Ser Glu Ser
    530              535              540

<210> SEQ ID NO 7
<211> LENGTH: 2681
<212> TYPE: DNA
<213> ORGANISM: Homo sapiens
<220> FEATURE:
<221> NAME/KEY: CDS
<222> LOCATION: (484)..(2283)

<400> SEQUENCE: 7
ctctctggat aggaagaaat atagtagaac cctttgaaaa tggatatttt cacatatttt     60
cgttcagata caaaagctgg cagttactga aataaggact tgaagttcct tcctcttttt    120
ttatgtctta agagcaggaa ataaagagac agctgaaggt gtagccttga ccaactgaaa    180
gggaaatctt catcctctga aaaacatat gtgattctca aaaacgcat ctggaaaatt     240 gataaagaag cgattctgta gattctccca gcgctgttgg gctctcaatt ccttctgtga    300 aggacaaacat atggtgatgg ggaaatcaga agctttgaga ccctctacac ctggatatga   360 atccccttc taatacttac cagaaatgaa ggggatactc aggcagagt tctgaatctc     420
```

```
aaaacactct actctggcaa aggaatgaag ttattggagt gatgacagga acacgggaga       480 aca atg ctc tgt ttg ggc tgg ata ttt ctt tgg ctt gtt gca gga gag        528
    Met Leu Cys Leu Gly Trp Ile Phe Leu Trp Leu Val Ala Gly Glu
    1               5                   10                  15 cga att aaa gga ttt aat att tca ggt tgt tcc aca aaa aaa ctc ctt        576
Arg Ile Lys Gly Phe Asn Ile Ser Gly Cys Ser Thr Lys Lys Leu Leu
                20                  25                  30 tgg aca tat tct aca agg agt gaa gag gaa ttt gtc tta ttt tgt gat        624
Trp Thr Tyr Ser Thr Arg Ser Glu Glu Glu Phe Val Leu Phe Cys Asp
            35                  40                  45 tta cca gag cca cag aaa tca cat ttc tgc cac aga aat cga ctc tca        672
Leu Pro Glu Pro Gln Lys Ser His Phe Cys His Arg Asn Arg Leu Ser
        50                  55                  60 cca aaa caa gtc cct gag cac ctg ccc ttc atg ggt agt aac gac cta        720
Pro Lys Gln Val Pro Glu His Leu Pro Phe Met Gly Ser Asn Asp Leu
    65                  70                  75 tct gat gtc caa tgg tac caa caa cct tcg aat gga gat cca tta gag        768
Ser Asp Val Gln Trp Tyr Gln Gln Pro Ser Asn Gly Asp Pro Leu Glu
80                  85                  90                  95 gac att agg aaa agc tat cct cac atc att cag gac aaa tgt acc ctt        816
Asp Ile Arg Lys Ser Tyr Pro His Ile Ile Gln Asp Lys Cys Thr Leu
                100                 105                 110 cac ttt ttg acc cca ggg gtg aat aat tct ggg tca tat att tgt aga        864
His Phe Leu Thr Pro Gly Val Asn Asn Ser Gly Ser Tyr Ile Cys Arg
            115                 120                 125 ccc aag atg att aag agc ccc tat gat gta gcc tgt tgt gtc aag atg        912
Pro Lys Met Ile Lys Ser Pro Tyr Asp Val Ala Cys Cys Val Lys Met
        130                 135                 140 att tta gaa gtt aag ccc cag aca aat gca tcc tgt gag tat tcc gca        960
Ile Leu Glu Val Lys Pro Gln Thr Asn Ala Ser Cys Glu Tyr Ser Ala
    145                 150                 155 tca cat aag caa gac cta ctt ctt ggg agc act ggc tct att tct tgc       1008
Ser His Lys Gln Asp Leu Leu Leu Gly Ser Thr Gly Ser Ile Ser Cys
160                 165                 170                 175 ccc agt ctc agc tgc caa agt gat gca caa agt cca gcg gta acc tgg       1056
Pro Ser Leu Ser Cys Gln Ser Asp Ala Gln Ser Pro Ala Val Thr Trp
                180                 185                 190 tac aag aat gga aaa ctc ctc tct gtg gaa agg agc aac cga atc gta       1104
Tyr Lys Asn Gly Lys Leu Leu Ser Val Glu Arg Ser Asn Arg Ile Val
            195                 200                 205 gtg gat gaa gtt tat gac tat cac cag ggc aca tat gta tgt gat tac       1152
Val Asp Glu Val Tyr Asp Tyr His Gln Gly Thr Tyr Val Cys Asp Tyr
        210                 215                 220 act cag tcg gat act gtg agt tcg tgg aca gtc aga gct gtt gtt caa       1200
Thr Gln Ser Asp Thr Val Ser Ser Trp Thr Val Arg Ala Val Val Gln
    225                 230                 235 gtg aga acc att gtg gga gac act aaa ctc aaa cca gat att ctg gat       1248
Val Arg Thr Ile Val Gly Asp Thr Lys Leu Lys Pro Asp Ile Leu Asp
240                 245                 250                 255 cct gtc gag gac aca ctg gaa gta gaa ctt gga aag cct tta act att       1296
Pro Val Glu Asp Thr Leu Glu Val Glu Leu Gly Lys Pro Leu Thr Ile
                260                 265                 270 agc tgc aaa gca cga ttt ggc ttt gaa agg gtc ttt aac cct gtc ata       1344
Ser Cys Lys Ala Arg Phe Gly Phe Glu Arg Val Phe Asn Pro Val Ile
            275                 280                 285 aaa tgg tac atc aaa gat tct gac cta gag tgg gaa gtc tca gta cct       1392
Lys Trp Tyr Ile Lys Asp Ser Asp Leu Glu Trp Glu Val Ser Val Pro
        290                 295                 300 gag gcg aaa agt att aaa tcc act tta aag gat gaa atc att gag cgt       1440
```

```
              Glu Ala Lys Ser Ile Lys Ser Thr Leu Lys Asp Glu Ile Ile Glu Arg
                  305                 310                 315 aat atc atc ttg gaa aaa gtc act cag cgt gat ctt cgc agg aag ttt         1488
Asn Ile Ile Leu Glu Lys Val Thr Gln Arg Asp Leu Arg Arg Lys Phe
320                 325                 330                 335 gtt tgc ttt gtc cag aac tcc att gga aac aca acc cag tcc gtc caa         1536
Val Cys Phe Val Gln Asn Ser Ile Gly Asn Thr Thr Gln Ser Val Gln
                340                 345                 350 ctg aaa gaa aag aga gga gtg gtg ctc ctg tac atc ctg ctt ggc acc         1584
Leu Lys Glu Lys Arg Gly Val Val Leu Leu Tyr Ile Leu Leu Gly Thr
            355                 360                 365 atc ggg acc ctg gtg gcc gtg ctg gcg gcg agt gcc ctc ctc tac agg         1632
Ile Gly Thr Leu Val Ala Val Leu Ala Ala Ser Ala Leu Leu Tyr Arg
        370                 375                 380 cac tgg att gaa ata gtg ctg ctg tac cgg acc tac cag agc aag gat         1680
His Trp Ile Glu Ile Val Leu Leu Tyr Arg Thr Tyr Gln Ser Lys Asp
    385                 390                 395 cag acg ctt ggg gat aaa aag gat ttt gat gct ttc gta tcc tat gca         1728
Gln Thr Leu Gly Asp Lys Lys Asp Phe Asp Ala Phe Val Ser Tyr Ala
400                 405                 410                 415 aaa tgg agc tct ttt cca agt gag gcc act tca tct ctg agt gaa gaa         1776
Lys Trp Ser Ser Phe Pro Ser Glu Ala Thr Ser Ser Leu Ser Glu Glu
                420                 425                 430 cac ttg gcc ctg agc cta ttt cct gat gtt tta gaa aac aaa tat gga         1824
His Leu Ala Leu Ser Leu Phe Pro Asp Val Leu Glu Asn Lys Tyr Gly
                435                 440                 445 tat agc ctg tgt ttg ctt gaa aga gat gtg gct cca gga gga gtg tat         1872
Tyr Ser Leu Cys Leu Leu Glu Arg Asp Val Ala Pro Gly Gly Val Tyr
            450                 455                 460 gca gaa gac att gtg agc att att aag aga agc aga aga gga ata ttt         1920
Ala Glu Asp Ile Val Ser Ile Ile Lys Arg Ser Arg Arg Gly Ile Phe
        465                 470                 475 atc ttg agc ccc aac tat gtc aat gga ccc agt atc ttt gaa cta caa         1968
Ile Leu Ser Pro Asn Tyr Val Asn Gly Pro Ser Ile Phe Glu Leu Gln
    480                 485                 490                 495 gca gca gtg aat ctt gcc ttg gat gat caa aca ctg aaa ctc att tta         2016
Ala Ala Val Asn Leu Ala Leu Asp Asp Gln Thr Leu Lys Leu Ile Leu
                500                 505                 510 att aag ttc tgt tac ttc caa gag cca gag tct cta cct cat ctc gtg         2064
Ile Lys Phe Cys Tyr Phe Gln Glu Pro Glu Ser Leu Pro His Leu Val
                515                 520                 525 aaa aaa gct ctc agg gtt ttg ccc aca gtt act tgg aga ggc tta aaa         2112
Lys Lys Ala Leu Arg Val Leu Pro Thr Val Thr Trp Arg Gly Leu Lys
            530                 535                 540 tca gtt cct ccc aat tct agg ttc tgg gcc aaa atg cgc tac cac atg         2160
Ser Val Pro Pro Asn Ser Arg Phe Trp Ala Lys Met Arg Tyr His Met
545                 550                 555 cct gtg aaa aac tct cag gga ttc acg tgg aac cag ctc aga att acc         2208
Pro Val Lys Asn Ser Gln Gly Phe Thr Trp Asn Gln Leu Arg Ile Thr
560                 565                 570                 575 tct agg att ttt cag tgg aaa gga ctc agt aga aca gaa acc act ggg         2256
Ser Arg Ile Phe Gln Trp Lys Gly Leu Ser Arg Thr Glu Thr Thr Gly
                580                 585                 590 agg agc tcc cag cct aag gaa tgg tga aatgagccct ggagccccct               2303
Arg Ser Ser Gln Pro Lys Glu Trp
                595 ccagtccagt ccctgggata gagatgttgc tggacagaac tcacagctct gtgtgtgtgt      2363 gttcaggctg ataggaaatt caaagagtct cctgccagca ccaagcaagc ttgatgacac       2423 atggaatggg attgagactg tggtttagag cctttgattt cctggactgg acagacggcg      2483
```

```
agtgaattct ctagaccttg ggtactttca gtacacaaca cccctaagat ttcccagtgg   2543
tccgagcaga atcagaaaat acagctactt ctgccttatg gctagggaac tgtcatgtct   2603
accatgtatt gtacatatga ctttatgtat acttgcaatc aaataaatat tattttatta   2663
gaaaaaaaac cggaattc                                                  2681
```

<210> SEQ ID NO 8
<211> LENGTH: 599
<212> TYPE: PRT
<213> ORGANISM: Homo sapiens

<400> SEQUENCE: 8

```
Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335
```

-continued

```
Cys Phe Val Gln Asn Ser Ile Gly Asn Thr Thr Gln Ser Val Gln Leu
            340                 345                 350

Lys Glu Lys Arg Gly Val Val Leu Tyr Ile Leu Leu Gly Thr Ile
355                 360                 365

Gly Thr Leu Val Ala Val Leu Ala Ala Ser Ala Leu Leu Tyr Arg His
370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
            405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
            435                 440                 445

Ser Leu Cys Leu Leu Glu Arg Asp Val Ala Pro Gly Gly Val Tyr Ala
            450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                    485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
            515                 520                 525

Lys Ala Leu Arg Val Leu Pro Thr Val Thr Trp Arg Gly Leu Lys Ser
            530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                    565                 570                 575

Arg Ile Phe Gln Trp Lys Gly Leu Ser Arg Thr Glu Thr Thr Gly Arg
            580                 585                 590

Ser Ser Gln Pro Lys Glu Trp
            595

<210> SEQ ID NO 9
<211> LENGTH: 644
<212> TYPE: DNA
<213> ORGANISM: Homo sapiens
<220> FEATURE:
<221> NAME/KEY: CDS
<222> LOCATION: (66)..(599)

<400> SEQUENCE: 9
gagaagagga cgttgtcaca gataaagagc caggctcacc agctcctgac gcatgcatca        60 tgacc atg aga cac aac tgg aca cca gac ctc agc cct ttg tgg gtc ctg       110
      Met Arg His Asn Trp Thr Pro Asp Leu Ser Pro Leu Trp Val Leu
        1               5                  10                  15 ctc ctg tgt gcc cac gtc gtc act ctc ctg gtc aga gcc aca cct gtc         158
Leu Leu Cys Ala His Val Val Thr Leu Leu Val Arg Ala Thr Pro Val
                 20                  25                  30 tcg cag acc acc aca gct gcc act gcc tca gtt aga agc aca aag gac         206
Ser Gln Thr Thr Thr Ala Ala Thr Ala Ser Val Arg Ser Thr Lys Asp
             35                  40                  45 ccc tgc ccc tcc cag ccc cca gtg ttc cca gca gct aag cag tgt cca         254
Pro Cys Pro Ser Gln Pro Pro Val Phe Pro Ala Ala Lys Gln Cys Pro
        50                  55                  60
```

```
gca ttg gaa gtg acc tgg cca gag gtg gaa gtg cca ctg aat gga acg      302
Ala Leu Glu Val Thr Trp Pro Glu Val Glu Val Pro Leu Asn Gly Thr
65                  70                  75 ctg agc tta tcc tgt gtg gcc tgc agc cgc ttc ccc aac ttc agc atc      350
Leu Ser Leu Ser Cys Val Ala Cys Ser Arg Phe Pro Asn Phe Ser Ile
80                  85                  90                  95 ctc tac tgg ctg ggc aat ggt tcc ttc att gag cac ctc cca ggc cga      398
Leu Tyr Trp Leu Gly Asn Gly Ser Phe Ile Glu His Leu Pro Gly Arg
                100                 105                 110 ctg tgg gag ggg agc acc agc cgg gaa cgt ggg agc aca ggt acg cag      446
Leu Trp Glu Gly Ser Thr Ser Arg Glu Arg Gly Ser Thr Gly Thr Gln
                115                 120                 125 ctg tgc aag gcc ttg gtg ctg gag cag ctg acc cct gcc ctg cac agc      494
Leu Cys Lys Ala Leu Val Leu Glu Gln Leu Thr Pro Ala Leu His Ser
            130                 135                 140 acc aac ttc tcc tgt gtg ctc gtg gac cct gaa cag gtt gtc cag cgt      542
Thr Asn Phe Ser Cys Val Leu Val Asp Pro Glu Gln Val Val Gln Arg
145                 150                 155 cac gtc gtc ctg gcc cag ctc tgg gct ggg ctg agg gca acc ttg ccc      590
His Val Val Leu Ala Gln Leu Trp Ala Gly Leu Arg Ala Thr Leu Pro
160                 165                 170                 175 ccc acc caa gaagccctgc cctccagcca cagcagtcca cagcagcagg gttaa        644
Pro Thr Gln <210> SEQ ID NO 10
<211> LENGTH: 178
<212> TYPE: PRT
<213> ORGANISM: Homo sapiens

<400> SEQUENCE: 10

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
        130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln

<210> SEQ ID NO 11
<211> LENGTH: 422
<212> TYPE: PRT
<213> ORGANISM: Homo sapiens
```

<400> SEQUENCE: 11

```
Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
        35                  40                  45

Cys Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Cys Lys Ala Leu Val Leu Glu Gln Leu Thr Pro Ala Leu His Ser Thr
130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190

Arg Ser Cys Asp Lys Thr His Thr Cys Pro Pro Cys Pro Ala Pro Glu
        195                 200                 205

Ala Glu Gly Ala Pro Ser Val Phe Leu Phe Pro Pro Lys Pro Lys Asp
210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Glu Glu Met Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415
```

```
<210> SEQ ID NO 12
<211> LENGTH: 579
<212> TYPE: DNA
<213> ORGANISM: Homo sapiens
<220> FEATURE:
<221> NAME/KEY: CDS
<222> LOCATION: (1)..(579)
<220> FEATURE:
<221> NAME/KEY: sig_peptide
<222> LOCATION: (1)..(108)
<220> FEATURE:
<221> NAME/KEY: mat_peptide
<222> LOCATION: (109)..()

<400> SEQUENCE: 12
```

| | | | | | | | | | | | | |
|---|---|---|---|---|---|---|---|---|---|---|---|---|
| atg | gct | gct | gaa | cca | gta | gaa | gac | aat | tgc | atc | aac | ttt gtg gca atg | 48 |
| Met | Ala | Ala | Glu | Pro | Val | Glu | Asp | Asn | Cys | Ile | Asn | Phe Val Ala Met |
| -35 | | | | -30 | | | | -25 | | | | | aaa ttt att gac aat acg ctt tac ttt ata gct gaa gat gat gaa aac        96
Lys Phe Ile Asp Asn Thr Leu Tyr Phe Ile Ala Glu Asp Asp Glu Asn
-20                 -15                 -10                  -5 ctg gaa tca gat tac ttt ggc aag ctt gaa tct aaa tta tca gtc ata       144
Leu Glu Ser Asp Tyr Phe Gly Lys Leu Glu Ser Lys Leu Ser Val Ile
             -1  1                   5                  10 aga aat ttg aat gac caa gtt ctc ttc att gac caa gga aat cgg cct       192
Arg Asn Leu Asn Asp Gln Val Leu Phe Ile Asp Gln Gly Asn Arg Pro
         15                  20                  25 cta ttt gaa gat atg act gat tct gac tgt aga gat aat gca ccc cgg       240
Leu Phe Glu Asp Met Thr Asp Ser Asp Cys Arg Asp Asn Ala Pro Arg
     30                  35                  40 acc ata ttt att ata agt atg tat aaa gat agc cag cct aga ggt atg       288
Thr Ile Phe Ile Ile Ser Met Tyr Lys Asp Ser Gln Pro Arg Gly Met
 45                  50                  55                  60 gct gta act atc tct gtg aag tgt gag aaa att tca ayt ctc tcc tgt       336
Ala Val Thr Ile Ser Val Lys Cys Glu Lys Ile Ser Xaa Leu Ser Cys
                 65                  70                  75 gag aac aaa att att tcc ttt aag gaa atg aat cct cct gat aac atc       384
Glu Asn Lys Ile Ile Ser Phe Lys Glu Met Asn Pro Pro Asp Asn Ile
             80                  85                  90 aag gat aca aaa agt gac atc ata ttc ttt cag aga agt gtc cca gga       432
Lys Asp Thr Lys Ser Asp Ile Ile Phe Phe Gln Arg Ser Val Pro Gly
         95                 100                 105 cat gat aat aag atg caa ttt gaa tct tca tca tac gaa gga tac ttt       480
His Asp Asn Lys Met Gln Phe Glu Ser Ser Ser Tyr Glu Gly Tyr Phe
     110                 115                 120 cta gct tgt gaa aaa gag aga gac ctt ttt aaa ctc att ttg aaa aaa       528
Leu Ala Cys Glu Lys Glu Arg Asp Leu Phe Lys Leu Ile Leu Lys Lys
125                 130                 135                 140 gag gat gaa ttg ggg gat aga tct ata atg ttc act gtt caa aac gaa       576
Glu Asp Glu Leu Gly Asp Arg Ser Ile Met Phe Thr Val Gln Asn Glu
                145                 150                 155 gac                                                                    579
Asp

```
<210> SEQ ID NO 13
<211> LENGTH: 193
<212> TYPE: PRT
<213> ORGANISM: Homo sapiens
<220> FEATURE:
<221> NAME/KEY: misc_feature
<222> LOCATION: (73)..(73)
<223> OTHER INFORMATION: The 'Xaa' at location 73 stands for Thr, or
```

```
                Ile.

<400> SEQUENCE: 13

Met Ala Ala Glu Pro Val Glu Asp Asn Cys Ile Asn Phe Val Ala Met
    -35                 -30                 -25
Lys Phe Ile Asp Asn Thr Leu Tyr Phe Ile Ala Glu Asp Glu Asn
-20                 -15                 -10                  -5
Leu Glu Ser Asp Tyr Phe Gly Lys Leu Glu Ser Lys Leu Ser Val Ile
             -1  1               5                  10
Arg Asn Leu Asn Asp Gln Val Leu Phe Ile Asp Gln Gly Asn Arg Pro
            15                  20                  25
Leu Phe Glu Asp Met Thr Asp Ser Asp Cys Arg Asp Asn Ala Pro Arg
        30                  35                  40
Thr Ile Phe Ile Ile Ser Met Tyr Lys Asp Ser Gln Pro Arg Gly Met
45                  50                  55                  60
Ala Val Thr Ile Ser Val Lys Cys Glu Lys Ile Ser Xaa Leu Ser Cys
                65                  70                  75
Glu Asn Lys Ile Ile Ser Phe Lys Glu Met Asn Pro Pro Asp Asn Ile
                80                  85                  90
Lys Asp Thr Lys Ser Asp Ile Ile Phe Phe Gln Arg Ser Val Pro Gly
            95                  100                 105
His Asp Asn Lys Met Gln Phe Glu Ser Ser Tyr Glu Gly Tyr Phe
    110                 115                 120
Leu Ala Cys Glu Lys Glu Arg Asp Leu Phe Lys Leu Ile Leu Lys Lys
125                 130                 135                 140
Glu Asp Glu Leu Gly Asp Arg Ser Ile Met Phe Thr Val Gln Asn Glu
                145                 150                 155
Asp

<210> SEQ ID NO 14
<211> LENGTH: 157
<212> TYPE: PRT
<213> ORGANISM: Homo sapiens

<400> SEQUENCE: 14

Tyr Phe Gly Lys Leu Glu Ser Lys Leu Ser Val Ile Arg Asn Leu Asn
1               5                   10                  15
Asp Gln Val Leu Phe Ile Asp Gln Gly Asn Arg Pro Leu Phe Glu Asp
            20                  25                  30
Met Thr Asp Ser Asp Cys Arg Asp Asn Ala Pro Arg Thr Ile Phe Ile
        35                  40                  45
Ile Ser Met Tyr Lys Asp Ser Gln Pro Arg Gly Met Ala Val Thr Ile
50                  55                  60
Ser Val Lys Cys Glu Lys Ile Ser Thr Leu Ser Cys Glu Asn Lys Ile
65                  70                  75                  80
Ile Ser Phe Lys Glu Met Asn Pro Pro Asp Asn Ile Lys Asp Thr Lys
                85                  90                  95
Ser Asp Ile Ile Phe Phe Gln Arg Ser Val Pro Gly His Asp Asn Lys
            100                 105                 110
Met Gln Phe Glu Ser Ser Tyr Glu Gly Tyr Phe Leu Ala Cys Glu
        115                 120                 125
Lys Glu Arg Asp Leu Phe Lys Leu Ile Leu Lys Lys Glu Asp Glu Leu
    130                 135                 140
Gly Asp Arg Ser Ile Met Phe Thr Val Gln Asn Glu Asp
145                 150                 155
```

<210> SEQ ID NO 15
<211> LENGTH: 765
<212> TYPE: DNA
<213> ORGANISM: Homo sapiens
<220> FEATURE:
<221> NAME/KEY: CDS
<222> LOCATION: (4)..(765)

<400> SEQUENCE: 15

```
gtc atg gaa tac gcc tct gac gct tca ctg gac ccc gaa gcc ccg tgg      48
    Met Glu Tyr Ala Ser Asp Ala Ser Leu Asp Pro Glu Ala Pro Trp
    1               5                   10                  15 cct ccc gcg ccc cgc gct cgc gcc tgc cgc gta ctg cct tgg gcc ctg      96
Pro Pro Ala Pro Arg Ala Arg Ala Cys Arg Val Leu Pro Trp Ala Leu
                20                  25                  30 gtc gcg ggg ctg ctg ctg ctg ctg ctc gct gcc gcc tgc gcc gtc         144
Val Ala Gly Leu Leu Leu Leu Leu Leu Ala Ala Ala Cys Ala Val
                35                  40                  45 ttc ctc gcc tgc ccc tgg gcc gtg tcc ggg gct cgc gcc tcg ccc ggc     192
Phe Leu Ala Cys Pro Trp Ala Val Ser Gly Ala Arg Ala Ser Pro Gly
            50                  55                  60 tcc gcg gcc agc ccg aga ctc cgc gag ggt ccc gag ctt tcg ccc gac     240
Ser Ala Ala Ser Pro Arg Leu Arg Glu Gly Pro Glu Leu Ser Pro Asp
65                  70                  75 gat ccc gcc ggc ctc ttg gac ctg cgg cag ggc atg ttt gcg cag ctg     288
Asp Pro Ala Gly Leu Leu Asp Leu Arg Gln Gly Met Phe Ala Gln Leu
80                  85                  90                  95 gtg gcc caa aat gtt ctg ctg atc gat ggg ccc ctg agc tgg tac agt     336
Val Ala Gln Asn Val Leu Leu Ile Asp Gly Pro Leu Ser Trp Tyr Ser
                100                 105                 110 gac cca ggc ctg gca ggc gtg tcc ctg acg ggg ggc ctg agc tac aaa     384
Asp Pro Gly Leu Ala Gly Val Ser Leu Thr Gly Gly Leu Ser Tyr Lys
            115                 120                 125 gag gac acg aag gag ctg gtg gtg gcc aag gct gga gtc tac tat gtc     432
Glu Asp Thr Lys Glu Leu Val Val Ala Lys Ala Gly Val Tyr Tyr Val
        130                 135                 140 ttc ttt caa cta gag ctg cgg cgc gtg gtg gcc ggc gag ggc tca ggc     480
Phe Phe Gln Leu Glu Leu Arg Arg Val Val Ala Gly Glu Gly Ser Gly
145                 150                 155 tcc gtt tca ctt gcg ctg cac ctg cag cca ctg cgc tct gct gct ggg     528
Ser Val Ser Leu Ala Leu His Leu Gln Pro Leu Arg Ser Ala Ala Gly
160                 165                 170                 175 gcc gcc gcc ctg gct ttg acc gtg gac ctg cca ccc gcc tcc tcc gag     576
Ala Ala Ala Leu Ala Leu Thr Val Asp Leu Pro Pro Ala Ser Ser Glu
                180                 185                 190 gct cgg aac tcg gcc ttc ggt ttc cag ggc cgc ttg ctg cac ctg agt     624
Ala Arg Asn Ser Ala Phe Gly Phe Gln Gly Arg Leu Leu His Leu Ser
            195                 200                 205 gcc ggc cag cgc ctg ggc gtc cat ctt cac act gag gcc agg gca cgc     672
Ala Gly Gln Arg Leu Gly Val His Leu His Thr Glu Ala Arg Ala Arg
        210                 215                 220 cat gcc tgg cag ctt acc cag ggc gcc aca gtc ttg gga ctc ttc cgg     720
His Ala Trp Gln Leu Thr Gln Gly Ala Thr Val Leu Gly Leu Phe Arg
225                 230                 235 gtg acc ccc gaa atc cca gcc gga ctc cct tca ccg agg tcg gaa         765
Val Thr Pro Glu Ile Pro Ala Gly Leu Pro Ser Pro Arg Ser Glu
240                 245                 250
```

<210> SEQ ID NO 16
<211> LENGTH: 254
<212> TYPE: PRT
<213> ORGANISM: Homo sapiens

```
<400> SEQUENCE: 16

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
            245                 250

<210> SEQ ID NO 17
<211> LENGTH: 1415
<212> TYPE: DNA
<213> ORGANISM: Homo sapiens
<220> FEATURE:
<221> NAME/KEY: CDS
<222> LOCATION: (120)..(884)
<220> FEATURE:
<221> NAME/KEY: sig_peptide
<222> LOCATION: (120)..(189)
<220> FEATURE:
<221> NAME/KEY: mat_peptide
<222> LOCATION: (189)..()

<400> SEQUENCE: 17
agtggaaagt tctccggcag ccctgagatc tcaagagtga catttgtgag accagctaat      60
ttgattaaaa ttctcttgga atcagctttg ctagtatcat acctgtgcca gatttcatc     119 atg gga aac agc tgt tac aac ata gta gcc act ctg ttg ctg gtc ctc     167
Met Gly Asn Ser Cys Tyr Asn Ile Val Ala Thr Leu Leu Leu Val Leu
            -20                 -15                 -10 aac ttt gag agg aca aga tca ttg cag gat cct tgt agt aac tgc cca     215
Asn Phe Glu Arg Thr Arg Ser Leu Gln Asp Pro Cys Ser Asn Cys Pro
        -5                  -1  1                   5
```

```
gct ggt aca ttc tgt gat aat aac agg aat cag att tgc agt ccc tgt    263
Ala Gly Thr Phe Cys Asp Asn Asn Arg Asn Gln Ile Cys Ser Pro Cys
10              15                  20                  25 cct cca aat agt ttc tcc agc gca ggt gga caa agg acc tgt gac ata    311
Pro Pro Asn Ser Phe Ser Ser Ala Gly Gly Gln Arg Thr Cys Asp Ile
            30                  35                  40 tgc agg cag tgt aaa ggt gtt ttc agg acc agg aag gag tgt tcc tcc    359
Cys Arg Gln Cys Lys Gly Val Phe Arg Thr Arg Lys Glu Cys Ser Ser
        45                  50                  55 acc agc aat gca gag tgt gac tgc act cca ggg ttt cac tgc ctg ggg    407
Thr Ser Asn Ala Glu Cys Asp Cys Thr Pro Gly Phe His Cys Leu Gly
    60                  65                  70 gca gga tgc agc atg tgt gaa cag gat tgt aaa caa ggt caa gaa ctg    455
Ala Gly Cys Ser Met Cys Glu Gln Asp Cys Lys Gln Gly Gln Glu Leu
75                  80                  85 aca aaa aaa ggt tgt aaa gac tgt tgc ttt ggg aca ttt aac gat cag    503
Thr Lys Lys Gly Cys Lys Asp Cys Cys Phe Gly Thr Phe Asn Asp Gln
90              95                  100                 105 aaa cgt ggc atc tgt cga ccc tgg aca aac tgt tct ttg gat gga aag    551
Lys Arg Gly Ile Cys Arg Pro Trp Thr Asn Cys Ser Leu Asp Gly Lys
            110                 115                 120 tct gtg ctt gtg aat ggg acg aag gag agg gac gtg gtc tgt gga cca    599
Ser Val Leu Val Asn Gly Thr Lys Glu Arg Asp Val Val Cys Gly Pro
        125                 130                 135 tct cca gcc gac ctc tct ccg gga gca tcc tct gtg acc ccg cct gcc    647
Ser Pro Ala Asp Leu Ser Pro Gly Ala Ser Ser Val Thr Pro Pro Ala
    140                 145                 150 cct gcg aga gag cca gga cac tct ccg cag atc atc tcc ttc ttt ctt    695
Pro Ala Arg Glu Pro Gly His Ser Pro Gln Ile Ile Ser Phe Phe Leu
155                 160                 165 gcg ctg acg tcg act gcg ttg ctc ttc ctg ctc ttc ctc acg ctc         743
Ala Leu Thr Ser Thr Ala Leu Leu Phe Leu Leu Phe Phe Leu Thr Leu
170             175                 180                 185 cgt ttc tct gtt gtt aaa cgg ggc aga aag aaa ctc ctg tat ata ttc    791
Arg Phe Ser Val Val Lys Arg Gly Arg Lys Lys Leu Leu Tyr Ile Phe
            190                 195                 200 aaa caa cca ttt atg aga cca gta caa act act caa gag gaa gat ggc    839
Lys Gln Pro Phe Met Arg Pro Val Gln Thr Thr Gln Glu Glu Asp Gly
        205                 210                 215 tgt agc tgc cga ttt cca gaa gaa gaa gaa gga gga tgt gaa ctg        884
Cys Ser Cys Arg Phe Pro Glu Glu Glu Glu Gly Gly Cys Glu Leu
    220                 225                 230 tgaaatggaa gtcaataggg ctgttgggac tttcttgaaa agaagcaagg aaatatgagt   944
catccgctat cacagctttc aaaagcaaga acaccatcct acataatacc caggattccc  1004
ccaacacacg ttcttttcta aatgccaatg agttggcctt taaaaatgca ccactttttt  1064
tttttttttt gacagggtct cactctgtca cccaggctgg agtgcagtgg caccaccatg  1124
gctctctgca gccttgacct ctgggagctc aagtgatcct cctgcctcag tctcctagta  1184
gctggaacta caaggaaggg ccaccacacc tgactaactt ttttgttttt tgtttggtaa  1244
agatggcatt tcgccatgtt gtacaggctg gtctcaaact cctaggttca ctttggcctc  1304
ccaaagtgct gggattacag acatgaactg ccaggcccgg ccaaaataat gcaccacttt  1364
taacagaaca gacagatgag gacagagctg gtgataaaaa aaaaaaaaaa a           1415
```

<210> SEQ ID NO 18
<211> LENGTH: 255
<212> TYPE: PRT
<213> ORGANISM: Homo sapiens

<400> SEQUENCE: 18

```
Met Gly Asn Ser Cys Tyr Asn Ile Val Ala Thr Leu Leu Val Leu
            -20                 -15                 -10

Asn Phe Glu Arg Thr Arg Ser Leu Gln Asp Pro Cys Ser Asn Cys Pro
         -5                  -1  1                   5

Ala Gly Thr Phe Cys Asp Asn Asn Arg Asn Gln Ile Cys Ser Pro Cys
 10              15                  20                  25

Pro Pro Asn Ser Phe Ser Ser Ala Gly Gly Gln Arg Thr Cys Asp Ile
             30                  35                  40

Cys Arg Gln Cys Lys Gly Val Phe Arg Thr Arg Lys Glu Cys Ser Ser
         45                  50                  55

Thr Ser Asn Ala Glu Cys Asp Cys Thr Pro Gly Phe His Cys Leu Gly
             60                  65                  70

Ala Gly Cys Ser Met Cys Glu Gln Asp Cys Lys Gln Gly Gln Glu Leu
 75                  80                  85

Thr Lys Lys Gly Cys Lys Asp Cys Cys Phe Gly Thr Phe Asn Asp Gln
 90                  95                 100                 105

Lys Arg Gly Ile Cys Arg Pro Trp Thr Asn Cys Ser Leu Asp Gly Lys
             110                 115                 120

Ser Val Leu Val Asn Gly Thr Lys Glu Arg Asp Val Val Cys Gly Pro
         125                 130                 135

Ser Pro Ala Asp Leu Ser Pro Gly Ala Ser Ser Val Thr Pro Pro Ala
             140                 145                 150

Pro Ala Arg Glu Pro Gly His Ser Pro Gln Ile Ile Ser Phe Phe Leu
         155                 160                 165

Ala Leu Thr Ser Thr Ala Leu Leu Phe Leu Leu Phe Phe Leu Thr Leu
170                 175                 180                 185

Arg Phe Ser Val Val Lys Arg Gly Arg Lys Lys Leu Leu Tyr Ile Phe
             190                 195                 200

Lys Gln Pro Phe Met Arg Pro Val Gln Thr Thr Gln Glu Glu Asp Gly
         205                 210                 215

Cys Ser Cys Arg Phe Pro Glu Glu Glu Glu Gly Gly Cys Glu Leu
             220                 225                 230
```

<210> SEQ ID NO 19
<211> LENGTH: 648
<212> TYPE: DNA
<213> ORGANISM: Homo sapiens
<220> FEATURE:
<221> NAME/KEY: CDS
<222> LOCATION: (1)..(645)

<400> SEQUENCE: 19

```
atg cat gtg ccg gcg ggc tcc gtg gcc agc cac ctg ggg acc acg agc        48
Met His Val Pro Ala Gly Ser Val Ala Ser His Leu Gly Thr Thr Ser
 1               5                  10                  15 cgc agc tat ttc tat ttg acc aca gcc act ctg gct ctg tgc ctt gtc        96
Arg Ser Tyr Phe Tyr Leu Thr Thr Ala Thr Leu Ala Leu Cys Leu Val
             20                  25                  30 ttc acg gtg gcc act att atg gtg ttg gtc gtt cag agg acg gac tcc       144
Phe Thr Val Ala Thr Ile Met Val Leu Val Val Gln Arg Thr Asp Ser
         35                  40                  45 att ccc aac tca cct gac aac gtc ccc ctc aaa gga gga aat tgc tca       192
Ile Pro Asn Ser Pro Asp Asn Val Pro Leu Lys Gly Gly Asn Cys Ser
     50                  55                  60 gaa gac ctc tta tgt atc ctg aaa aga gct cca ttc aag aag tca tgg       240
Glu Asp Leu Leu Cys Ile Leu Lys Arg Ala Pro Phe Lys Lys Ser Trp
 65                  70                  75                  80
```

```
gcc tac ctc caa gtg gca aag cat cta aac aaa acc aag ttg tct tgg       288
Ala Tyr Leu Gln Val Ala Lys His Leu Asn Lys Thr Lys Leu Ser Trp
            85                  90                  95 aac aaa gat ggc att ctc cat gga gtc aga tat cag gat ggg aat ctg       336
Asn Lys Asp Gly Ile Leu His Gly Val Arg Tyr Gln Asp Gly Asn Leu
        100                 105                 110 gtg atc caa ttc cct ggt ttg tac ttc atc att tgc caa ctg cag ttt       384
Val Ile Gln Phe Pro Gly Leu Tyr Phe Ile Ile Cys Gln Leu Gln Phe
        115                 120                 125 ctt gta caa tgc cca aat aat tct gtc gat ctg aag ttg gag ctt ctc       432
Leu Val Gln Cys Pro Asn Asn Ser Val Asp Leu Lys Leu Glu Leu Leu
        130                 135                 140 atc aac aag cat atc aaa aaa cag gcc ctg gtg aca gtg tgt gag tct       480
Ile Asn Lys His Ile Lys Lys Gln Ala Leu Val Thr Val Cys Glu Ser
145                 150                 155                 160 gga atg caa acg aaa cac gta tac cag aat ctc tct caa ttc ttg ctg       528
Gly Met Gln Thr Lys His Val Tyr Gln Asn Leu Ser Gln Phe Leu Leu
                165                 170                 175 gat tac ctg cag gtc aac acc acc ata tca gtc aat gtg gat aca ttc       576
Asp Tyr Leu Gln Val Asn Thr Thr Ile Ser Val Asn Val Asp Thr Phe
        180                 185                 190 cag tac ata gat aca agc acc ttt cct ctt gag aat gtg ttg tcc atc       624
Gln Tyr Ile Asp Thr Ser Thr Phe Pro Leu Glu Asn Val Leu Ser Ile
        195                 200                 205 ttc tta tac agt aat tca gac tga                                       648
Phe Leu Tyr Ser Asn Ser Asp
    210                 215

<210> SEQ ID NO 20
<211> LENGTH: 215
<212> TYPE: PRT
<213> ORGANISM: Homo sapiens

<400> SEQUENCE: 20

Met His Val Pro Ala Gly Ser Val Ala Ser His Leu Gly Thr Thr Ser
1               5                   10                  15

Arg Ser Tyr Phe Tyr Leu Thr Thr Ala Thr Leu Ala Leu Cys Leu Val
            20                  25                  30

Phe Thr Val Ala Thr Ile Met Val Leu Val Val Gln Arg Thr Asp Ser
        35                  40                  45

Ile Pro Asn Ser Pro Asp Asn Val Pro Leu Lys Gly Gly Asn Cys Ser
    50                  55                  60

Glu Asp Leu Leu Cys Ile Leu Lys Arg Ala Pro Phe Lys Lys Ser Trp
65                  70                  75                  80

Ala Tyr Leu Gln Val Ala Lys His Leu Asn Lys Thr Lys Leu Ser Trp
            85                  90                  95

Asn Lys Asp Gly Ile Leu His Gly Val Arg Tyr Gln Asp Gly Asn Leu
        100                 105                 110

Val Ile Gln Phe Pro Gly Leu Tyr Phe Ile Ile Cys Gln Leu Gln Phe
        115                 120                 125

Leu Val Gln Cys Pro Asn Asn Ser Val Asp Leu Lys Leu Glu Leu Leu
        130                 135                 140

Ile Asn Lys His Ile Lys Lys Gln Ala Leu Val Thr Val Cys Glu Ser
145                 150                 155                 160

Gly Met Gln Thr Lys His Val Tyr Gln Asn Leu Ser Gln Phe Leu Leu
                165                 170                 175

Asp Tyr Leu Gln Val Asn Thr Thr Ile Ser Val Asn Val Asp Thr Phe
        180                 185                 190
```

```
Gln Tyr Ile Asp Thr Ser Thr Phe Pro Leu Glu Asn Val Leu Ser Ile
        195                 200                 205

Phe Leu Tyr Ser Asn Ser Asp
    210                 215

<210> SEQ ID NO 21
<211> LENGTH: 705
<212> TYPE: DNA
<213> ORGANISM: Homo sapiens
<220> FEATURE:
<221> NAME/KEY: CDS
<222> LOCATION: (1)..(702)

<400> SEQUENCE: 21 atg gac cca ggg ctg cag caa gca ctc aac gga atg gcc cct cct gga        48
Met Asp Pro Gly Leu Gln Gln Ala Leu Asn Gly Met Ala Pro Pro Gly
1               5                   10                  15 gac aca gcc atg cat gtg ccg gcg ggc tcc gtg gcc agc cac ctg ggg        96
Asp Thr Ala Met His Val Pro Ala Gly Ser Val Ala Ser His Leu Gly
            20                  25                  30 acc acg agc cgc agc tat ttc tat ttg acc aca gcc act ctg gct ctg       144
Thr Thr Ser Arg Ser Tyr Phe Tyr Leu Thr Thr Ala Thr Leu Ala Leu
        35                  40                  45 tgc ctt gtc ttc acg gtg gcc act att atg gtg ttg gtc gtt cag agg       192
Cys Leu Val Phe Thr Val Ala Thr Ile Met Val Leu Val Val Gln Arg
    50                  55                  60 acg gac tcc att ccc aac tca cct gac aac gtc ccc ctc aaa gga gga       240
Thr Asp Ser Ile Pro Asn Ser Pro Asp Asn Val Pro Leu Lys Gly Gly
65                  70                  75                  80 aat tgc tca gaa gac ctc tta tgt atc ctg aaa aga gct cca ttc aag       288
Asn Cys Ser Glu Asp Leu Leu Cys Ile Leu Lys Arg Ala Pro Phe Lys
                85                  90                  95 aag tca tgg gcc tac ctc caa gtg gca aag cat cta aac aaa acc aag       336
Lys Ser Trp Ala Tyr Leu Gln Val Ala Lys His Leu Asn Lys Thr Lys
            100                 105                 110 ttg tct tgg aac aaa gat ggc att ctc cat gga gtc aga tat cag gat       384
Leu Ser Trp Asn Lys Asp Gly Ile Leu His Gly Val Arg Tyr Gln Asp
        115                 120                 125 ggg aat ctg gtg atc caa ttc cct ggt ttg tac ttc atc att tgc caa       432
Gly Asn Leu Val Ile Gln Phe Pro Gly Leu Tyr Phe Ile Ile Cys Gln
    130                 135                 140 ctg cag ttt ctt gta caa tgc cca aat aat tct gtc gat ctg aag ttg       480
Leu Gln Phe Leu Val Gln Cys Pro Asn Asn Ser Val Asp Leu Lys Leu
145                 150                 155                 160 gag ctt ctc atc aac aag cat atc aaa aaa cag gcc ctg gtg aca gtg       528
Glu Leu Leu Ile Asn Lys His Ile Lys Lys Gln Ala Leu Val Thr Val
                165                 170                 175 tgt gag tct gga atg caa acg aaa cac gta tac cag aat ctc tct caa       576
Cys Glu Ser Gly Met Gln Thr Lys His Val Tyr Gln Asn Leu Ser Gln
            180                 185                 190 ttc ttg ctg gat tac ctg cag gtc aac acc acc ata tca gtc aat gtg       624
Phe Leu Leu Asp Tyr Leu Gln Val Asn Thr Thr Ile Ser Val Asn Val
        195                 200                 205 gat aca ttc cag tac ata gat aca agc acc ttt cct ctt gag aat gtg       672
Asp Thr Phe Gln Tyr Ile Asp Thr Ser Thr Phe Pro Leu Glu Asn Val
    210                 215                 220 ttg tcc atc ttc tta tac agt aat tca gac tga                           705
Leu Ser Ile Phe Leu Tyr Ser Asn Ser Asp
225                 230

<210> SEQ ID NO 22
```

<211> LENGTH: 234
<212> TYPE: PRT
<213> ORGANISM: Homo sapiens

<400> SEQUENCE: 22

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 23
<211> LENGTH: 1788
<212> TYPE: DNA
<213> ORGANISM: Homo sapiens
<220> FEATURE:
<221> NAME/KEY: CDS
<222> LOCATION: (1)..(1785)

<400> SEQUENCE: 23 atg cgc gtc ctc ctc gcc gcg ctg gga ctg ctg ttc ctg ggg gcg cta      48
Met Arg Val Leu Leu Ala Ala Leu Gly Leu Leu Phe Leu Gly Ala Leu
1               5                   10                  15 cga gcc ttc cca cag gat cga ccc ttc gag gac acc tgt cat gga aac      96
Arg Ala Phe Pro Gln Asp Arg Pro Phe Glu Asp Thr Cys His Gly Asn
            20                  25                  30 ccc agc cac tac tat gac aag gct gtc agg agg tgc tgt tac cgc tgc     144
Pro Ser His Tyr Tyr Asp Lys Ala Val Arg Arg Cys Cys Tyr Arg Cys
        35                  40                  45 ccc atg ggg ctg ttc ccg aca cag cag tgc cca cag agg cct act gac     192
Pro Met Gly Leu Phe Pro Thr Gln Gln Cys Pro Gln Arg Pro Thr Asp
    50                  55                  60 tgc agg aag cag tgt gag cct gac tac tac ctg gat gag gcc gac cgc     240
Cys Arg Lys Gln Cys Glu Pro Asp Tyr Tyr Leu Asp Glu Ala Asp Arg

```
                          65                  70                  75                  80
tgt aca gcc tgc gtg act tgt tct cga gat gac ctc gtg gag aag acg     288
Cys Thr Ala Cys Val Thr Cys Ser Arg Asp Asp Leu Val Glu Lys Thr
                    85                  90                  95 ccg tgt gca tgg aac tcc tcc cgt gtc tgc gaa tgt cga ccc ggc atg     336
Pro Cys Ala Trp Asn Ser Ser Arg Val Cys Glu Cys Arg Pro Gly Met
                100                 105                 110 ttc tgt tcc acg tct gcc gtc aac tcc tgt gcc cgc tgc ttc ttc cat     384
Phe Cys Ser Thr Ser Ala Val Asn Ser Cys Ala Arg Cys Phe Phe His
            115                 120                 125 tct gtc tgt ccg gca ggg atg att gtc aag ttc cca ggc acg gcg cag     432
Ser Val Cys Pro Ala Gly Met Ile Val Lys Phe Pro Gly Thr Ala Gln
        130                 135                 140 aag aac acg gtc tgt gag ccg gct tcc cca ggg gtc agc cct gcc tgt     480
Lys Asn Thr Val Cys Glu Pro Ala Ser Pro Gly Val Ser Pro Ala Cys
145                 150                 155                 160 gcc agc cca gag aac tgc aag gaa ccc tcc agt ggc acc atc ccc cag     528
Ala Ser Pro Glu Asn Cys Lys Glu Pro Ser Ser Gly Thr Ile Pro Gln
                165                 170                 175 gcc aag ccc acc ccg gtg tcc cca gca acc tcc agt gcc agc acc atg     576
Ala Lys Pro Thr Pro Val Ser Pro Ala Thr Ser Ser Ala Ser Thr Met
                180                 185                 190 cct gta aga ggg ggc acc cgc ctc gcc cag gaa gct gct tct aaa ctg     624
Pro Val Arg Gly Gly Thr Arg Leu Ala Gln Glu Ala Ala Ser Lys Leu
            195                 200                 205 acg agg gct ccc gac tct ccc tcc tct gtg gga agg cct agt tca gat     672
Thr Arg Ala Pro Asp Ser Pro Ser Ser Val Gly Arg Pro Ser Ser Asp
        210                 215                 220 cca ggt ctg tcc cca aca cag cca tgc cca gag ggg tct ggt gat tgc     720
Pro Gly Leu Ser Pro Thr Gln Pro Cys Pro Glu Gly Ser Gly Asp Cys
225                 230                 235                 240 aga aag cag tgt gag ccc gac tac tac ctg gac gag gcc ggc cgc tgc     768
Arg Lys Gln Cys Glu Pro Asp Tyr Tyr Leu Asp Glu Ala Gly Arg Cys
                245                 250                 255 aca gcc tgc gtg agc tgt tct cga gat gac ctt gtg gag aag acg cca     816
Thr Ala Cys Val Ser Cys Ser Arg Asp Asp Leu Val Glu Lys Thr Pro
                260                 265                 270 tgt gca tgg aac tcc tcc cgc acc tgc gaa tgt cga cct ggc atg atc     864
Cys Ala Trp Asn Ser Ser Arg Thr Cys Glu Cys Arg Pro Gly Met Ile
            275                 280                 285 tgt gcc aca tca gcc acc aac tcc tgt gcc cgc tgt gtc ccc tac cca     912
Cys Ala Thr Ser Ala Thr Asn Ser Cys Ala Arg Cys Val Pro Tyr Pro
        290                 295                 300 atc tgt gca gga gag acg gtc acc aag ccc cag gat atg gct gag aag     960
Ile Cys Ala Gly Glu Thr Val Thr Lys Pro Gln Asp Met Ala Glu Lys
305                 310                 315                 320 gac acc acc ttt gag gcg cca ccc ctg ggg acc cag ccg gac tgc aac     1008
Asp Thr Thr Phe Glu Ala Pro Pro Leu Gly Thr Gln Pro Asp Cys Asn
                325                 330                 335 ccc acc cca gag aat ggc gag gcg cct gcc agc acc agc ccc act cag     1056
Pro Thr Pro Glu Asn Gly Glu Ala Pro Ala Ser Thr Ser Pro Thr Gln
                340                 345                 350 agc ttg ctg gtg gac tcc cag gcc agt aag acg ctg ccc atc cca acc     1104
Ser Leu Leu Val Asp Ser Gln Ala Ser Lys Thr Leu Pro Ile Pro Thr
            355                 360                 365 agc gct ccc gtc gct ctc tcc tcc acg ggg aag ccc gtt ctg gat gca     1152
Ser Ala Pro Val Ala Leu Ser Ser Thr Gly Lys Pro Val Leu Asp Ala
        370                 375                 380 ggg cca gtg ctc ttc tgg gtg atc ctg gtg ttg gtt gtg gtg gtc ggc     1200
Gly Pro Val Leu Phe Trp Val Ile Leu Val Leu Val Val Val Val Gly
```

```
                385                 390                 395                 400
tcc agc gcc ttc ctc ctg tgc cac cgg agg gcc tgc agg aag cga att      1248
Ser Ser Ala Phe Leu Leu Cys His Arg Arg Ala Cys Arg Lys Arg Ile
                    405                 410                 415 cgg cag aag ctc cac ctg tgc tac ccg gtc cag acc tcc cag ccc aag      1296
Arg Gln Lys Leu His Leu Cys Tyr Pro Val Gln Thr Ser Gln Pro Lys
                420                 425                 430 cta gag ctt gtg gat tcc aga ccc agg agc tca acg cag ctg agg          1344
Leu Glu Leu Val Asp Ser Arg Pro Arg Ser Ser Thr Gln Leu Arg
            435                 440                 445 agt ggt gcg tcg gtg aca gaa ccc gtc gcg gaa gag cga ggg tta atg      1392
Ser Gly Ala Ser Val Thr Glu Pro Val Ala Glu Glu Arg Gly Leu Met
        450                 455                 460 agc cag cca ctg atg gag acc tgc cac agc gtg ggg gca gcc tac ctg      1440
Ser Gln Pro Leu Met Glu Thr Cys His Ser Val Gly Ala Ala Tyr Leu
465                 470                 475                 480 gag agc ctg ccg ctg cag gat gcc agc ccg gcc ggg ggc ccc tcg tcc      1488
Glu Ser Leu Pro Leu Gln Asp Ala Ser Pro Ala Gly Gly Pro Ser Ser
                485                 490                 495 ccc agg gac ctt cct gag ccc cgg gtg tcc acg gag cac acc aat aac      1536
Pro Arg Asp Leu Pro Glu Pro Arg Val Ser Thr Glu His Thr Asn Asn
                500                 505                 510 aag att gag aaa atc tac atc atg aag gct gac acc gtg atc gtg ggg      1584
Lys Ile Glu Lys Ile Tyr Ile Met Lys Ala Asp Thr Val Ile Val Gly
            515                 520                 525 acc gtg aag gct gag ctg ccg gag ggc cgg ggc ctg gcg ggg cca gca      1632
Thr Val Lys Ala Glu Leu Pro Glu Gly Arg Gly Leu Ala Gly Pro Ala
        530                 535                 540 gag ccc gag ttg gag gag gag ctg gag gcg gac cat acc ccc cac tac      1680
Glu Pro Glu Leu Glu Glu Glu Leu Glu Ala Asp His Thr Pro His Tyr
545                 550                 555                 560 ccc gag cag gag aca gaa ccg cct ctg ggc agc tgc agc gat gtc atg      1728
Pro Glu Gln Glu Thr Glu Pro Pro Leu Gly Ser Cys Ser Asp Val Met
                565                 570                 575 ctc tca gtg gaa gag gaa ggg aaa gaa gac ccc ttg ccc aca gct gcc      1776
Leu Ser Val Glu Glu Glu Gly Lys Glu Asp Pro Leu Pro Thr Ala Ala
                580                 585                 590 tct gga aag tga                                                      1788
Ser Gly Lys
        595

<210> SEQ ID NO 24
<211> LENGTH: 595
<212> TYPE: PRT
<213> ORGANISM: Homo sapiens

<400> SEQUENCE: 24

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95
```

-continued

```
Pro Cys Ala Trp Asn Ser Ser Arg Val Cys Glu Cys Arg Pro Gly Met
                100                 105                 110
Phe Cys Ser Thr Ser Ala Val Asn Ser Cys Ala Arg Cys Phe Phe His
            115                 120                 125
Ser Val Cys Pro Ala Gly Met Ile Val Lys Phe Pro Gly Thr Ala Gln
130                 135                 140
Lys Asn Thr Val Cys Glu Pro Ala Ser Pro Gly Val Ser Pro Ala Cys
145                 150                 155                 160
Ala Ser Pro Glu Asn Cys Lys Glu Pro Ser Ser Gly Thr Ile Pro Gln
                165                 170                 175
Ala Lys Pro Thr Pro Val Ser Pro Ala Thr Ser Ser Ala Ser Thr Met
            180                 185                 190
Pro Val Arg Gly Gly Thr Arg Leu Ala Gln Glu Ala Ala Ser Lys Leu
        195                 200                 205
Thr Arg Ala Pro Asp Ser Pro Ser Ser Val Gly Arg Pro Ser Ser Asp
210                 215                 220
Pro Gly Leu Ser Pro Thr Gln Pro Cys Pro Glu Gly Ser Gly Asp Cys
225                 230                 235                 240
Arg Lys Gln Cys Glu Pro Asp Tyr Tyr Leu Asp Glu Ala Gly Arg Cys
                245                 250                 255
Thr Ala Cys Val Ser Cys Ser Arg Asp Asp Leu Val Glu Lys Thr Pro
            260                 265                 270
Cys Ala Trp Asn Ser Ser Arg Thr Cys Glu Cys Arg Pro Gly Met Ile
        275                 280                 285
Cys Ala Thr Ser Ala Thr Asn Ser Cys Ala Arg Cys Val Pro Tyr Pro
290                 295                 300
Ile Cys Ala Gly Glu Thr Val Thr Lys Pro Gln Asp Met Ala Glu Lys
305                 310                 315                 320
Asp Thr Thr Phe Glu Ala Pro Pro Leu Gly Thr Gln Pro Asp Cys Asn
                325                 330                 335
Pro Thr Pro Glu Asn Gly Glu Ala Pro Ala Ser Thr Ser Pro Thr Gln
            340                 345                 350
Ser Leu Leu Val Asp Ser Gln Ala Ser Lys Thr Leu Pro Ile Pro Thr
        355                 360                 365
Ser Ala Pro Val Ala Leu Ser Ser Thr Gly Lys Pro Val Leu Asp Ala
370                 375                 380
Gly Pro Val Leu Phe Trp Val Ile Leu Val Leu Val Val Val Val Gly
385                 390                 395                 400
Ser Ser Ala Phe Leu Leu Cys His Arg Arg Ala Cys Arg Lys Arg Ile
                405                 410                 415
Arg Gln Lys Leu His Leu Cys Tyr Pro Val Gln Thr Ser Gln Pro Lys
            420                 425                 430
Leu Glu Leu Val Asp Ser Arg Pro Arg Arg Ser Ser Thr Gln Leu Arg
        435                 440                 445
Ser Gly Ala Ser Val Thr Glu Pro Val Ala Glu Glu Arg Gly Leu Met
450                 455                 460
Ser Gln Pro Leu Met Glu Thr Cys His Ser Val Gly Ala Ala Tyr Leu
465                 470                 475                 480
Glu Ser Leu Pro Leu Gln Asp Ala Ser Pro Ala Gly Gly Pro Ser Ser
                485                 490                 495
Pro Arg Asp Leu Pro Glu Pro Arg Val Ser Thr Glu His Thr Asn Asn
            500                 505                 510
Lys Ile Glu Lys Ile Tyr Ile Met Lys Ala Asp Thr Val Ile Val Gly
        515                 520                 525
```

```
Thr Val Lys Ala Glu Leu Pro Glu Gly Arg Gly Leu Ala Gly Pro Ala
        530             535                 540
Glu Pro Glu Leu Glu Glu Leu Glu Ala Asp His Thr Pro His Tyr
545             550                 555                 560
Pro Glu Gln Glu Thr Glu Pro Pro Leu Gly Ser Cys Ser Asp Val Met
                565                 570                 575
Leu Ser Val Glu Glu Gly Lys Glu Asp Pro Leu Pro Thr Ala Ala
            580                 585                 590
Ser Gly Lys
        595

<210> SEQ ID NO 25
<211> LENGTH: 696
<212> TYPE: DNA
<213> ORGANISM: Homo sapiens
<220> FEATURE:
<221> NAME/KEY: CDS
<222> LOCATION: (138)..(686)

<400> SEQUENCE: 25
ggccctggga cctttgccta ttttctgatt gataggcttt gttttgtctt tacctccttc        60
tttctgggga aaacttcagt tttatcgcac gttccccttt tccatatctt catcttccct       120
ctacccagat tgtgaag atg gaa agg gtc caa ccc ctg gaa gag aat gtg          170
                Met Glu Arg Val Gln Pro Leu Glu Glu Asn Val
                  1               5                  10 gga aat gca gcc agg cca aga ttc gag agg aac aag cta ttg ctg gtg         218
Gly Asn Ala Ala Arg Pro Arg Phe Glu Arg Asn Lys Leu Leu Leu Val
             15                  20                  25 gcc tct gta att cag gga ctg ggg ctg ctc ctg tgc ttc acc tac atc         266
Ala Ser Val Ile Gln Gly Leu Gly Leu Leu Leu Cys Phe Thr Tyr Ile
         30                  35                  40 tgc ctg cac ttc tct gct ctt cag gta tca cat cgg tat cct cga att         314
Cys Leu His Phe Ser Ala Leu Gln Val Ser His Arg Tyr Pro Arg Ile
     45                  50                  55 caa agt atc aaa gta caa ttt acc gaa tat aag aag gag aaa ggt ttc         362
Gln Ser Ile Lys Val Gln Phe Thr Glu Tyr Lys Lys Glu Lys Gly Phe
 60                  65                  70                  75 atc ctc act tcc caa aag gag gat gaa atc atg aag gtg cag aac aac         410
Ile Leu Thr Ser Gln Lys Glu Asp Glu Ile Met Lys Val Gln Asn Asn
                 80                  85                  90 tca gtc atc atc aac tgt gat ggg ttt tat ctc atc tcc ctg aag ggc         458
Ser Val Ile Ile Asn Cys Asp Gly Phe Tyr Leu Ile Ser Leu Lys Gly
             95                 100                 105 tac ttc tcc cag gaa gtc aac att agc ctt cat tac cag aag gat gag         506
Tyr Phe Ser Gln Glu Val Asn Ile Ser Leu His Tyr Gln Lys Asp Glu
        110                 115                 120 gag ccc ctc ttc caa ctg aag aag gtc agg tct gtc aac tcc ttg atg         554
Glu Pro Leu Phe Gln Leu Lys Lys Val Arg Ser Val Asn Ser Leu Met
    125                 130                 135 gtg gcc tct ctg act tac aaa gac aaa gtc tac ttg aat gtg acc act         602
Val Ala Ser Leu Thr Tyr Lys Asp Lys Val Tyr Leu Asn Val Thr Thr
140                 145                 150                 155 gac aat acc tcc ctg gat gac ttc cat gtg aat ggc gga gaa ctg att         650
Asp Asn Thr Ser Leu Asp Asp Phe His Val Asn Gly Gly Glu Leu Ile
                160                 165                 170 ctt atc cat caa aat cct ggt gaa ttc tgt gtc ctt tgaggggctg              696
Leu Ile His Gln Asn Pro Gly Glu Phe Cys Val Leu
            175                 180
```

```
<210> SEQ ID NO 26
<211> LENGTH: 183
<212> TYPE: PRT
<213> ORGANISM: Homo sapiens

<400> SEQUENCE: 26

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 27
<211> LENGTH: 865
<212> TYPE: DNA
<213> ORGANISM: Homo sapiens
<220> FEATURE:
<221> NAME/KEY: CDS
<222> LOCATION: (15)..(845)

<400> SEQUENCE: 27
cagcagagac gagg atg tgc gtg ggg gct cgg cgg ctg ggc cgc ggg ccg        50
             Met Cys Val Gly Ala Arg Arg Leu Gly Arg Gly Pro
             1               5                   10 tgt gcg gct ctg ctc ctc ctg ggc ctg ggg ctg agc acc gtg acg ggg        98
Cys Ala Ala Leu Leu Leu Leu Gly Leu Gly Leu Ser Thr Val Thr Gly
            15                  20                  25 ctc cac tgt gtc ggg gac acc tac ccc agc aac gac cgg tgc tgc cac       146
Leu His Cys Val Gly Asp Thr Tyr Pro Ser Asn Asp Arg Cys Cys His
        30                  35                  40 gag tgc agg cca ggc aac ggg atg gtg agc cgc tgc agc cgc tcc cag       194
Glu Cys Arg Pro Gly Asn Gly Met Val Ser Arg Cys Ser Arg Ser Gln
45                  50                  55                  60 aac acg gtg tgc cgt ccg tgc ggg ccg ggc ttc tac aac gac gtg gtc       242
Asn Thr Val Cys Arg Pro Cys Gly Pro Gly Phe Tyr Asn Asp Val Val
                65                  70                  75 agc tcc aag ccg tgc aag ccc tgc acg tgg tgt aac ctc aga agt ggg       290
Ser Ser Lys Pro Cys Lys Pro Cys Thr Trp Cys Asn Leu Arg Ser Gly
            80                  85                  90 agt gag cgg aag cag ctg tgc acg gcc aca cag gac aca gtc tgc cgc       338
Ser Glu Arg Lys Gln Leu Cys Thr Ala Thr Gln Asp Thr Val Cys Arg
```

```
tgc cgg gcg ggc acc cag ccc ctg gac agc tac aag cct gga gtt gac      386
Cys Arg Ala Gly Thr Gln Pro Leu Asp Ser Tyr Lys Pro Gly Val Asp
    110                 115                 120 tgt gcc ccc tgc cct cca ggg cac ttc tcc cca ggc gac aac cag gcc      434
Cys Ala Pro Cys Pro Pro Gly His Phe Ser Pro Gly Asp Asn Gln Ala
125                 130                 135                 140 tgc aag ccc tgg acc aac tgc acc ttg gct ggg aag cac acc ctg cag      482
Cys Lys Pro Trp Thr Asn Cys Thr Leu Ala Gly Lys His Thr Leu Gln
                145                 150                 155 ccg gcc agc aat agc tcg gac gca atc tgt gag gac agg gac ccc cca      530
Pro Ala Ser Asn Ser Ser Asp Ala Ile Cys Glu Asp Arg Asp Pro Pro
            160                 165                 170 gcc acg cag ccc cag gag acc cag ggc ccc cgg gcc agg ccc atc act      578
Ala Thr Gln Pro Gln Glu Thr Gln Gly Pro Pro Ala Arg Pro Ile Thr
        175                 180                 185 gtc cag ccc act gaa gcc tgg ccc aga acc tca cag gga ccc tcc acc      626
Val Gln Pro Thr Glu Ala Trp Pro Arg Thr Ser Gln Gly Pro Ser Thr
    190                 195                 200 cgg ccc gtg gag gtc ccc ggg ggc cgt gcg gtt gcc gcc atc ctg ggc      674
Arg Pro Val Glu Val Pro Gly Gly Arg Ala Val Ala Ala Ile Leu Gly
205                 210                 215                 220 ctg ggc ctg gtg ctg ggg ctg ctg ggc ccc ctg gcc atc ctg ctg gcc      722
Leu Gly Leu Val Leu Gly Leu Leu Gly Pro Leu Ala Ile Leu Leu Ala
                225                 230                 235 ctg tac ctg ctc cgg agg gac cag agg ctg ccc ccc gat gcc cac aag      770
Leu Tyr Leu Leu Arg Arg Asp Gln Arg Leu Pro Pro Asp Ala His Lys
            240                 245                 250 ccc cct ggg gga ggc agt ttc cgg acc ccc atc caa gag gag cag gcc      818
Pro Pro Gly Gly Gly Ser Phe Arg Thr Pro Ile Gln Glu Glu Gln Ala
        255                 260                 265 gac gcc cac tcc acc ctg gcc aag atc tgacctgggc ccaccaaggt           865
Asp Ala His Ser Thr Leu Ala Lys Ile
    270                 275

<210> SEQ ID NO 28
<211> LENGTH: 277
<212> TYPE: PRT
<213> ORGANISM: Homo sapiens

<400> SEQUENCE: 28

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140
```

```
Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Ala Thr Gln Pro
            165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 29
<211> LENGTH: 1599
<212> TYPE: DNA
<213> ORGANISM: Homo sapiens
<220> FEATURE:
<221> NAME/KEY: CDS
<222> LOCATION: (67)..(1596)

<400> SEQUENCE: 29
ccacaccaag cagcggctgg gggggggaaa gacgaggaaa gaggaggaaa acaaaagctg      60 ctactt atg gaa gat aca aag gag tct aac gtg aag aca ttt tgc tcc      108
       Met Glu Asp Thr Lys Glu Ser Asn Val Lys Thr Phe Cys Ser
         1               5                  10 aag aat atc cta gcc atc ctt ggc ttc tcc tct atc ata gct gtg ata      156
Lys Asn Ile Leu Ala Ile Leu Gly Phe Ser Ser Ile Ile Ala Val Ile
 15              20                  25                  30 gct ttg ctt gct gtg ggg ttg acc cag aac aaa gca ttg cca gaa aac      204
Ala Leu Leu Ala Val Gly Leu Thr Gln Asn Lys Ala Leu Pro Glu Asn
                 35                  40                  45 gtt aag tat ggg att gtg ctg gat gcg ggt tct tct cac aca agt tta      252
Val Lys Tyr Gly Ile Val Leu Asp Ala Gly Ser Ser His Thr Ser Leu
             50                  55                  60 tac atc tat aag tgg cca gca gaa aag gag aat gac aca ggc gtg gtg      300
Tyr Ile Tyr Lys Trp Pro Ala Glu Lys Glu Asn Asp Thr Gly Val Val
         65                  70                  75 cat caa gta gaa gaa tgc agg gtt aaa ggt cct gga atc tca aaa ttt      348
His Gln Val Glu Glu Cys Arg Val Lys Gly Pro Gly Ile Ser Lys Phe
     80                  85                  90 gtt cag aaa gta aat gaa ata ggc att tac ctg act gat tgc atg gaa      396
Val Gln Lys Val Asn Glu Ile Gly Ile Tyr Leu Thr Asp Cys Met Glu
 95                 100                 105                 110 aga gct agg gaa gtg att cca agg tcc cag cac caa gag aca ccc gtt      444
Arg Ala Arg Glu Val Ile Pro Arg Ser Gln His Gln Glu Thr Pro Val
                115                 120                 125 tac ctg gga gcc acg gca ggc atg cgg ttg ctc agg atg gaa agt gaa      492
Tyr Leu Gly Ala Thr Ala Gly Met Arg Leu Leu Arg Met Glu Ser Glu
            130                 135                 140 gag ttg gca gac agg gtt ctg gat gtg gtg gag agg agc ctc agc aac      540
Glu Leu Ala Asp Arg Val Leu Asp Val Val Glu Arg Ser Leu Ser Asn
        145                 150                 155
```

| | | |
|---|---|---|
| tac ccc ttt gac ttc cag ggt gcc agg atc att act ggc caa gag gaa<br>Tyr Pro Phe Asp Phe Gln Gly Ala Arg Ile Ile Thr Gly Gln Glu Glu<br>160                        165                     170 | 588 |
| ggt gcc tat ggc tgg att act atc aac tat ctg ctg ggc aaa ttc agt<br>Gly Ala Tyr Gly Trp Ile Thr Ile Asn Tyr Leu Leu Gly Lys Phe Ser<br>175                    180                     185                     190 | 636 |
| cag aaa aca agg tgg ttc agc ata gtc cca tat gaa acc aat aat cag<br>Gln Lys Thr Arg Trp Phe Ser Ile Val Pro Tyr Glu Thr Asn Asn Gln<br>                     195                     200                     205 | 684 |
| gaa acc ttt gga gct ttg gac ctt ggg gga gcc tct aca caa gtc act<br>Glu Thr Phe Gly Ala Leu Asp Leu Gly Gly Ala Ser Thr Gln Val Thr<br>              210                     215                     220 | 732 |
| ttt gta ccc caa aac cag act atc gag tcc cca gat aat gct ctg caa<br>Phe Val Pro Gln Asn Gln Thr Ile Glu Ser Pro Asp Asn Ala Leu Gln<br>        225                     230                     235 | 780 |
| ttt cgc ctc tat ggc aag gac tac aat gtc tac aca cat agc ttc ttg<br>Phe Arg Leu Tyr Gly Lys Asp Tyr Asn Val Tyr Thr His Ser Phe Leu<br>240                        245                     250 | 828 |
| tgc tat ggg aag gat cag gca ctc tgg cag aaa ctg gcc aag gac att<br>Cys Tyr Gly Lys Asp Gln Ala Leu Trp Gln Lys Leu Ala Lys Asp Ile<br>255                    260                     265                     270 | 876 |
| cag gtt gca agt aat gaa att ctc agg gac cca tgc ttt cat cct gga<br>Gln Val Ala Ser Asn Glu Ile Leu Arg Asp Pro Cys Phe His Pro Gly<br>                     275                     280                     285 | 924 |
| tat aag aag gta gtg aac gta agt gac ctt tac aag acc ccc tgc acc<br>Tyr Lys Lys Val Val Asn Val Ser Asp Leu Tyr Lys Thr Pro Cys Thr<br>              290                     295                     300 | 972 |
| aag aga ttt gag atg act ctt cca ttc cag cag ttt gaa atc cag ggt<br>Lys Arg Phe Glu Met Thr Leu Pro Phe Gln Gln Phe Glu Ile Gln Gly<br>        305                     310                     315 | 1020 |
| att gga aac tat caa caa tgc cat caa agc atc ctg gag ctc ttc aac<br>Ile Gly Asn Tyr Gln Gln Cys His Gln Ser Ile Leu Glu Leu Phe Asn<br>320                        325                     330 | 1068 |
| acc agt tac tgc cct tac tcc cag tgt gcc ttc aat ggg att ttc ttg<br>Thr Ser Tyr Cys Pro Tyr Ser Gln Cys Ala Phe Asn Gly Ile Phe Leu<br>335                    340                     345                     350 | 1116 |
| cca cca ctc cag ggg gat ttt ggg gca ttt tca gct ttt tac ttt gtg<br>Pro Pro Leu Gln Gly Asp Phe Gly Ala Phe Ser Ala Phe Tyr Phe Val<br>                     355                     360                     365 | 1164 |
| atg aag ttt tta aac ttg aca tca gag aaa gtc tct cag gaa aag gtg<br>Met Lys Phe Leu Asn Leu Thr Ser Glu Lys Val Ser Gln Glu Lys Val<br>              370                     375                     380 | 1212 |
| act gag atg atg aaa aag ttc tgt gct cag cct tgg gag gag ata aaa<br>Thr Glu Met Met Lys Lys Phe Cys Ala Gln Pro Trp Glu Glu Ile Lys<br>        385                     390                     395 | 1260 |
| aca tct tac gct gga gta aag gag aag tac ctg agt gaa tac tgc ttt<br>Thr Ser Tyr Ala Gly Val Lys Glu Lys Tyr Leu Ser Glu Tyr Cys Phe<br>400                        405                     410 | 1308 |
| tct ggt acc tac att ctc tcc ctc ctt ctg caa ggc tat cat ttc aca<br>Ser Gly Thr Tyr Ile Leu Ser Leu Leu Leu Gln Gly Tyr His Phe Thr<br>415                        420                     425                     430 | 1356 |
| gct gat tcc tgg gag cac atc cat ttc att ggc aag atc cag ggc agc<br>Ala Asp Ser Trp Glu His Ile His Phe Ile Gly Lys Ile Gln Gly Ser<br>                     435                     440                     445 | 1404 |
| gac gcc ggc tgg act ttg ggc tac atg ctg aac ctg acc aac atg atc<br>Asp Ala Gly Trp Thr Leu Gly Tyr Met Leu Asn Leu Thr Asn Met Ile<br>              450                     455                     460 | 1452 |
| cca gct gag caa cca ttg tcc aca cct ctc tcc cac tcc acc tat gtc<br>Pro Ala Glu Gln Pro Leu Ser Thr Pro Leu Ser His Ser Thr Tyr Val<br>465                        470                     475 | 1500 |

```
ttc ctc atg gtt cta ttc tcc ctg gtc ctt ttc aca gtg gcc atc ata      1548
Phe Leu Met Val Leu Phe Ser Leu Val Leu Phe Thr Val Ala Ile Ile
        480                 485                 490 ggc ttg ctt atc ttt cac aag cct tca tat ttc tgg aaa gat atg gta      1596
Gly Leu Leu Ile Phe His Lys Pro Ser Tyr Phe Trp Lys Asp Met Val
495                 500                 505                 510 tag                                                                   1599

<210> SEQ ID NO 30
<211> LENGTH: 510
<212> TYPE: PRT
<213> ORGANISM: Homo sapiens

<400> SEQUENCE: 30

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
```

```
                 325                 330                 335
Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Ile Lys Thr Ser
385                 390                 395                 400

Tyr Ala Gly Val Lys Glu Lys Tyr Leu Ser Glu Tyr Cys Phe Ser Gly
            405                 410                 415

Thr Tyr Ile Leu Ser Leu Leu Leu Gln Gly Tyr His Phe Thr Ala Asp
        420                 425                 430

Ser Trp Glu His Ile His Phe Ile Gly Lys Ile Gln Gly Ser Asp Ala
    435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
            485                 490                 495

Leu Ile Phe His Lys Pro Ser Tyr Phe Trp Lys Asp Met Val
        500                 505                 510

<210> SEQ ID NO 31
<211> LENGTH: 8
<212> TYPE: PRT
<213> ORGANISM: Artificial sequence
<220> FEATURE:
<223> OTHER INFORMATION: Flag peptide

<400> SEQUENCE: 31

Asp Tyr Lys Asp Asp Asp Asp Lys
1               5

<210> SEQ ID NO 32
<211> LENGTH: 11
<212> TYPE: PRT
<213> ORGANISM: Artificial Sequence
<220> FEATURE:
<223> OTHER INFORMATION: linker

<400> SEQUENCE: 32

Gly Gly Gly Gly Ser Gly Gly Gly Gly Ser
1               5                   10

<210> SEQ ID NO 33
<211> LENGTH: 13
<212> TYPE: PRT
<213> ORGANISM: Artificial sequence
<220> FEATURE:
<223> OTHER INFORMATION: linker

<400> SEQUENCE: 33

Gly Ala Gly Gly Ala Gly Ser Gly Gly Gly Gly Ser
1               5                   10

<210> SEQ ID NO 34
<211> LENGTH: 10
<212> TYPE: PRT
<213> ORGANISM: Artificial sequence
<220> FEATURE:
```

```
<223> OTHER INFORMATION: linker

<400> SEQUENCE: 34

Gly Gly Gly Gly Ser Gly Gly Gly Gly Ser
1               5                   10

<210> SEQ ID NO 35
<211> LENGTH: 9
<212> TYPE: PRT
<213> ORGANISM: Artificial sequence
<220> FEATURE:
<223> OTHER INFORMATION: peptide

<400> SEQUENCE: 35

Gly Thr Pro Gly Thr Pro Gly Thr Pro
1               5

<210> SEQ ID NO 36
<211> LENGTH: 26
<212> TYPE: PRT
<213> ORGANISM: Artificial Sequence
<220> FEATURE:
<223> OTHER INFORMATION: peptide

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Gly Ser
            20                  25
```

METHODS OF REDUCING INFLAMMATION IN CARDIOMYOPATHY

CROSS REFERENCE TO RELATED APPLICATIONS

This application is a continuation of U.S. patent application Ser. No. 10/646,308, filed Aug. 21, 2003, which claims the benefit under 35 U.S.C. §119 of U.S. Provisional Application Ser. No. 60/494,457, filed Aug. 12, 2003, and U.S. Provisional Application Ser. No. 60/406,418, filed Aug. 28, 2002.

REFERENCE TO THE SEQUENCE LISTING

The present application is being filed along with a Sequence Listing in electronic format. The. Sequence Listing is provided as a file entitled 3432-US-CNT Seq List.txt, created Jun. 26. 2012, which is 129 KB in size. The information in the electronic format of the Sequence Listing is incorporated herein by reference in its entirety.

FIELD OF THE INVENTION

Embodiments of the invention pertain to compositions and methods for treating cardiovascular disease by modulating inflammatory and immunoregulatory responses associated with cardiovascular disease.

BACKGROUND

Cardiovascular disease encompasses a number of disorders that affect the muscle and/or blood vessels of the heart, peripheral blood vessels, muscles and various organs. It is established in the art that inflammatory and immunoregulatory processes are implicated in the pathogenesis of various forms of cardiovascular disease.

For example, inflammatory immune responses have been shown to contribute to the pathogenesis of atherosclerosis. Elevated levels of C-reactive protein (CRP) have been associated with up to an 8.6 fold increase in the relative risk of symptomatic atherosclerosis (Biasucci, L., et al., *Circulation* 1999, 99:855-860). Elevated levels of CRP also predict patients that are at elevated risk of myocardial infarction (MI) or stroke, and it has also been associated with poor prognosis in unstable angina (Vorchheimer, D., et al., *JAMA* 2001, 286: 2154-2156). Binding C1q CRP activates the classical complement pathway and may lead to direct myocardial damage, coronary smooth muscle or endothelial cell death and subsequent atherosclerotic plaque rupture (Agrawal, A., et al., *J Immunol* 2001, 166:3998-4004). Furthermore, a recent study demonstrated that elevated levels of CRP are able to identify patients that die of sudden cardiac death 9 years prior to the event (Albert, C., et al., *Circulation* 2002, 105:2595-9). These studies also imply that long-term inflammatory exposure and elevated CRP levels may contribute to the progression of acute coronary syndromes (Buffon, A., et al., *NEJM* 2002, 347:55-7). Activation of inflammatory cells resident within an atherosclerotic plaque may elaborate enzymes capable of degrading extracellular matrix and lead to plaque rupture. Alternatively, these inflammatory cells may directly kill endothelial and smooth muscle cells. A number of studies have demonstrated that patients with unstable angina have peripheral T-cells that make enhanced levels of interferon gamma compared to patients with stable angina. Furthermore, there appears to be clonal expansion of a CD4+ CD28null T-cell population in these patients, which appear to be cytotoxic and can kill endothelial cells, an effect enhanced by CRP (Nakajima, T., et al., *Circulation* 2002, 105:570-5).

Cytokines are critical regulators of the T-helper 1 (Th1) and Th2 T-cell responses. The Th1 response results in pro-inflammatory cytokine release characterized by macrophage activation and, if unopposed, may result in tissue damage. The Th2 response results in a humoral immune response, B-cell activation and an allergic reaction (Neurath, M., et al., *Nat Med* 2002, 8:567-73). A number of Th1 type cytokines including TNF, IL-6 and the chemokine MCP-1 are elevated in unstable angina (*AJC* 2001, 88(8A):10K-15K). Recently, IL-18 has been found to be an independent marker for an adverse outcome in patients diagnosed with acute coronary syndrome (Blankenberg, S., et al., *Circulation* 2002, 106:24-30). Elevated levels of IL-18 have also been found to correlate with ulcerated, symptomatic carotid artery lesions (Mallat, Z., et al., *Circulation* 2001, 104:1598-603). In a mouse model of atherosclerotic plaque development in ApoE deficient mice, IL-18 was shown to accelerate and enhance plaque formation, and IL-18 binding protein enhanced smooth muscle proliferation, which would promote plaque stability by increasing the thickness of the cap, and reduced the number of infiltrating macrophages and T-cells (Mallat, Z., et al., *Circ Res.* 2001, 89:E41-5). Studies such as these establish a sound basis for implicating inflammatory and immunoregulatory responses in cardiovascular disease.

There is an unmet need in the art for treating cardiovascular disease by targeting the immunopathology of the disease. Embodiments of the present invention address such needs by providing compositions and methods for treating cardiovascular disease by modulating the inflammatory and immunoregulatory responses associated with cardiovascular disease.

SUMMARY OF THE INVENTION

Embodiments of the present invention provide compositions and methods for the treatment of cardiovascular disease in a subject having cardiovascular disease, comprising administering an effective amount of one or more antagonists, such as IL-17 antagonists that inhibit the binding of IL-17 to the IL-17 receptor, as well as antagonists that prevent or diminish the activation of the IL-17 receptor; IL-18 antagonists that inhibit the binding of IL-18 to the IL-18 receptor, as well as antagonists that prevent or diminish the activation of the IL-18 receptor; 4-1BB antagonists that inhibit the binding of 4-1BB ligand to 4-1BB, as well as antagonists that prevent or diminish the activation of 4-1BB ligand or 4-1BB; CD30 antagonists that inhibit the binding of CD30 ligand to CD30, as well as antagonists that prevent or diminish the activation of the CD30; OX40 antagonists that inhibit the binding of OX40 ligand to OX40, as well as antagonists that prevent or diminish the activation of OX40; and/or CD39 alone or in any combination. Additional embodiments are described in detail below.

BRIEF DESCRIPTION OF THE FIGURES

FIGS. 3B and 3D further dissect the patient population into non-ischemic and ischemic groups.

FIG. 7A shows IL-17 levels in mice from the experimental autoimmune myocarditis (EAM) model, wherein mice having histologically demonstrated cardiopathology (animal B) had higher expression levels of IL-17 over negative controls (animals C and D). FIG. 7B shows that IL-17 release from T-cells obtained from mice with EAM mice was approximately 25 fold higher compared to control mice. T-cells were isolated from animals immunized with cardiac myosin and exposed to antigen presenting cells fed myosin over antigen presenting cells not exposed to myosin. FIG. 7C illustrates that T-cells from an animal immunized with cardiac myosin and having histological evidence of cardiopathology (animal B) released high levels of IL-17 in response to antigen-specific stimulation by peptide-pulsed antigen presenting cells.

DETAILED DESCRIPTION OF THE INVENTION

Figure 1A:
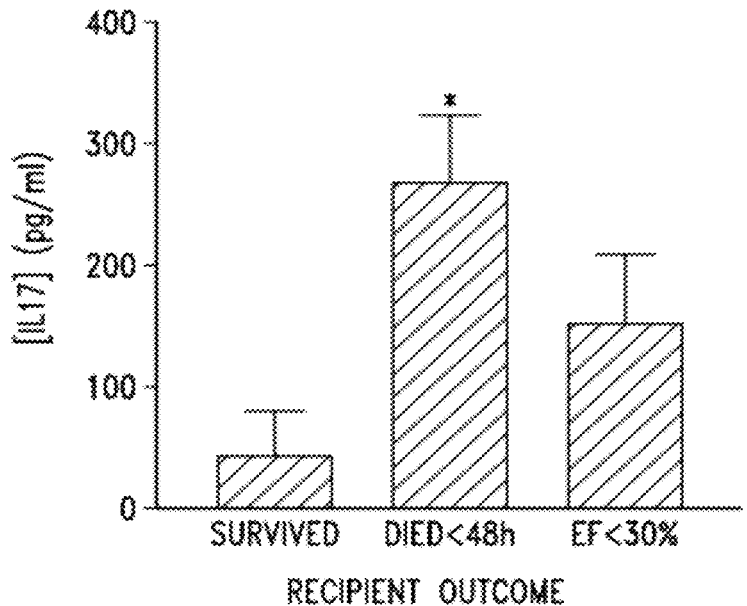
FIGS. 1A and 1B depict IL-17 and IL-18 levels, respectively, in heart donor plasma in relation to three distinct groups: surviving donor recipients, donor recipients that died in less than 48 hrs. and unused donors with an ejection fraction (EF) of less than 30%.

Embodiments of the invention provide compositions and methods for treating cardiovascular disease in a subject having cardiovascular disease comprising administering an effective amount of one or more IL-17 antagonists, IL-18 antagonists, 4-1BB antagonists, CD30 antagonists, OX40 antagonists and/or CD39, alone or in any combination.

Cardiovascular disease, as defined herein, encompasses diseases and disorders of the muscle and/or blood vessels of the heart, diseases and disorders of the vascular system, and/or diseases and disorders of organs and anatomical systems caused by the diseased condition of the heart and/or vasculature. Examples include, but are not limited to: inflammation of the heart and/or vasculature such as myocarditis, chronic autoimmune myocarditis, bacterial and viral myocarditis, as well as infective endocarditis; heart failure; congestive heart failure; chronic heart failure; cachexia of heart failure; cardiomyopathy, including non-ischemic (dilated cardiomyopathy; idiopathic dilated cardiomyopathy; cardiogenic shock, heart failure secondary to extracorporeal circulatory support ("post-pump syndrome"), heart failure following ischemia/reperfusion injury, brain death associated heart failure (as described in Owen et al., 1999 (Circulation. 1999 May 18; 99(19):2565-70)); hypertrophic cardiomyopathy; restrictive cardiomyopathy; non-ischemic systemic hypertension; valvular disease; arythmogenic right ventricular cardiomyopathy) and ischemic (atherogenesis; atherosclerosis; arteriosclerosis; peripheral vascular disease; coronary artery disease; infarctions, including stroke, transient ischemic attacks and myocardial infarctions). Additional disease states encompassed by the definition of cardiovascular disease include: aneurysms; arteritis; angina; embolism; platelet-associated ischemic disorders; ischemia/reperfusion injury; restenosis; mitral and/or tricuspid regurgitation; mitral stenosis; silent myocardial ischemia; Raynaud's phenomena; thrombosis; deep venous thrombosis; pulmonary embolism; thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surfacethrombophlebitis; vasculitis, including Kawasaki's vasculitis; Takayasu's arteritis; veno-occlusive disease, giant cell arteritis, Wegener's granulomatosis; Schoenlein-Henoch purpura, as well as cardiovascular disease arising from periodontal infections by one or more oral pathogens, such as bacteria. The examples of cardiovascular disease provided above are merely illustrative and provided to aid those of skill in the art to appreciate the scope of cardiovascular disease that may be treated using the compositions and methods described herein. Of course, other cardiovascular disease conditions may exist that can be treated using the inventive compositions and methods. Additional examples of cardiovascular disease and disorders associated with cardiovascular disease, as well as complications arising from the treatment of cardiovascular disease, are provided in the section below pertaining to therapeutic indications.

An "antagonist," as defined herein, is a molecule that partially or completely blocks the binding of two cognates thereby inhibiting the downstream biological effects of the cognates' interaction. For example, an antagonist may block the binding of a ligand to its receptor, which in turn reduces and/or prevents intracellular signalling via activating that receptor, which in turn reduces or prevents the downstream biological effects of activating that receptor, such as but not limited to, cell activation, proliferation, differentiation, cytokine release, up-regulation of genes, cell-surface expression of proteins, and the like.

Activating or activation of a receptor is defined herein as the engagement of one or more intracellular signaling pathway(s) and the transduction of intracellular signaling (i.e., signal transduction) in response to a molecule binding to a membrane-bound receptor, such as but not limited to, a receptor:ligand interaction.

"Signal transduction," as used herein, is the relaying of a signal by conversion from one physical or chemical form to another. In cell biology, the process by which a cell converts an extracellular signal into a response.

Antagonists presented herein comprise soluble receptor molecules, ligands and/or binding proteins, including IL-17, IL-17 receptor (IL-17R), IL-18, IL-18 receptor (IL-18R), IL-18 binding protein (IL-18BP), CD30, CD30 ligand (CD30-L), 4-1BB, 4-1BB ligand (4-1BB-L), OX40, OX40 ligand (OX40-L) and CD39. Antagonists presented herein further comprise antibodies, fusion proteins and peptibodies directed against one or more of the following: IL-17, IL-17R, IL-18, IL-18R, CD30, CD30-L, 4-1BB, 4-1BB-L, OX40 and/or OX40-L. Antagonists presented herein further comprise small molecules, such as peptidomimetics and mimotopes, and the like, that antagonize the interaction between IL-17 and IL-17R, IL-18 and IL-18R, 4-1BB and 4-1BB-L, CD30 and CD30-L and/or OX40 and OX40-L. Additional antagonists comprise antisense oligonucleotides that specifically target and hybridize to the mRNA of IL-17, IL-17R, IL-18, IL-18R, CD30, CD30-L, 4-1BB, 4-1BB-L, OX40 and/or OX40-L thereby preventing gene translation of their respective proteins. Further embodiments comprise gene silencing by RNA-interference molecules tailored to silence expression of IL-17, IL-17R, IL-18, IL-18R, 4-1BB, 4-1BB-L, CD30, CD30-L, OX40 and/or OX40-L. More specific definitions and examples of particular antagonists are provided in the sections below.

A "peptibody" refers to molecules comprising an Fc domain and at least one peptide. Such peptibodies may be multimers or dimers or fragments thereof, and they may be derivatized. Peptibodies are described in greater detail in WO 99/25044 and WO 00/24782, which are incorporated herein by reference in their entirety. The peptide may be from the amino acid sequence of IL-17, IL-17 receptor (IL-17R), IL-18, IL-18 receptor (IL-18R), IL-18 binding protein (IL-18BP), CD30, CD30 ligand (CD30-L), 4-1BB, 4-1BB ligand (4-1BB-L), OX40, OX40 ligand (OX40-L) and/or CD39.

A "peptide," as used herein refers to molecules of 1 to 40 amino acids. Alternative embodiments comprise molecules of 5 to 20 amino acids. Exemplary peptides may comprise portions of the extracellular domain of naturally occurring molecules or comprise randomized sequences of of IL-17, IL-17 receptor (IL-17R), IL-18, IL-18 receptor (IL-18R), IL-18 binding protein (IL-18BP), CD30, CD30 ligand (CD30-L), 4-1BB, 4-1BB ligand (4-1BB-L), OX40, OX40 ligand (OX40-L) and/or CD39.

The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, RNA-peptide screening, chemical screening, and the like.

The term "Fc domain" encompasses native Fc and Fc variant molecules and sequences as defined below. As with Fc variants and native Fc's, the term "Fc domain" includes molecules in monomeric or multimeric form, whether digested from whole antibody or produced by other means.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

A "peptidomimetic" is a peptide analog that displays more favorable pharmacological properties than their prototype native peptides, such as a) metabolic stability, b) good bioavailability, c) high receptor affinity and receptor selectivity, and d) minimal side effects. Designing peptidomimetics and methods of producing the same are known in the art (see for example, U.S. Pat. Nos. 6,407,059 and 6,420,118). Peptidomimetics may be derived from the binding site of the extracellular domain of IL-17, IL-17 receptor (IL-17R), IL-18, IL-18 receptor (IL-18R), IL-18 binding protein (IL-18BP), CD30, CD30 ligand (CD30-L), 4-1BB, 4-1BB ligand (4-1BB-L), OX40, OX40 ligand (OX40-L) and/or CD39. In alternative embodiments, a peptidomimetic comprises non-peptide compounds having the same three-dimensional structure as peptides derived from IL-17, IL-17 receptor (IL-17R), IL-18, IL-18 receptor (IL-18R), IL-18 binding protein (IL-18BP), CD30, CD30 ligand (CD30-L), 4-1BB, 4-1BB ligand (4-1BB-L), OX40, OX40 ligand (OX40-L) and/or CD39, or compounds in which part of a peptide from the molecules listed above is replaced by a non-peptide moiety having the same three-dimensional structure.

A "mimotope" is defined herein as peptide sequences that mimic binding sites on proteins (see, Partidos, CD, et al., *Combinatorial Chem & High Throughput Screening*, 2002 5:15-27). A mimotope may have the capacity to mimic a conformationally-dependent binding site of a protein. The sequences of these mimotopes do not identify a continuous linear native sequence or necessarily occur in a naturally-occurring protein. Mimotpes and methods of production are taught in U.S. Pat. No. 5,877,155 and U.S. Pat. No. 5,998,577, which are incorporated by reference in their entireties.

The term "acidic residue" refers to amino acid residues in D- or L-form having sidechains comprising acidic groups. Exemplary acidic residues include D and E.

The term "amide residue" refers to amino acids in D- or L-form having sidechains comprising amide derivatives of acidic groups. Exemplary residues include N and Q.

The term "aromatic residue" refers to amino acid residues in D- or L-form having sidechains comprising aromatic groups. Exemplary aromatic residues include F, Y, and W.

The term "basic residue" refers to amino acid residues in D- or L-form having sidechains comprising basic groups. Exemplary basic residues include H, K, and R.

The term "hydrophilic residue" refers to amino acid residues in D- or L-form having sidechains comprising polar groups. Exemplary hydrophilic residues include C, S, T, N, and Q.

The term "nonfunctional residue" refers to amino acid residues in D- or L-form having sidechains that lack acidic, basic, or aromatic groups. Exemplary nonfunctional amino acid residues include M, G, A, V, I, L and norleucine (Nle).

The term "neutral hydrophobic residue" refers to amino acid residues in D- or L-form having sidechains that lack basic, acidic, or polar groups. Exemplary neutral hydrophobic amino acid residues include A, V, L, I, P, W, M, and F.

The term "polar hydrophobic residue" refers to amino acid residues in D- or L-form having sidechains comprising polar groups. Exemplary polar hydrophobic amino acid residues include T, G, S, Y, C, Q, and N.

The term "hydrophobic residue" refers to amino acid residues in D- or L-form having sidechains that lack basic or acidic groups. Exemplary hydrophobic amino acid residues include A, V, L, I, P, W, M, F, T, G, S, Y, C, Q, and N.

The term "subject" as used herein, refers to mammals. For example, mammals contemplated by the present invention include humans; primates; pets of all sorts, such as dogs, cats, etc.; domesticated animals, such as, sheep, cattle, goats, pigs, horses and the like; common laboratory animals, such as mice, rats, rabbits, guinea pigs, etc.; as well as captive animals, such as in a zoo or free wild animals. Throughout the specification, the term host is used interchangeably with subject.

As used herein the singular forms "a", "and", and "the" include plural referents unless the context clearly dictates otherwise. Thus, for example, reference to "an immunization" includes a plurality of such immunizations and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

It is understood that the various embodiments of this invention are not limited to the particular methodology, protocols, cell lines, animal species or genera, constructs, and reagents described, as such may vary. It is also understood that the terminology used herein is for the purpose of describing particular embodiments only, and is not intended to limit the scope of the present invention which will be limited only by the appended claims.

I. IL-17, IL-18, 4-1BB, CD30 and OX40 Antagonists.

A. IL-17 Antagonists

Embodiments of the present invention provide compositions and methods for the treatment of cardiovascular disease comprising IL-17 antagonists. Studies presented herein demonstrate that IL-17 and IL-18 are elevated in human patients having various forms and severity of cardiovascular disease. These studies demonstrate that circulating levels of IL-17 and/or IL-18 correlate with severity of cardiovascular disease. Furthermore, plasma levels of IL-17 and/or IL-18 are elevated in a cardiac myosin-induced myocarditis model and correlate with disease severity. Therefore, IL-17 and/or IL-18 are implicated in cardiovascular disease and provide a rational basis for treating cardiovascular disease by administering IL-17 and/or IL-18 antagonists, alone or in combination. In addition, IL-17 and/or IL-18 are prognostic indicators of cardiovascular disease and disease severity. IL-17 and/or IL-18 are also prognostic indicators of donor adequacy and post-transplant outcome. Therefore, further embodiments of the invention include assays for measuring IL-17 and/or IL-18 levels in subjects being screened for cardiovascular disease, cardiovascular disease severity, donor adequacy and post-transplant outcome.

An IL-17 antagonist is defined herein as an entitiy that is capable of reducing the effective amount of endogenous IL-17 in a subject, by either partially or completely blocking the interaction of IL-17 and the IL-17 receptor and thereby inhibiting IL-17-mediated signaling via membrane-bound IL-17 receptor, as well as partially or completely inhibiting the subsequent biological effects of activating the IL-17 receptor. An IL-17 antagonist may bind to IL-17 or to the IL-17 receptor.

Such IL-17 antagonists include, but are not limited to: soluble forms of IL-17 receptor; antibodies directed against IL-17 that specifically bind IL-17 and partially or completely inhibit binding of IL-17 to IL-17 receptor; antibodies, fusion proteins and/or peptibodies directed against IL-17 receptor that specifically bind IL-17 receptor and inhibit binding of IL-17 without themselves activating the IL-17 receptor; molecules that bind IL-17 or IL-17 receptor and inhibit the interaction thereof, such as IL-17 and/or IL-17 receptor peptidomimetics and/or mimotopes. As used herein, when reference is made to making IL-17 antagonists based on IL-17 or IL-17 receptor, it is understood that the terms IL-17 and IL-17 receptor also encompass fragments, variants, muteins, derivatives and fusion proteins thereof, as described in detail below.

Biological activity of IL-17 and IL-17R is defined herein as comprising binding of IL-17 to the IL-17R and activation of the IL-17R; proinflammatory effects; increased production of cytokines and chemokines, such as but not limited to, IL-6, IL-8, G-CSF, GM-CSF, MCP-1, Groa, PGE2, as well as induction of costimulatory molecule ICAM. The IL-17:IL-17R interaction also has the biological activities of recruiting monocytes and neutrophils, up-regulation of iNOS, NO and COX-2; activation of all three subgroups of MAPKs (the p44 and p42 extracellular signal-regulated kinases ERK1 and ERK2), NFκB, stress-induced Jun NH2-terminal kinases (JNK1 and JNK2) and p38. Of course, it is understood that intermediate pathways that culminate in such biological activities are also included in the definition of biological activity for IL-17 and IL-17R.

IL-17 antagonists may comprise or be developed from IL-17 receptor polypeptide and/or polynucleotide sequences, as well as fragments, variants, muteins, derivatives and fusion proteins thereof. The isolation, cloning, preparation and characterization of human IL-17 receptor (referred to interchangably as IL-17R or huIL-17R) are described in U.S. Pat. Nos. 5,869,286 and U.S.P.N. 6,072,033, which are incorporated herein by reference in their entirety. The full-length cDNA sequence for human IL-17R is provided in SEQ ID NO:3 and the corresponding amino acid sequence is provided in SEQ ID NO:4.

The human IL-17 receptor has an N-terminal signal peptide with a predicted cleavage site between amino acid 27 and 28. The signal peptide is followed by a 293 amino acid extracellular domain, a 21 amino acid transmembrane domain, and a 525 amino acid cytoplasmic tail. Soluble polypeptides are polypeptides that are capable of being secreted from the cells in which they are expressed. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of IL-17 receptor is advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures. Soluble forms of IL-17R that are useful in the methods of treating cardiovascular disease include the extracellular domain (residues 1-320 of SEQ ID N0:4 or residues 28-320 which excludes the signal peptide) or a fragment of the extracellular domain that has the properties of antagonizing or preventing binding of IL-17 to endogenous IL-17R. Soluble IL-17R also includes those polypeptides which include part of the transmembrane region, provided that the soluble IL-17R is capable of being secreted from a cell, and preferably retains the capacity to bind IL-17 and effectuate its biological effects.

Other forms of the IL-17R that are useful in the present invention include muteins and variants (also referred to as analogs), such as naturally occurring variants, that are substantially homologous to the native IL-17R of SEQ ID NO:4 and as described in U.S. Pat. No. 6,072,033 that retain biological activity of IL-17R.

The invention further encompasses IL-17 antagonists derived from IL-17R polynucleotide sequences. Embodiments of the invention include full length nucleic acid molecules encoding soluble IL-17R as well as isolated fragments and oligonucleotides derived from the nucleotide sequence of SEQ ID NO:3. Such nucleic acid sequences may include nucleotides 178-1494 of SEQ ID NO:3 or a fragment thereof, and DNA and/or RNA sequences that hybridize to the coding region of the nucleotide sequence of SEQ ID NO:3, or its complement, under conditions of moderate stringency, and which encode polypeptides or fragments thereof of the invention.

In other embodiments, IL-17 antagonists may comprise or be developed from IL-17 polynucleotide and/or polypeptide sequences. The full-length cDNA sequence for human IL-17 is provided in SEQ ID NO: 1 and the corresponding amino acid sequence is provided in SEQ ID NO: 2. Commercially available recombinant human IL-17 is also available, for example, from R&D Systems, Minneapolis, Minn. IL-17 polypeptides, as well as biologically active fragments or derivatives thereof, may be used to generate antibodies that specifically bind to IL-17 and have the capacity of partially or completely blocking IL-17 binding to the IL-17 receptor.

In further embodiments, IL-17 antagonists are small molecules and polypeptide mimetics, such as but not limited to, peptidomimetics, peptibodies and/or mimotopes developed from the polypeptide sequence of IL-17 (SEQ ID NO:2) and/or IL-17R (SEQ ID NO:4). Polypeptide mimetics are peptide-containing molecules which mimic elements of protein secondary structure. Polypeptide mimetics, such as peptidomimetics and mimotopes, may be developed through techniques known in the art, such as combinatorial peptide libraries.

An IL-17 polypeptide mimetic based on the amino acid sequence of IL-17 will bind to IL-17R without activating the IL-17R and sterically hinder binding of endogenous IL-17. Conversely, an IL-17R polypeptide mimetic based on the amino acid sequence of IL-17R will bind to IL-17 and sterically hinder IL-17 from binding to endogenous IL-17R. IL-17 peptide mimetics may be used to antagonize IL-17 in a subject and thereby reduce the proinflammatory effects of IL-17. As such, IL-17 polypeptide mimetics may be used to treat inflammatory and/or immunoregulatory processes associated with cardiovascular disease.

Other forms of the IL-17 that are useful in the present invention include muteins and variants (also referred to as analogs), such as naturally occurring variants, that are substantially homologous to the native IL-17 of SEQ ID NO:2 that retain biological activity of IL-17. For example, IL-17 homologues B, C, D, E and F. This invention additionally provides for the use of IL-17 antagonists in the manufacture of a medicament for the treatment of cardiovascular disease. This invention further provides for the use of polynucleotides encoding IL-17 antagonists in the manufacture of a medicament for the treatment of cardiovascular disease.

B. IL-18 Antagonists

Embodiments of the present invention provide compositions and methods for the treatment of cardiovascular disease comprising IL-18 antagonists. An IL-18 antagonist is defined herein as an entitiy that is capable of reducing the effective amount of endogenous IL-18, by either partially or completely blocking the interaction of IL-18 and the IL-18R and thereby inhibiting IL-18-mediated signaling via membrane-bound IL-18R, as well as partially or completely inhibiting the subsequent biological effects of activating the IL-18 receptor. An IL-18 antagonist may bind to IL-18 or to the IL-18R. Antagonists derived from the IL-18R and IL-18 Binding Protein (e.g. soluble forms that bind IL-18) compete for IL-18 with IL-18R on the cell surface, thus inhibiting IL-18 from binding to cells, thereby preventing IL-18 from manifesting its biological activities.

IL-18:IL-18R biological activity, is defined herein as including, but is not limted to, binding of IL-18 to the IL-18R and activation of the IL-18R; regulation of innate and acquired immune responses; proinflammatory effects; induction of T-lymphocyte helper cell type 1 responses (Th1); enhance cell-mediated cytotoxicity; IFN-γ induction; enhanced production of GM-CSF and IL-2; potentiation of anti-CD3 induced T-cell proliferation; increased Fas-mediated kiling by natural killer cells (NK cells) and CD4+ Th1 cells; increased apoptotic death via the Fas-FasL pathway; up-regulation of FasL expression; induction of T-lymphocyte helper cell type 2 responses (Th2) in T-cells and NK cells; stimulation of basophils and mast cells to produce Th2 cytokines and histamine; induction of IgE production Such IL-18 antagonists include, but are not limited to: soluble forms of IL-18R; IL-18 Binding Protein; antibodies directed against IL-18 that specifically bind IL-18 and partially or completely inhibit binding of IL-18 to IL-18R; antibodies, fusion proteins and/or peptobodies directed against IL-18R that specifically bind IL-18R and inhibit receptor binding of IL-18 without themselves transducing a signal via IL-18R; small molecules that bind IL-18 or IL-18R that inhibit the interaction thereof, such as IL-18 and/or IL-18R peptidomimetics and/or mimotopes. As used herein, when reference is made to making IL-18 antagonists based on IL-18, IL-18 Binding Protein or IL-18 receptor, it is understood that the terms IL-18, IL-18 Binding Protein and IL-18 receptor also encompass fragments, variants, muteins, derivatives and fusion proteins thereof, as described in detail below.

The isolation, cloning, preparation and characterization of human IL-18 receptor (referred to interchangably as IL-18R or huIL-18R) are described in U.S. Pat. No. 6,087,116 and U.S. patent application Ser. No. 09/621,502 (PCT Publication WO 99/37772), which are incorporated herein by reference in their entirety. The IL-18 receptor is a heterodimeric protein containing an IL-18 binding subunit termed IL-1Rrp1, and an accessory subunit termed AcPL. Although the IL-Rrp1 subunit alone will bind IL-18, its affinity for IL-18 is increased dramatically when present in a heterodimeric complex with the AcPL subunit.

The IL-1Rrp1 polynucleotide sequence and corresponding amino acid sequence that it encodes are provided as SEQ ID NO:5 and SEQ ID NO:6, respectively. The soluble extracellular portion of the IL-1Rrp1 subunit that binds IL-18 is represented by amino acids 20 to 329 of SEQ ID NO:6; cleavage of the signal sequence occurs just after amino acid residue 19 of SEQ ID NO:6. However, fragments as small as amino acid residues 20 to 123 and amino acid residues 20 to 226 of SEQ ID NO:6 have been reported to bind IL-18 and can also be used. The IL-1Rrpl polypeptide is also described in U.S. Pat. No. 5,776,731, incorporated in its entirety by reference herein.

The AcPL polynucleotide sequence and the amino acid sequence that it encodes are provided herein as SEQ ID NO:7 and SEQ ID NO:8, respectively. The mature extracellular domain of AcPL consists of amino acids 15 to 356 of SEQ ID NO:8; cleavage of the signal sequence occurs just after amino acid residue 14 of SEQ ID NO:8. The AcPL polypeptide, and soluble extracellular fragments thereof, are also described in in U.S. patent application Ser. No. 09/621,502 (PCT Publication WO 99/37772), incorporated herein by reference in its entirety.

One embodiment of a soluble form of an IL-18 receptor for use in the methods of the present invention comprises amino acids 1-329 sequence of SEQ ID NO:6; alternative embodiments of a soluble form of an IL-18 receptor comprises amino acids 20-329 after cleavage of the signal sequence of SEQ ID NO:6. A further embodiment of a soluble form of IL-18 receptor is a heterodimeric receptor that includes at least amino acid residues 20-123, 20-226 or 20-329 of SEQ ID NO:6 (the IL-1Rrp1 subunit), and at least amino acids 15-340 of SEQ ID NO:8 (the AcPL subunit), in a covalent or non-covalent association.

Additional IL-18 antagonists comprise the IL-18 Binding Protein. PCT Publication WO 99/09063 describes the IL-18 binding protein, including useful soluble fragments thereof. One embodiment of a human IL-18 Binding Protein is the "a" isoform having the polynucleotide sequence of SEQ ID NO:9 and the corresponding amino acid sequence of SEQ ID NO:10. Of course, other IL-18 Binding Protein isoforms that are antagonistic to IL-18 binding to IL-18R may be used, such as the b, c and d isoforms. The polynucleotide and amino acid sequences for the b, c and d isoforms are known in the art and readily available (see for example, Kim, S.-H., et al., *PNAS* 97:3 1190-1195 (2000)). A particularly useful form of the IL-18 binding protein is a fusion with an Fc domain of an antibody. The amino acid sequence of an example of such a fusion protein, termed IL-18BP-Fc herein, is presented in SEQ ID NO:11. This 422 amino acid protein, when expressed in a mammalian cell, will be secreted; the mature secreted form of the protein contains amino acid residues 29-422. Of these residues, amino acid residues 29-192 represent the IL-18 binding protein portion of the molecule, and amino acid residues 193-422 represent the Fc portion of the molecule. The Fc region facilitates purification and dimerization of the fusion polypeptide.

IL-18 antagonists may also comprise or be developed from IL-18 polynucleotide and/or polypeptide sequences. Human IL-18 has been recombinantly produced from a cloned cDNA, as described in U.S. Pat. No. 5,891,663 and cloned genomic DNA, as disclosed in U.S. Pat, No. 6,060,283, which are incorporated by reference in their entirety. The full-length cDNA sequence in provided in SEQ ID NO:12 with the corresponding amino acid sequence in SEQ ID NO:13. The amino acid sequence for ICE-processed human IL-18 provided in SEQ ID NO:14. Commercially available recombinant human IL-18 is available, for example, from R&D Systems, Minneapolis, Minn. IL-18 polypeptides as well as biologically active fragments or derivatives thereof may be used to generate antibodies that specifically bind to IL-18 and have the capacity of partially or completely blocking IL-18 binding to the IL-18 receptor.

In one embodiment, IL-18 antagonists are polypeptide mimetics, such as, but not limited to peptidomimetics, peptibodies and/or mimotopes developed from the polypeptide sequence of IL-18 (SEQ ID NO:13 and/or 14). Polypeptide mimetics may be developed through techniques known in the art, such as combinatorial peptide libraries. Polypeptide mimetics are peptide-containing molecules which mimic elements of protein secondary structure. An IL-18 polypeptide mimetic based on the amino acid sequence of IL-18 will bind to IL-18 receptor without activating the IL-18 receptor and sterically hinder binding of endogenous IL-18. IL-18 peptide mimetics may be used to antagonize IL-18 in a subject and thereby reduce the proinflammatory effects of IL-18. As such, IL-18 polypeptide mimetics may be used to treat inflammatory and/or immunoregulatory processes associated with cardiovascular disease.

Other embodiments of IL-18, IL-18 receptor and IL-18 Binding Protein that may be used as IL-18 antagonists include muteins and variants (as described in greater detail below), such as naturally occurring variants, that are substantially homologous to the native IL-18 of SEQ ID NO:13 and/or 14, IL-18 receptor of SEQ ID NOs:6 and 8, and IL-18 Binding Protein of SEQ ID NO:10 that retain biological activity. Biological activity, in this instance, is the capacity to bind its cognate partner.

This invention additionally provides for the use of IL-18 antagonists in the manufacture of a medicament for the treatment of cardiovascular disease. This invention further provides for the use of polynucleotides encoding IL-18 antagonists in the manufacture of a medicament for the treatment of cardiovascular disease.

C. 4-1BB Antagonists

Further embodiments of the present invention provide compositions and methods for the treatment of cardiovascular disease comprising 4-1BB antagonists.

Examples 7 and 8 describe studies demonstrating a role for the 4-1BB/4-1BBL immune co-stimulatory pathway in Adriamycin®-induced cardiomyopathy, as well as deomonstrating a novel cardiac expression pattern of 4-1BB and implicating apoptosis as a mechanism of co-stimulatory contribution to Adriamycin®-induced cardiomyopathy. More specifically, 4-1BBL deficient mice and 4-1BBL decoy receptor-treated mice conferred partial resistance to adriamycin induced cardiac damage, whereas 4-1BB activating antibody accelerated onset of damage, implying the contribution of 4-1BB to Adriamycin® effects in heart. Apoptosis, measured by TUNEL, sub-G1 DNA and activated caspase-3, was increased in Adriamycin®-treated wild type myocardium, but reduced in 4-1BBL−/−. Phosphorylation of Akt was selectively suppressed by Adriamycin®, but maintained by loss of 4-1BBL, indicating the modulation of apoptosis by co-stimulatory pathway in heart is possibly through Akt, but not Jnk and p38 signaling. The consistency of decreased index of apoptosis and the improved cardiac function in 4-1BBL−/− suggests apoptosis play a pivotal role in Adriamycin®-induced cardiac deficiency.

A single retroorbital (RO) injection of adriamycin (22.5 mg/kg) leads to progressive cardiac dysfunction without evidence of inflammatory infiltration. In this model of noninflammatory, drug-induced cardiomyopathy, 4-1BBL−/− mice have substantially improved cardiac function by echocardiography. Furthermore, m4-1BB Fc (a soluble decoy receptor for 4-1BBL) reduced ADR cardiac dysfunction, while an agonistic antibody to 4-1BB (M6) accelerated and exacerbated cardiac dysfunction. While no inflammatory infiltrate is observed in this Adr-cardiomyopathy, we found expression of 4-1BB induced on 1-5% of cardiac interstitial cells within 2 days after Adr. Cardiac apoptosis, measured by TUNEL and sub-G1 DNA, is increased 3 days after ADR(45 mg/kg), concomitant with the increased expression of 4-1BB on interstitial cells. Chronic ongoing apoptosis, determined 5 weeks after Adr challenge when cardiac dysfunction is maximal in wild type but largely absent in 4-1BBL−/− mice, was lower in 4-1BBL−/− mice (1.5-fold vs baseline), compared to WT mice (4 fold). In a separate study, caspase 3 activation, determined by Western blot, was increased at 48 to 72 hrs post-ADR (45 mg/kg). In contrast, ADR did not induce caspase 3 cleavage in 4-1BBL−/− myocardium. Determined by western blot, adriamycin reduced phosphorylation of Akt in wild type but not 4-1BBL−/− hearts. Phosphorylation of JNK and p38 was not impacted by Adr. In summary, 4-1BB/4-1BBL immune co-stimulatory pathway contributes to ADR-induced cardiomyopathy, possibly, through modulation of Akt signaling to regulate apoptosis in the heart.

A 4-1BB antagonist is defined herein as an entitiy that is capable of reducing the effective amount of available endogenous 4-1BB and/or 4-1BB ligand (4-1BB-L), by either partially or completely blocking the interaction of 4-1BB and 4-1BB-L and thereby inhibiting 4-1BB-mediated signaling via 4-1BB-L and 4-1BB-L-mediated signaling via 4-1BB, as well as the subsequent biological effects of activating 4-1BB and/or 4-1BB-L. In other words, because the 4-1BB:4-1BB-L interaction exhibits bi-directional signalling, a 4-1BB antagonist may bind either 4-1BB or 4-1BB-L so long as the antagonist does not itself activate 4-1BB or 4-1BB-L. Such 4-1BB antagonists include, but are not limited to: soluble forms of 4-1BB; antibodies, fusion proteins and/or peptibodies directed against 4-1BB that specifically bind 4-1BB and partially or completely inhibit binding of 4-1BB to 4-1BB-L; antibodies, fuion proteins and/or peptibodies directed against 4-1BB that specifically bind 4-1BB and inhibit binding of 4-1BB-L without themselves transducing a signal via 4-1BB; molecules that bind 4-1BB or 4-1BB-L and inhibit the interaction thereof, such as 4-1BB and/or 4-1BB-L small molecules, peptidomimetics and/or mimotopes, and/or polypeptides comprising all or portions of 4-1BB or 4-1BB-L or modified variants thereof, including genetically-modified muteins, multimeric forms and sustained-release formulations thereof.

4-1BB:4-1BB-L biological activity, is defined herein as including, but is not limted to, binding of 4-1BB-L to 4-1BB and activation of one or both of 4-1BB and 4-1BB-L; costimulatory activity on T lymphocytes; activation and differentiation of CD4+ and CD8+ cells; signal transduction through TRAF pathways (TRAF1, TRAF2 and TRAF3) and activation of NFκB and AP-1; inhibition of activation-induced cell death; facilitation of B-cell proliferation and monocyte activation; up-regulation of cytokines including, but not limited to, IL-6, IL-8 and TNF-α; up-regulation of adhesion molecules, such as ICAM; down-regulation of FcγRIII; production of M-CSF in monocytes; monocyte proliferation; and inhibition of T-cell proliferation induced by anti-CD3 antibodies.

4-1BB antagonists may comprise or be developed from 4-1BB-L polypeptide and polynucleotide sequences. The isolation, cloning, preparation and characterization of human 4-1BB-L (referred to interchangably as hu4-1BB-L) is described in U.S. Pat. No. 5,674,704, which is incorporated herein by reference in its entirety. 4-1BB-L refers to a genus of mammalian polypeptides that are capable of binding 4-1BB. 4-1BB-L is a type II extracellular membrane polypeptide with an intracellular (cytoplasmic) domain at the N-terminus of the polypeptide (amino acids 1-25 of SEQ ID NO:15), followed by a transmembrane region polypeptide (amino acids 26-48 of SEQ ID NO:15), and an extracellular (receptor-binding) domain at the C-terminus of the polypeptide polypeptide (amino acids 49-254 of SEQ ID NO:15). Soluble 4-1BB-L polypeptides may be derived from the extracellular domain, as described below. The full-length cDNA sequence for human 4-1BB-L is provided in SEQ ID NO:14 and the corresponding amino acid sequence is provided in SEQ ID NO:15. The human 4-1BB-L protein comprises a cytoplasmic domain (amino acids 1-25), a transmembrane region (amino acids 26-48), and an extracellular domain (amino acids 49-254 of SEQ ID NO:15).

In addition, 4-1BB antagonists may comprise or be developed from 4-1BB polypeptide and polynucleotide sequences. The polynucleotide sequence of a human 4-1BB cDNA and the amino acid sequence encoded thereby are presented in SEQ ID NO:17 and SEQ ID NO:18, respectively. The human 4-1BB protein comprises an N-terminal signal sequence (amino acids −23 to −1 of SEQ ID NO:18), an extracellular domain comprising amino acids 1-163, a transmembrane region comprising amino acids 164-190, and a cytoplasmic domain comprising amino acids 191-232.

Soluble forms of 4-1BB-L and 4-1BB proteins are provided herein. Soluble 4-1BB-L or 4-1BB polypeptides comprise all or part of the extracellular domain but lack the transmembrane region that would cause retention of the polypeptide on a cell membrane. Since the 4-1BB-L protein lacks a signal peptide, a heterologous signal peptide may be fused to the N-terminus of soluble 4-1BB-L polypeptides to promote secretion thereof. The signal peptide is cleaved from the protein upon secretion from the host cell. Soluble 4-1BB-L polypeptides include fragments that retain the ability to bind 4-1BB, such as truncated polypeptides of the extracellular domain, and soluble 4-1BB polypeptides include fragments that retain the ability to bind 4-1BB-L, such as truncated polypeptides of the extracellular domain 4-1BB. In alternative embodiments, the soluble proteins may include part of the transmembrane region or part of the cytoplasmic domain, provided that the protein is capable of being secreted rather than retained on the cell surface. Examples of soluble polypeptides include those comprising the entire extracellular domain. Specific examples include, but are not limited to a soluble human 4-1BB-L polypeptide comprising amino acids 49-254 of SEQ ID NO:16 and a soluble human 4-1BB polypeptide comprising amino acids 1-163 of SEQ ID NO:18.

In one embodiment, 4-1BB antagonists are polypeptide mimetics, such as but not limited to, peptidomimetics, peptibodies and/or mimotopes developed from the polypeptide sequence of 4-1BB-L (SEQ ID NO:16) and 4-1BB (SEQ ID NO:18). Polypeptide mimetics may be developed through techniques known in the art, such as combinatorial peptide libraries. Polypeptide mimetics are peptide-containing molecules which mimic elements of protein secondary structure. A 4-1BB polypeptide mimetic based on the amino acid sequence of 4-1BB will bind to 4-1BB-L without activating 4-1BB-L and sterically hinder binding of endogenous 4-1BB. Similarly, a 4-1BB-L polypeptide mimetic based on the amino acid sequence of 4-1BB-L will bind to 4-1BB without activating 4-1BB and sterically hinder binding of endogenous 4-1BB-L. 4-1BB and 4-1BB-L peptide mimetics may be used to antagonize their respective cognates in a subject and thereby reduce the proinflammatory effects of the 4-1BB/4-1BB-L interaction. As such, 4-1BB antagonists in the form of polypeptide mimetics may be used to treat inflammatory and/or immunoregulatory processes associated with cardiovascular disease.

Other embodiments of 4-1BB and 4-1BB-L that may be used as 4-1BB antagonists include muteins and variants (as described in greater detail below), such as naturally occurring variants, that are substantially homologous to the native 4-1BB-L (SEQ ID NO:16) and 4-1BB (SEQ ID NO:18) polypeptide sequences that retain biological activity. Biological activity, in this instance, is the capacity to bind its cognate partner.

This invention additionally provides for the use of 4-1BB antagonists in the manufacture of a medicament for the treatment of cardiovascular disease. This invention further provides for the use of polynucleotides encoding 4-1BB antagonists in the manufacture of a medicament for the treatment of cardiovascular disease.

D. CD30 Antagonists

Further embodiments of the present invention provide compositions and methods for the treatment of cardiovascular disease comprising one or more CD30 antagonists. A CD30 antagonist is defined herein as an entity that is capable of reducing the effective amount of endogenous CD30 ligand (CD30-L), by either partially or completely blocking the interaction of CD30-L and CD30 and thereby inhibiting CD30-mediated signaling via membrane-bound CD30, as well as partially or completely inhibiting the subsequent biological activity of activating CD30. A CD30 antagonist may bind to either CD30-L or CD30.

The biological activity of CD30:CD30-L includes, but is not limited to, binding of CD30-L to CD30 and activation of CD30; intracellular activation of NF-κB, cytokine release and/or proliferation of CD30+ cells; proliferation of T-cells in the presence of an anti-CD3 co-stimulus.

Such CD30 antagonists include, but are not limited to: soluble forms of CD30-L and CD30; fragments of CD30-L that bind CD30 and inhibit binding of CD30-L without activating membrane-bound CD30; fragments of CD30 that bind CD30-L and inhibit binding of CD30-L to CD30; antibodies, fusion proteins and/or peptibodies directed against CD30-L that specifically bind CD30-L and partially or completely inhibit binding of CD30-L to CD30; antibodies, fusion proteins and/or peptibodies directed against CD30 that specifically bind CD30 and inhibit binding of CD30-L without themselves activating the CD30; small molecules that bind CD30-L or CD30 and inhibit the interaction thereof, such as CD30-L and/or CD30 peptidomimetics and/or mimotopes. As used herein, when reference is made to CD30 antagonists based on CD30-L or CD30, it is understood that the terms CD30-L and CD30 also encompass fragments, variants, muteins, derivatives and fusion proteins thereof, as described in detail below.

CD30 antagonists may comprise or be developed from CD30-L polynucleotide and polypeptide sequences. The isolation, cloning, preparation and characterization of human CD30-L is described in U.S. Pat. No. 5,480,981, which is incorporated herein by reference in its entirety. As mentioned above, embodiments of the present invention include anti-CD30-L antibodies as CD30 antagonists. Examples of antibodies that are directed against CD30-L that may be used to treat cardiovascular disease are described in U.S. Pat. No. 5,677,430, which is incorporated by reference in its entirety.

The term "CD30-L" as used herein refers to a genus of polypeptides which are capable of binding CD30. As used herein, the term "CD30-L" includes membrane-bound proteins (comprising a cytoplasmic domain, a transmembrane region, and an extracellular domain) as well as truncated proteins that retain the CD30-binding property. Such truncated proteins include, for example, soluble CD30-L comprising only the extracellular (receptor binding) domain. CD30-L is expressed on monocytes/macrophages, granulocytes, a subset of B cells and on activated but not resting T cells. By binding with cell-surface CD30, CD30-L can induce murine B cell differentiation and can induce the proliferation of activated T cells in the presence of an anti-CD3 co-stimulus (see, for example, Smith et al., *Cell* 73:1349-1360 (1993)). Moreover, CD30-L exhibits "reverse signaling," that is, the cell surface CD30-L that is expressed on neutrophils and peripheral blood T cells can be activated by cross-linking to stimulate metabolic activities in those cells (Wiley et al., *J Immunol* 157: 3235-39 (1996)).

CD30-L proteins of the present invention include, but are not limited to, human CD30-L comprising amino acids 1-215 of SEQ ID NO:20 or 1-234 of SEQ ID NO:22; and proteins that comprise N-terminal, C-terminal, or internal truncations of the foregoing sequences, but retain the desired biological activity. Examples include human CD30-L proteins comprising amino acids y to 234 of SEQ ID NO:22 wherein y is 1-19 (i.e., the N-terminal amino acid is any one of amino acids 1-19 of SEQ ID NO:22, and amino acid 234 is the C-terminal amino acid. Such proteins, truncated at the N-terminus, are capable of binding CD30.

Alternative embodiments provide soluble CD30-L polypeptides. Soluble CD30-L polypeptides comprise all or part of the extracellular domain of a native CD30-L but lack the transmembrane region that would cause retention of the polypeptide on a cell membrane. Since the CD30-L protein lacks a signal peptide, a heterologous signal peptide may be fused to the N-terminus of a soluble CD30-L protein to promote secretion thereof. The signal peptide is cleaved from the CD30-L protein upon secretion from the host cell. The soluble CD30-L polypeptides retain the ability to bind the CD30 receptor. Soluble CD30-L may also include part of the transmembrane region or part of the cytoplasmic domain or other sequences, provided that the soluble CD30-L protein is capable of being secreted.

Examples of soluble CD30-L polypeptides include those comprising the entire extracellular domain of a native CD30-L protein or a fragment of said extracellular domain that is capable of binding CD30. One such soluble CD30-L polypeptides comprise amino acids z to 215 (Asp) of the human CD30-L sequence of SEQ ID NO:20, wherein z is 44, 45, 46, or 47. In other words, the N-terminal amino acid of the soluble human CD30-L is selected from the amino acids in positions 44-47 of SEQ ID NO:20. DNA sequences encoding such soluble human CD30-L polypeptides include, but are not limited to, DNA sequences comprising a nucleotide sequence selected from the group consisting of nucleotides 130-645, 133-645, 136-645, and 139-645 of SEQ ID NO:19. Such sequences encode polypeptides comprising amino acids 44-215, 45-215, 46-215, and 47-215, respectively, of SEQ ID NO:20. Production of one such soluble human CD30-L protein, in the form of a fusion protein comprising amino acids 47-215 of SEQ ID NO:20 and an antibody Fc polypeptide, is illustrated in Example 11 of U.S. Pat. No. 5,480,981.

CD30 antagonists may comprise or be developed from CD30 polypeptide and/or polynucleotide sequences. Cloning and expression of a gene encoding CD30 has been reported and CD30 has been characterized as a transmembrane protein that possesses substantial homology to the nerve growth factor receptor superfamily (Durkop et al., *Cell* 1992, 68:421). The CD30 polynucleotide sequence reported in Durkop et al. supra is presented in SEQ ID NO:23, and the amino acid sequence encoded thereby is presented in SEQ ID NO:24. The extracellular portion of human CD30 corresponds to amino acids 1-390, or if the signal peptide is removed, to amino acids 19-390 of SEQ ID NO:24. The transmembrane region comprises amino acids 391-407 of SEQ ID NO:24. The phrase "soluble CD30" (sCD30) refers to soluble molecules that comprise all or part of the extracellular domain of the CD30 protein, and that retain the capacity to bind specifically with CD30-L. The polynucleotide and polypeptide sequences, as well as a description of how to make a CD30-Fc fusion protein, which may serve as a CD30 antagonist for the treatment of cardiovascular disease, is described in detail in U.S. Pat. No. 5,480,981, which is incorporated herein by reference in its entirety.

In further embodiments, CD30 antagonists are polypeptide mimetics, such as, but not limited to peptidomimetics, peptibodies and/or mimotopes developed from the polypeptide sequence of CD30-L (SEQ ID NOs:20 and/or 22) and/or CD30 (SEQ ID NO:24). Polypeptide mimetics may be developed through techniques known in the art, such as combinatorial peptide libraries. Polypeptide mimetics are peptide-containing molecules which mimic elements of protein secondary structure. A CD30-L polypeptide mimetic based on the amino acid sequence of CD30-L will bind to CD30 without activating CD30 and sterically hinder binding of endogenous CD30-L. A CD30 receptor polypeptide mimetic based on the amino acid sequence of CD30 receptor will bind to CD30-L and sterically hinder binding of endogenous CD30-L to CD30. CD30-L and CD30 peptide mimetics can be used to antagonize CD30-L binding to CD30 in a subject and thereby reduce the proinflammatory effects of CD30-L. As such, CD30 antagonists in the form of polypeptide mimetics may be used to treat inflammatory and/or immunoregulatory processes associated with cardiovascular disease.

Other forms of CD30-L and CD30 that are useful in the present invention include muteins and variants (also referred to as analogs), such as naturally occurring variants, that are substantially homologous to the native CD30-L (SEQ ID NOs:20 and/or 22) or CD30 (SEQ ID NO:24) polypeptide sequences and as described in U.S. Pat. No. 5,480,981 that retain biological activity.

This invention additionally provides for the use of CD30 antagonists in the manufacture of a medicament for the treatment of cardiovascular disease. This invention further provides for the use of polynucleotides encoding CD30 antagonists in the manufacture of a medicament for the treatment of cardiovascular disease.

E. OX40 Antagonists

Further embodiments of the present invention provide compositions and methods for the treatment of cardiovascular disease comprising one or more OX40 antagonists. A OX40 antagonist is defined herein as an entity that is capable of reducing the effective amount of endogenous OX40 ligand (OX40-L), by either partially or completely blocking the interaction of OX40-L and OX40 and thereby inhibiting OX40-mediated signaling via membrane-bound OX40, as well as partially or completely inhibiting the subsequent biological activity of activating OX40. A OX40 antagonist may bind to either OX40-L or OX40.

OX40:OX40-L biological activity, is defined herein as including, but is not limted to, binding of OX40-L to OX40 and activation of OX40; costimulatory activity on T lymphocytes; cytokine production, including IL-4; promoting the survival and proliferation of CD4+T cells; prolongation of immune responses; enhancing effector and memory-effector T cell fucntion by upregulating IL-2 production and increasing the life-span of effector T cells; and, enhanced tumor-specific immunity.

Such OX40 antagonists include, but are not limited to: soluble forms of OX40-L and OX40; fragments of OX40-L that bind OX40 and inhibit binding of OX40-L without activating membrane-bound OX40; fragments of OX40 that bind OX40-L and inhibit binding of OX40-L to OX40; antibodies, fusion proteins and/or peptibodies directed against OX40-L that specifically bind OX40-L and partially or completely inhibit binding of OX40-L to OX40; antibodies, fusion proteins and/or peptibodies directed against OX40 that specifically bind OX40 and inhibit binding of OX40-L without themselves activating the OX40; small molecules that bind OX40-L or OX40 and inhibit the interaction thereof, such as OX40-L and/or OX40 peptidomimetics and/or mimotopes. As used herein, when reference is made to OX40 antagonists based on OX40-L or OX40, it is understood that the terms OX40-L and OX40 also encompass fragments, variants, muteins, derivatives and fusion proteins thereof, as described in detail below.

OX40 antagonists may comprise or be developed from OX40 polynucleotide and polypeptide sequences. The OX-40 receptor, also referred to as OX40, ACT-4 and ACT35, is a protein expressed on the surface of antigen-activated mammalian CD4+ T-cells. DNA sequences encoding mouse, rat and human OX-40 receptor homologs have been cloned and sequenced (see, Mallet, et al., *EMBO*, 9:1063-1068 (1990); Calderhead, et al., *J Immunol*, 151:5261-5271 (1993); Latza, et al., *Eur. J. Immunol.* 24:677-683 (1994); and WO 95/12673). The isolation, cloning, and characterization of human OX40 is described in U.S. Pat. Nos. 5,821,332 and 6,277,962 B1, which are incorporated herein by reference in their entirety. As mentioned above, embodiments of the present invention include anti-OX40 antibodies as OX40 antagonists. Examples of antibodies that are directed against OX40 are described in U.S. Pat. Nos. 5,821,332 and 6,277, 962 B1.

OX40 proteins of the present invention include, but are not limited to, human OX40 comprising amino acids 1-277 of SEQ ID NO:28; and proteins that comprise N-terminal, C-terminal, or internal truncations of the foregoing sequences, but retain the desired biological activity. DNA sequences encoding such human OX40 polypeptides include, but are not limited to, DNA sequences comprising the nucleotide sequence of SEQ ID NO:27.

Alternative embodiments provide soluble OX40 polypeptides. Soluble OX40 polypeptides comprise all or part of the extracellular domain of a native OX40 but lack the transmembrane region that would cause retention of the polypeptide on a cell membrane. The soluble OX40 polypeptides retain the ability to bind the OX40-L. Soluble OX40 polypeptides may also include part of the transmembrane region or part of the cytoplasmic domain or other sequences, provided that the soluble OX40 protein is capable of being secreted. The putative signal sequence is from amino acids 1-22 or 1-24 and the extracellular domain spanning amino acids 23-212 or 24-212 or 24-212 and the transmembrane sequence spanning amino acids 213-240 of SEQ ID NO:28.

Examples of soluble OX40 polypeptides include those comprising the entire extracellular domain of a native OX40 protein or a fragment of said extracellular domain that is capable of binding OX40-L. One such soluble OX40-L polypeptides comprise amino acids z to 213 SEQ ID NO:28, wherein z is 22, 23, 24, or 25. In other words, the N-terminal amino acid of the soluble human OX40-L is selected from the amino acids in positions 22-25 of SEQ ID NO:28.

OX40 antagonists may comprise or be developed from OX40-L polynucleotide and polypeptide sequences. The isolation, cloning, preparation and characterization of human OX40-L is described in U.S. Pat. Nos. 6,156,878 and 6,242,566 B1, as well as U.S. Application Serial Nos: US 2001/0044523 A1 and US 2002/0077460 A1, which are incorported herein by reference in their entirety. As mentioned above, embodiments of the present invention include anti-OX40-L antibodies as OX40 antagonists. Examples of antibodies that are directed against OX40-L are described in U.S. Pat. Nos. 6,156,878 and 6,242,566 B1, as well as U.S. Application Serial Nos: US 2001/0044523 A1 and US 2002/0077460 A1.

OX40-L is also referred to as gp34 or ACT-4-L and is expressed on the surface of select mammalian cells, such as antigen presenting cells. Human OX40-L was initially isolated and described in Miura et al., *Mol Cell Biol* 11(3):1313-1325 (1991). U.S. Pat. No. 5,457, which is incorporated by reference in its entirety, describes the murine homologue of OX40-L.

OX40-L proteins of the present invention include, but are not limited to, human OX40-L polypeptides comprising amino acids 1-183 of SEQ ID NO:26 and polypeptides that comprise N-terminal, C-terminal, or internal truncations of the foregoing sequences, but retain the desired biological activity. DNA sequences encoding such human OX40 polypeptides include, but are not limited to, DNA sequences comprising the nucleotide sequence of SEQ ID NO:25.

Alternative embodiments provide soluble OX40-L polypeptides. Soluble OX40-L polypeptides comprise all or part of the extracellular domain of a native OX40 but lack the transmembrane region that would cause retention of the polypeptide on a cell membrane. The soluble OX40-L polypeptides retain the ability to bind the OX40. Soluble OX40-L polypeptides may also include part of the transmembrane region or part of the cytoplasmic domain or other sequences, provided that the soluble OX40-L protein is capable of being secreted.

In further embodiments, OX40 antagonists are polypeptide mimetics, such as, but not limited to peptidomimetics, peptibodies and/or mimotopes developed from the polypeptide sequence of OX40-L (SEQ ID NO:26) and/or OX40 (SEQ ID NO:28). Polypeptide mimetics may be developed through techniques known in the art, such as combinatorial peptide libraries. Polypeptide mimetics are peptide-containing molecules which mimic elements of protein secondary structure. A OX40-L polypeptide mimetic based on the amino acid sequence of OX40-L will bind to OX40 without activating OX40 and sterically hinder binding of endogenous OX40-L. A OX40 receptor polypeptide mimetic based on the amino acid sequence of OX40 receptor will bind to OX40-L and sterically hinder binding of endogenous OX40-L to OX40. OX40-L and OX40 peptide mimetics can be used to antagonize OX40-L binding to OX40 in a subject and thereby reduce the proinflammatory effects of OX40-L. As such, OX40 antagonists in the form of polypeptide mimetics may be used to treat inflammatory and/or immunoregulatory processes associated with cardiovascular disease.

Other forms of OX40-L and OX40 that are useful in the present invention include muteins and variants (also referred to as analogs), such as naturally occurring variants, that are substantially homologous to the native OX40-L (SEQ ID NO:26) or OX40 (SEQ ID NO:28) polypeptide sequences that retain biological activity.

This invention additionally provides for the use of OX40 antagonists in the manufacture of a medicament for the treatment of cardiovascular disease. This invention further provides for the use of polynucleotides encoding OX40 antagonists in the manufacture of a medicament for the treatment of cardiovascular disease.

F. CD39

Alternative embodiments of the invention are directed to treating cardiovascular disease in a subject having cardiovascular disease comprising administering soluble CD39 polypeptides in combination with one or more IL-17 antagonists, IL-18 antagonists, 4-1BB antagonists, CD30 antagonists and/or OX40 antagonists.

The molecular cloning and structural characterization of CD39 is presented in Maliszewski et al. (*J. Immunol.* 153:3574, 1994). A cDNA encoding the cell-surface molecule CD39 has been isolated, cloned and sequenced, as described in U.S. patent application Ser. No. 09/835,147, as well as WO 00/23459, which are incorporated by reference in their entirety. The nucleic acid sequence and predicted amino acid sequence are shown in SEQ ID NO:29 and SEQ ID NO:30, respectively.

The present invention provides methods of using soluble forms of CD39 to treat cardiovascular disease, which were constructed by removing the amino- and carboxy-terminal transmembrane domains. Soluble CD39 retains the capacity of wildtype CD39 to metabolize ATP and ADP at physiologically relevant concentrations as well as the ability to block and reverse ADP-induced platelet activation and recruitment, including platelet aggregation. The use of soluble forms of CD39 is advantageous because purification of the polypeptides from recombinant host cells is facilitated, and because soluble polypeptides are generally more suitable than membrane-bound forms for clinical administration. Because CD39 inhibits platelet activation and recruitment, and therefore platelet aggregation, the present invention provides methods and compositions for inhibiting formation of a thrombus at a site in a mammal at which platelets are inappropriately activated, methods for use in controlling platelet reactivity, thereby regulating the hemostatic and thrombotic processes, and methods of inhibiting and/or reversing platelet aggregation.

CD39 contains two putative transmembrane regions, near the amino and carboxy termini, which may serve to anchor the native protein in the cell membrane. The portion of the molecule between the transmembrane regions is external to the cell. As used herein, the term "CD39 polypeptides" includes CD39, homologs of CD39, variants, fragments, and derivatives of CD39, fusion polypeptides comprising CD39, and soluble forms of CD39 polypeptides. The CD39 gene family is reported to contain at least four human members: CD39, CD39L2, CD39L3, and CD39L4 (Chadwick and Frischauf, *Genomics* 50:357, 1998). CD39-L4 is reported to be a secreted apyrase (Mulero et al., *J. Biol. Chem.* 274(29):20064, 1999). Additional solCD39 variants have been constructed by fusing N-terminal sequences from CD39L2, CD39L3, or CD39L4 to a soluble portion of CD39, as described in detail in U.S. patent application Ser. No. 09/835,147.

CD39 is an ecto-ADPase (apyrase) located on the surface of endothelial cells. This enzyme is mainly responsible for the maintenance of blood fluidity, thus maintaining platelets in the baseline (resting) state. This is accomplished by metabolism of the major platelet agonist, adenosine diphosphate, to adenosine monophosphate, which is not an agonist. Because ADP is the most important agonist of platelet aggregation, and is present in platelet releasate, a substance which catabolizes ADP is useful in treating or preventing disease states that involve inappropriate aggregation of platelets.

Apyrase activity resides in the extracellular domain of CD39. Thus, CD39 polypeptides include soluble forms of CD39 such as those having an amino terminus selected from the group consisting of amino acids 36-44 of SEQ ID NO:30, and a carboxy terminus selected from the group consisting of amino acids 471-478 of SEQ ID NO:30, and which exhibit CD39 biological activity. Soluble CD39 polypeptides also include those polypeptides which include part of either or both of the transmembrane regions, provided that the soluble CD39 polypeptide is capable of being secreted from a cell, and retains CD39 biological activity. Soluble CD39 polypeptides further include oligomers or fusion polypeptides comprising the extracellular portion of CD39, and fragments of any of these polypeptides that have biological activity.

The term "biological activity," with regards to CD39, includes apyrase enzymatic activity as well as the ex vivo and in vivo activities of CD39. Apyrases catalyze the hydrolysis of nucleoside tri- and/or di- phosphates, but a given apyrase may display different relative specificities for either nucleoside triphosphates or nucleoside diphosphates. Biological activity of soluble forms of CD39 may be determined, for example, in an ectonucleotidase or apyrase assay (e.g. ATPase or ADPase assays), or in an assay that measures inhibition of platelet aggregation. Exemplary assays are disclosed herein; those of skill in the art will appreciate that other, similar types of assays can be used to measure biological activity.

In further embodiments, CD39 compositions for the treatment of cardiovascular disease comprise polypeptide mimetics, such as, but not limited to peptidomimetics, peptibodies and/or mimotopes developed from the polypeptide sequence of CD39 (SEQ ID NO:30). Polypeptide mimetics may be developed through techniques known in the art, such as combinatorial peptide libraries. Polypeptide mimetics are peptide-containing molecules which mimic elements of protein secondary structure. A CD39 polypeptide mimetic based on the amino acid sequence of CD39 will catalyze the hydrolysis of nucleoside tri- and/or di- phosphates. As such, CD39 antagonists in the form of polypeptide mimetics may be used to treat cardiovascular disease.

Other forms of CD39 that are useful in the present invention include muteins and variants (also referred to as analogs), such as naturally occurring variants, that are substantially homologous to the native CD39 (SEQ ID NO:30) polypeptide sequences and as described in U.S. patent application Ser. No. 09/835,147 that retain biological activity.

This invention additionally provides for the use of CD39 in the manufacture of a medicament for the treatment of cardiovascular disease. This invention further provides for the use of polynucleotides encoding CD39 in the manufacture of a medicament for the treatment of cardiovascular disease.

CD39, in all its forms as described herein and in U.S. patent application Ser. No. 09/835,147, may be used in combination with one or more IL-17, IL-18, 4-1BB, CD30 and/or OX40 antagonist in the treatment of cardiovascular disease.

G. Further Embodiments of IL-17, IL-18, 4-1BB, CD30 AND OX40 Antagonists and CD39

Other forms of the IL-17, IL-17R, IL-18, IL-18R, IL-18BP, 4-1BB, 4-1BB-L, CD30, CD30-L, OX40, OX40-L and CD39 that are useful in the present invention include muteins and variants (also referred to as analogs), such as naturally occurring variants, that are substantially homologous to the native sequences provided herein, as well as the sequences provided in the patents incorporated by reference.

Substantially homologous means a variant amino acid sequence that is at least 75%, at least 80%, at least 85%, at least 90%, at least 95%, at least 96%, at least 97%, at least 98% or at least 99% identical to the native amino acid sequences, as disclosed above. The percent identity of two amino acid or two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., 1984, *Nuci. Acids Res.* 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, *Nuci. Acids Res.* 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.0.9, available for use via the National Library of Medicine website www.ncbi.nlm.nih.gov/gorf/wblast2.cgi, or the UW-BLAST 2.0 algorithm. Standard default parameter settings for UW-BLAST 2.0 are described at the following Internet site: sapiens.wustl.edu/blast/blast/#Features. In addition, the BLAST algorithm uses the BLOSUM62 amino acid scoring matix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, *Methods Enzymol.* 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

Such variants include polypeptides that are substantially homologous to native IL-17, IL-17R, IL-18, IL-18R, IL-18BP, 4-1BB, 4-1BB-L, CD30, CD30-L, OX40, OX40-L and CD39 sequences, but which have an amino acid sequence different from that of a native IL-17 receptor because of one or more deletions, insertions or substitutions. Particular embodiments include, but are not limited to, IL-17, IL-17R, IL-18, IL-18R, IL-18BP, 4-1BB, 4-1BB-L, CD30, CD30-L, OX40, OX40-L and CD39 polypeptides that comprise at least one conservative amino acid substitution. Alternative embodiments comprise IL-17, IL-17R, IL-18, IL-18R, IL-18BP, 4-1BB, 4-1BB-L, CD30, CD30-L, OX40, OX40-L and CD39 polypeptides comprising from one to ten deletions, insertions or substitutions of amino acid residues, when compared to a native sequences. The IL-17, IL-17R, IL-18, IL-18R, IL-18BP, 4-1BB, 4-1BB-L, CD30, CD30-L, OX40, OX40-L and CD39-encoding polynucleotides of the present invention include variants that differ from a native IL-17, IL-17R, IL-18, IL-18R, IL-18BP, 4-1BB, 4-1BB-L, CD30, CD30-L, OX40, OX40-L and CD39 polynucleotide sequence because of one or more deletions, insertions or substitutions, but that encode a biologically active polypeptide. Included as variants of IL-17, IL-17R, IL-18, IL-18R, IL-18BP, 4-1BB, 4-1BB-L, CD30, CD30-L, OX40, OX40-L and CD39 polypeptides are those variants that are naturally occurring, such as allelic forms and alternatively spliced forms, as well as variants that have been constructed by modifying the amino acid sequence of an IL-17, IL-17R, IL-18, IL-18R, IL-18BP, 4-1BB, 4-1BB-L, CD30, CD30-L, OX40, OX40-L and CD39 polypeptide or the nucleotide sequence of a nucleic acid encoding an IL-17, IL-17R, IL-18, IL-18R, IL-18BP, 4-1BB, 4-1BB-L, CD30, CD30-L, OX40, OX40-L and CD39 polypeptide.

As mentioned above, IL-17, IL-17R, IL-18, IL-18R, IL-18BP, 4-1BB, 4-1BB-L, CD30, CD30-L, OX40, OX40-L and CD39 variants may comprise a sequence having at least one conservatively substituted amino acid, meaning that a given amino acid residue is replaced by a residue having similar physiochemical characteristics. Alternative embodiments comprise IL-17, IL-17R, IL-18, IL-18R, IL-18BP, 4-1BB, 4-1BB-L, CD30, CD30-L, OX40, OX40-L and CD39 variants that comprise between 1-10, 1-20 or 1-30 conservatively substituted sequences. Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of IL-17, IL-17R, IL-18, IL-18R, IL-18BP, 4-1BB, 4-1BB-L, CD30, CD30-L, OX40, OX40-L or CD39. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events or from proteolytic cleavage of the native protein, wherein the native biological property is retained.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, *Acta Physiol. Scand. Suppl.* 643:55-67; Sasaki et al., 1998, *Adv. Biophys.* 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 1.

TABLE 1

Amino Acid Substitutions

| Original Residues | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

As noted above, naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. (Kyte, et al., *J. Mol. Biol.,* 157: 105-131 (1982)). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e.,. with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in the foregoing sequences using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, Moult J., Curr. Op. in Biotech., 7(4): 422-427 (1996), Chou et al., Biochemistry, 13(2): 222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47: 251-276 and Chou et al., Biophys. J., 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm, et al., Nuci. Acid. Res., 27(1): 244-247 (1999). It has been suggested (Brenner et al., Curr. Op. Struct. Biol., 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377-87 (1997); Sippl, et al., Structure, 4(1): 15-9 (1996)), "profile analysis" (Bowie, et al., Science, 253: 164-170 (1991); Gribskov, et al., Meth. Enzym., 183: 146-159 (1990); Gribskov, et al., Proc. Nat. Acad. Sci., 84(13): 4355-8 (1987)), and "evolutionary linkage" (See Holm, supra, and Brenner,. supra).

Embodiments of IL-17, IL-17R, IL-18, IL-18R, IL-18BP, 4-1BB, 4-1BB-L, CD30, CD30-L, OX40, OX40-L and CD39 variants include IL-17, IL-17R, IL-18, IL-18R, IL-18BP, 4-1BB, 4-1BB-L, CD30, CD30-L, OX40, OX40-L and CD39 variants include polypeptide sequences that are at least about 75%, 80%, 85%, 90%, 95%, 96%, 97%, 98% or 99% identical in amino acid sequence to the respective amino acid sequence for IL-17, IL-17R, IL-18, IL-18R, IL-18BP, 4-1BB, 4-1BB-L, CD30, CD30-L, OX40, OX40-L and CD39, as described above.

Further modifications in the IL-17, IL-17R, IL-18, IL-18R, IL-18BP, 4-1BB, 4-1BB-L, CD30, CD30-L, OX40, OX40-L and CD39 polypeptide or IL-17, IL-17R, IL-18, IL-18R, IL-18BP, 4-1BB, 4-1BB-L, CD30, CD30-L, OX40, OX40-L and CD39 polynucleotide sequences can be made by those skilled in the art using known techniques. Modifications of interest in the polypeptide sequences can include the alteration, substitution, replacement, insertion or deletion of a selected amino acid. For example, one or more of the cysteine residues can be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the IL-17, IL-17R, IL-18, IL-18R, IL-18BP, 4-1BB, 4-1BB-L, CD30, CD30-L, OX40, OX40-L and CD39 extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Procedures for inactivating N-glycosylation sites in polypeptides are known in the art and include, for example, those described in U.S. Pat. No. 5,071,972. Additional variants within the scope of the invention include IL-17, IL-17R, IL-18, IL-18R, IL-18BP, 4-1BB, 4-1BB-L, CD30, CD30-L, OX40, OX40-L and CD39 polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Preferably, such alteration, substitution, replacement, insertion or deletion does not diminish the biological activity of IL-17, IL-17R, IL-18, IL-18R, IL-18BP, 4-1BB, 4-1BB-L, CD30, CD30-L, OX40, OX40-L or CD39. One example is a variant that binds with essentially the same binding affinity as does the native form. Binding affinity can be measured by conventional procedures, e.g., as described in U.S. Pat. No. 5,512,457 and as set forth herein. Furthermore, IL-17, IL-17R, IL-18, IL-18R, IL-18BP, 4-1BB, 4-1BB-L, CD30, CD30-L, OX40, OX40-L and CD39 molecules may be modified by the addition of one or more water-soluble polymers, such as, but not limited to, polyethylene glycol to increase bio-availability and/or pharmacokinetic half-life.

Various means for attaching chemical moieties useful for increase bio-availability and/or pharmacokinetic half-life are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer which may be used for protein modification. Dextrans are polysaccharide polymers comprised of individual subunits of glucose predominantly linked by al-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference in its entirety. Dextran of about 1 kD to about 20 kD is preferred when dextran is used as a vehicle in accordance with the present invention.

Additional IL-17, IL-17R, IL-18, IL-18R, IL-18BP, 4-1BB, 4-1BB-L, CD30, CD30-L, OX40, OX40-L and CD39 derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., Bio/Technology 6:1204, 1988. One such peptide is the FLAG® octapeptide (SEQ ID NO:31), which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Additional embodiments of IL-17, IL-17R, IL-18, IL-18R, IL-18BP, 4-1BB, 4-1BB-L, CD30, CD30-L, OX40, OX40-L and CD39 that may be used in the methods described herein include oligomers or fusion polypeptides that contain IL-17, IL-17R, IL-18, IL-18R, IL-18BP, 4-1BB, 4-1BB-L, CD30, CD30-L, OX40, OX40-L and/or CD39 polypeptide, one or more fragments of IL-17, IL-17R, IL-18, IL-18R, IL-18BP, 4-1BB, 4-1BB-L, CD30, CD30-L, OX40, OX40-L and/or CD39, or any of the derivative or variant forms of IL-17, IL-17R, IL-18, IL-18R, IL-18BP, 4-1BB, 4-1BB-L, CD30, CD30-L, OX40, OX40-L and/or CD39 as disclosed herein, as well as in the U.S. patents listed above. In particular embodiments, the oligomers comprise soluble IL-17, IL-17R, IL-18, IL-18R, IL-18BP, 4-1BB, 4-1BB-L, CD30, CD30-L, OX40, OX40-L and/or CD39 polypeptides. Oligomers can be in the form of covalently linked or non-covalently-linked multimers, including dimers, trimers, or higher oligomers. In alternative embodiments, IL-17, IL-17R, IL-18, IL-18R, IL-18BP, 4-1BB, 4-1BB-L, CD30, CD30-L, OX40, OX40-L and CD39 oligomers comprise multiple IL-17, IL-17R, IL-18, IL-18R, IL-18BP, 4-1BB, 4-1BB-L, CD30, CD30-L, OX40, OX40-L and CD39 polypeptides joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

Immunoglobulin-based Oligomers. Suitable forms of IL-17, IL-17R, IL-18, IL-18R, IL-18BP, 4-1BB, 4-1BB-L, CD30, CD30-L, OX40, OX40-L and CD39 antagonists include chimeric proteins which include a second polypeptide that may promote the spontaneous formation by the chimeric protein of a dimer, trimer or higher order multimer that is capable of binding their respective cognates and thereby inhibiting or reducing the effects of inflammation and symptoms of cardiovascular disease. Chimeric proteins used as antagonists may be proteins that contain portions of an antibody molecule and a soluble polypeptide from IL-17, IL-17R, IL-18, IL-18R, IL-18BP, 4-1BB, 4-1BB-L, CD30, CD30-L, OX40, OX40-L and/or CD39. Suitable fusion proteins include an IL-17, IL-17R, IL-18, IL-18R, IL-18BP, 4-1BB, 4-1BB-L, CD30, CD30-L, OX40, OX40-L and CD39 polypeptide, e.g. the extracellular domain, or a fragment of the extracellular domain, linked to an immunoglobulin Fc region. Fragments of a Fc region may also be used, as well as Fc muteins that exhibit decreased affinity for Fc receptors. Soluble IL-17, IL-17R, IL-18, IL-18R, IL-18BP, 4-1BB, 4-1BB-L, CD30, CD30-L, OX40, OX40-L and CD39, as well as fragments thereof, can be fused directly or through linker sequences to the Fc portion of an immunoglobulin.

One embodiment of IL-17, IL-17R, IL-18, IL-18R, IL-18BP, 4-1BB, 4-1BB-L, CD30, CD30-L, OX40, OX40-L and CD39 antagonist is directed to a dimer comprising two fusion polypeptides created by fusing an IL-17, IL-17R, IL-18, IL-18R, IL-18BP, 4-1BB, 4-1BB-L, CD30, CD30-L, OX40, OX40-L and/or CD39 polypeptide to a Fc polypeptide derived from an antibody. A gene fusion encoding such a fusion polypeptide is inserted into an appropriate expression vector. IL-17, IL-17R, IL-18, IL-18R, IL-18BP, 4-1BB, 4-1BB-L, CD30, CD30-L, OX40, OX40-L and CD39-Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151, is a single chain polypeptide extending from the N-terminal hinge region to the native C-terminus of the Fc region of a human IgG1 antibody. For a bivalent form of IL-17, IL-17R, IL-18, IL-18R, IL-18BP, 4-1BB, 4-1BB-L, CD30, CD30-L, OX40, OX40-L or CD39, such a fusion could be to the Fc portion of an IgG molecule. Other immunoglobulin isotypes can also be used to generate such fusions. For example, a polypeptide-IgM fusion would generate a decavalent form of the polypeptide of the invention.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred Fc polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) are known in the art and have been described, e.g., by Ashkenazi et al. (*PNAS USA* 88:10535, 1991); Byrn et al. (Nature 344:677, 1990); and Hollenbaugh and Aruffo ("Construction of Immunoglobulin Fusion Polypeptides", in *Current Protocols in Immunology*, Suppl. 4, pages 10.19.1- 10.19.11, 1992). Another useful Fc polypeptide is the Fc mutein described in U.S. Pat. No. 5,457,035 and in Baum et al., (*EMBO J.* 13:3992-4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four IL-17R extracellular regions.

Peptide-linker Based Oligomers. Alternatively, the oligomer is a fusion polypeptide comprising multiple IL-17, IL-17R, IL-18, IL-18R, IL-18BP, 4-1BB, 4-1BB-L, CD30, CD30-L, OX40, OX40-L and/or CD39 polypeptides, with or without peptide linkers (spacer peptides). Among the suitable peptide linkers are those described in U.S. Pat. Nos. 4,751, 180 and 4,935,233. A DNA sequence encoding a desired peptide linker can be inserted between, and in the same reading frame as, the DNA sequences of the invention, using any suitable conventional technique. For example, a chemically synthesized oligonucleotide encoding the linker can be ligated between the sequences. In particular embodiments, a fusion polypeptide comprises from two to four soluble IL-17, IL-17R, IL-18, IL-18R, IL-18BP, 4-1BB, 4-1BB-L, CD30, CD30-L, OX40, OX40-L and/or CD39 polypeptides, separated by peptide linkers. Suitable peptide linkers, their combination with other polypeptides, and their use are well known by those skilled in the art.

Oligomeric forms of IL-17, IL-18, 4-1BB, CD30, OX40 and CD39 antagonists suitable for use in treating cardiovascular disease also include an IL-17, IL-17R, IL-18, IL-18R, IL-18BP, 4-1BB, 4-1BB-L, CD30, CD30-L, OX40, OX40-L and/or CD39 polypeptide, the extracellular domain of an IL-17, IL-17R, IL-18, IL-18R, IL-18BP, 4-1BB, 4-1BB-L, CD30, CD30-L, OX40, OX40-L and/or CD39 polypeptide, or an IL-17, IL-17R, IL-18, IL-18R, IL-18BP, 4-1BB, 4-1BB-L, CD30, CD30-L, OX40, OX40-L and CD39 antagonistic fragment of the extracellular domain associated with a zipper domain, such as zipper proteins described in U.S. Pat. No. 5,716,805, the disclosure of which is incorporated by reference herein. Other Examples of zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., Science 245:646, 1989; Turner and Tjian, *Science* 243:1689, 1989), and the gene product of the murine proto-oncogene, c-myc (Landschulz et al., *Science* 240:1759, 1988). The fusogenic proteins of several different viruses, including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990). Leucine zipper domains are peptides that promote oligomerization of the polypeptides in which they are found. Leucine zippers were originally identified in several DNA-binding polypeptides and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

The present invention comprises fusion polypeptides with or without spacer amino acid linking groups. For example, two soluble IL-17, IL-17R, IL-18, IL-18R, IL-18BP, 4-1BB, 4-1BB-L, CD30, CD30-L, OX40, OX40-L and/or CD39 domains can be linked with a linker sequence, such as (Gly) 4Ser(Gly)$_5$Ser (SEQ ID NO:32), which is described in U.S. Pat. No. 5,073,627. Other linker sequences include, for example, GlyAlaGlyGlyAlaGlySer(Gly)$_5$Ser (SEQ ID NO:33), (Gly4Ser)2 (SEQ ID NO:34), (GlyThrPro)3 (SEQ ID NO:35), and (Gly4Ser)3Gly4SerGly$_5$Ser (SEQ ID NO:36).

Nucleic acid sequences encoding soluble IL-17, IL-17R, IL-18, IL-18R, IL-18BP, 4-1BB, 4-1BB-L, CD30, CD30-L, OX40, OX40-L and CD39 polypeptides having altered glycosylation sites, deleted or substituted Cys residues, or modified proteolytic cleavage sites, nucleic acid sequences encoding sub-units of IL-17, IL-17R, IL-18, IL-18R, IL-18BP, 4-1BB, 4-1BB-L, CD30, CD30-L, OX40, OX40-L and CD39 polypeptides or fusion polypeptides of IL-17, IL-17R, IL-18, IL-18R, IL-18BP, 4-1BB, 4-1BB-L, CD30, CD30-L, OX40, OX40-L and CD39 with other peptides, allelic variants of IL-17, IL-17R, IL-18, IL-18R, IL-18BP, 4-1BB, 4-1BB-L, CD30, CD30-L, OX40, OX40-L and CD39, mammalian homologs of IL-17, IL-17R, IL-18, IL-18R, IL-18BP, 4-1BB, 4-1BB-L, CD30, CD30-L, OX40, OX40-L and CD39, and nucleic acid sequences encoding IL-17, IL-17R, IL-18, IL-18R, IL-18BP, 4-1BB, 4-1BB-L, CD30, CD30-L, OX40, OX40-L and CD39 polypeptides derived from alternative mRNA constructs, or those that encode peptide having substituted or additional amino acids, are examples of nucleic acid sequences according to the invention.

Due to degeneracy of the genetic code, there can be considerable variation in nucleotide sequences encoding the same amino acid sequence. Embodiments include sequences capable of hybridizing under moderately stringent conditions. The basic parameters affecting the choice of hybridization conditions and guidance for devising suitable conditions are set forth by Sambrook-Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5 x SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6($\log_{10}$ [Na$^+$])+0.41(% G +C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 85%, at least 90%, at least 95%, at least 97.5%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

In alternative embodiments, IL-17, IL-17R, IL-18, IL-18R, IL-18BP, 4-1BB, 4-1BB-L, CD30, CD30-L, OX40, OX40-L and/or CD39 polynucleotides include those that encode polypeptides that are at least 75%, or at least 80%, or at least 85%, or at least 90%, or at least 95%, or at least 96%, or at least 97%, or at least 98%, or at least 99% identical in amino acid sequence to the amino acid sequence of native or at least 80% polypeptide sequences as set forth above and in the sequence listing. For polynucleotides that encode a fragment of IL-17, IL-17R, IL-18, IL-18R, IL-18BP, 4-1BB, 4-1BB-L, CD30, CD30-L, OX40, OX40-L and/or CD39, percent identity of the fragment is based on percent identity to the corresponding portion of full-length IL-17, IL-17R, IL-18, IL-18R, IL-18BP, 4-1BB, 4-1BB-L, CD30, CD30-L, OX40, OX40-L and/or CD39 polypeptide, respectively.

Mutations can be introduced into nucleic acids by synthesizing oligonucleotides containing a mutant sequence, flanked by restriction sites enabling ligation to fragments of the native sequence. Following ligation, the resulting reconstructed sequence encodes a variant having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12-19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Polynucleotide sequences that encode IL-17 receptor polypeptides comprising various additions or substitutions of amino acid residues or sequences, or deletions of terminal or internal residues or sequences not needed for biological activity can be prepared. For example, N-glycosylation sites can be modified to preclude glycosylation while allowing expression of a homogeneous, reduced carbohydrate variant using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain.

In another example, sequences encoding Cys residues can be altered to cause the Cys residues to be deleted or replaced with other amino acids, preventing formation of incorrect intramolecular disulfide bridges upon renaturation. Thus, Cys residues may be replaced with another amino acid or deleted without affecting polypeptide tertiary structure or disulfide bond formation.

Other approaches to mutagenesis involve modification of sequences encoding dibasic amino acid residues to enhance expression in yeast systems in which KEX2 protease activity is present. Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a polypeptide. KEX2 protease processing sites are inactivated by deleting, adding or substituting residues to alter Arg-Arg, Arg-Lys, and Lys-Arg pairs to eliminate the occurrence of these adjacent basic residues. Similar modification may be made to sequences encoding sites recognized and cleaved by other proteolytic enzymes. Sub-units of a IL-17, IL-17R, IL-18, IL-18R, IL-18BP, 4-1BB, 4-1BB-L, CD30, CD30-L, OX40, OX40-L and/or CD39 polypeptide may be constructed by deleting sequences encoding terminal or internal residues or sequences not necessary for biological activity. Sequences encoding fusion polypeptides as described below may be constructed by ligating sequences encoding additional amino acid residues to the inventive sequences without affecting biological activity.

Mutations in nucleotide sequences constructed for expression of a soluble IL-17, IL-17R, IL-18, IL-18R, IL-18BP, 4-1BB, 4-1BB-L, CD30, CD30-L, OX40, OX40-L and/or CD39 must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated polypeptides screened for the desired activity.

Not all mutations in the nucleotide sequence which encodes a IL-17, IL-17R, IL-18, IL-18R, IL-18BP, 4-1BB, 4-1BB-L, CD30, CD30-L, OX40, OX40-L and/or CD39 polypeptide will be expressed in the final product, for example, nucleotide substitutions may be made to enhance expression, primarily to avoid secondary structure loops in the transcribed mRNA or to provide codons that are more readily translated by the selected host, e.g., the well-known *E. coli* preference codons for *E. coli* expression.

In the genome, IL-17, IL-17R, IL-18, IL-18R, IL-18BP, 4-1BB, 4-1BB-L, CD30, CD30-L, OX40, OX40-L and/or CD39 polypeptides are encoded by multi-exon genes. The present invention further includes alternative mRNA constructs that can be attributed to different mRNA splicing events following transcription and which hybridize with the cDNAs disclosed herein under conditions of moderate stringency, as defined above.

H. Antibodies as IL-17, IL-18, 4-1BB, CD30 and OX40 Antagonists.

IL-17, IL-18, 4-1BB, CD30 and OX40 antagonists include antibodies that specifically bind IL-17, IL-17R, IL-18, IL-18R, IL-18BP, 4-1BB, 4-1BB-L, CD30, CD30-L, OX40 or OX40-L. More specifically, IL-17 antagonists include antibodies directed against IL-17 that specifically bind IL-17 and partially or completely inhibit binding of IL-17 to IL-17 receptor, and antibodies directed against IL-17 receptor that specifically bind IL-17 receptor and inhibit binding of IL-17 without themselves activating the IL-17 receptor; IL-18 antagonists include antibodies directed against IL-18 that specifically bind IL-18 and partially or completely inhibit binding of IL-18 to IL-18R; antibodies directed against IL-18R that specifically bind IL-18R and inhibit receptor binding of IL-18 without themselves transducing a signal via IL-18R; 4-1BB antagonists include antibodies directed against 4-1BB that specifically bind 4-1BB and partially or completely inhibit binding of 4-1BB to 4-1BB-L; antibodies directed against 4-1BB that specifically bind 4-1BB and inhibit binding of 4-1BB-L without themselves transducing a signal via 4-1BB; CD30 antagonists include antibodies directed against CD30-L that specifically bind CD30-L and partially or completely inhibit binding of CD30-L to CD30; antibodies directed against CD30 that specifically bind CD30 and inhibit binding of CD30-L without themselves activating the CD30; and, OX40 antagonists include antibodies directed against OX40-L that specifically bind OX40-L and partially or completely inhibit binding of OX40-L to OX40; antibodies directed against OX40 that specifically bind OX40 and inhibit binding of OX40-L without themselves activating the OX40.

IL-17, IL-17R, IL-18, IL-18R, IL-18BP, 4-1BB, 4-1BB-L, CD30, CD30-L, OX40 or OX40-L, as well as fragments, variants, muteins, derivatives and fusion proteins thereof, as set forth above, can be employed as "immunogens" in producing antibodies that may be used in the diagnosis and treatment of cardiovascular disease. In making IL-17, IL-18, 4-1BB, CD30 and OX40 antagonists in the form of antibodies, when reference is made to IL-17, IL-17R, IL-18, IL-18R, IL-18BP, 4-1BB, 4-1BB-L, CD30, CD30-L, OX40 or OX40-L it is understood to also encompass fragments, variants, muteins, derivatives and fusion proteins thereof. A number of antibodies have been made to IL-17, IL-17R, IL-18, IL-18R, 4-1BB, 4-1BB-L, OX40, CD30, CD30-L and CD39, as shown in Table 3 of Example 6.

IL-17, IL-17R, IL-18, IL-18R, IL-18BP, 4-1BB, 4-1BB-L, CD30, CD30-L, OX40, OX40-L and CD39 contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Antibodies to IL-17, IL-17R, IL-18, IL-18R, IL-18BP, 4-1BB, 4-1BB-L, CD30, CD30-L, OX40, OX40-L and CD39 can conveniently be generated against a recombinantly produced form of the proteins described above and provided in the respective sequence identifier numbers. IL-17, IL-18, 4-1BB, CD30 and OX40 antagonists that are antibodies include but are not limited to polyclonal antibodies, monoclonal antibodies (mAbs), humanized or chimeric antibodies, single chain antibodies, Fab fragments, F(ab)$_2$ fragments, fragments produced by a Fab expression library, anti-idiotypic (anti-Id) antibodies, and epitope-binding fragments of any of the above. Such antibodies can be utilized in methods of treating cardiovascular disease.

Both polyclonal and monoclonal antibodies to IL-17, IL-17R, IL-18, IL-18R, IL-18BP, 4-1BB, 4-1BB-L, CD30, CD30-L, OX40, OX40-L and CD39 can be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., Immunology Today 4:72, 1983; Cole et al., Proc. Natl. Acad. Sci. USA 80:2026, 1983); and the EBV-hybridoma technique (Cole et al., 1985, Monoclonal Antibodies And Cancer Therapy, Alan R. Liss, Inc., pp. 77-96).

Methods of making humanized monoclonal antibodies are well known, and include for example those described in U.S. Pat. No. 5,585,089 (Protein Design: C L Queen et al.; "Humanized Immunoglobulins"), U.S. Pat. No. 5,565,332 ("Production of Chimeric Antibodies-A Combinatorial Approach"), U.S. Pat. No. 5,225,539 (Med Res Council: G P Winter; "Recombinant Altered Antibodies And Methods Of Making Altered Antibodies"), U.S. Pat. No. 5,693,761-762 (Protein Design: C L Queen et al.; "Polynucleotides Encoding Improved Humanized Immunoglobulins", and "Humanized Immunoglobulins"), and U.S. Pat. No. 5,530,101 (Protein Design: C L Queen et al.; "Humanized Immunoglobulins"), and references cited therein.

Hybridoma cell lines that produce monoclonal antibodies specific for IL-17, IL-17R, IL-18, IL-18R, IL-18BP, 4-1BB, 4-1BB-L, CD30, CD30-L, OX40, OX40-L and CD39 are contemplated herein. Such hybridomas can be produced and identified by conventional techniques. For the production of antibodies, various host animals may be immunized by injection with IL-17, IL-17R, IL-18, IL-18R, IL-18BP, 4-1BB, 4-1BB-L, CD30, CD30-L, OX40, OX40-L or CD39 polypeptide that is immunogenic. Such host animals may include, but are not limited to, horse, goat, sheep, cow, rabbits, mice, and rats, to name a few. Various adjuvants may be used to increase the immunological response. Depending on the host species, such adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof. The hybridoma producing the mAb may be cultivated in vitro or in vivo. Or, the antibody genes can be cloned and optionally otherwise altered, and expressed in another cell line approved for recombinant production of protein pharmaceuticals such as, for example, CHO cells.

Alternatively, libraries of antibody fragments can be screened and used to develop human antibodies through recombinant techniques. Such libraries are commercially available from, for example, Cambridge Antibody Technology (Melbourne, UK), and Morphosys (Munich, Del.).

In addition, techniques developed for the production of "chimeric antibodies" (Takeda et al., Nature, 314:452, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the invention also include humanized versions of murine monoclonal antibodies. Such humanized antibodies can be prepared by known techniques and offer the advantage of reduced immunogenicity when the antibodies are administered to humans. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some (preferably virtually all) antibodies produced by the animal upon immunization. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Procedures to generate antibodies transgenically can be found in GB 2,272,440, US Pat. Nos. 5,569,825 and 5,545,806 and related patents claiming priority therefrom, all of which are incorporated by reference herein. For use in humans, the antibodies are typically human or humanized; techniques for creating such human antibodies are also known. Transgenic animals for making human antibodies are available from, for example, Medarex Inc. (Princeton, N.J.) Protein Design Labs, Inc. (Fremont, Calif.) and Abgenix Inc. (Fremont, Calif.).

Expression of a humanized immunoglobulin sequences in bacterial hosts may be used to select higher affinity humanized immunoglobulin sequences by mutagenizing the CDR regions and producing bacteriophage display libraries which may be screened for humanized immunoglobulin CDR variants which possess high affinity and/or high specificity binding to IL-17, IL-17R, IL-18, IL-18R, IL-18BP, 4-1BB, 4-1BB-L, CD30, CD30-L, OX40, OX40-L or CD39. One potential advantage of such affinity sharpening is the generation of humanized immunoglobulin CDR variants that have improved binding affinity and/or reduced cross-reactivity with molecules other than the molecule to which they were raised. Methods for producing phage display libraries having immunoglobulin variable region sequences are provided in the art (see, e.g., Cesareni, FEBS Lett 307:66, 1992; Swimmer et al., Proc. Natl. Acad. Sci. USA 89:3756, 1992; Gram et al., Proc. Natl. Acad. Sci. USA 89:3576, 1992; Clackson et al., Nature 352:624, 1991; Scott & Smith, Science 249:386, 1990; Garrard et al., Bio/Techniques 9:1373, 1991; which are incorporated herein by reference in their entirety for all purposes. The resultant affinity sharpened CDR variant humanized immunoglobulin sequences are subsequently expressed in a suitable host.

Antibody fragments, which recognize specific epitopes, may be generated by known techniques. For example, such fragments include but are not limited to: the F(ab')$_2$ fragments which can be produced by pepsin digestion of the antibody molecule and the Fab fragments which can be generated by reducing the disulfide bridges of the (ab')$_2$ fragments. Alternatively, Fab expression libraries may be constructed (Huse et al., Science, 246:1275, 1989) to allow rapid and easy identification of monoclonal Fab fragments with the desired specificity. Techniques described for the production of single chain antibodies (U.S. Pat. No. 4,946,778; Bird, Science 242:423, 1988; Huston et al., Proc. Natl. Acad. Sci. USA 85:5879, 1988; and Ward et al., Nature 334:544, 1989) can also be adapted to produce single chain antibodies against polypeptides containing IL-17, IL-17R, IL-18, IL-18R, IL-18BP, 4-1BB, 4-1BB-L, CD30, CD30-L, OX40, OX40-L or CD39 amino acid sequences. In addition, antibodies to the IL-17, IL-17R, IL-18, IL-18R, IL-18BP, 4-1BB, 4-1BB-L, CD30, CD30-L, OX40, OX40-L or CD39 polypeptides can, in turn, be utilized to generate anti-idiotype antibodies using techniques known to those skilled in the art. (See, e.g., Greenspan & Bona, FASEB J 7(5):437, 1993; and Nissinoff, J. Immunol 147(8):2429, 1991).

I. Nucleic Acid-Based IL-17, IL-18, 4-1BB, CD30 and OX40 Antagonists

In alternative embodiments, nucleic acid-based immuno therapy can be designed to reduce the level of endogenous IL-17, IL-17R, IL-18, IL-18R, IL-18BP, 4-1BB, 4-1BB-L, CD30, CD30-L, OX40, OX40-L or CD39 gene expression, e.g., using antisense or ribozyme approaches to inhibit or prevent translation of IL-17, IL-17R, IL-18, IL-18R, IL-18BP, 4-1BB, 4-1BB-L, CD30, CD30-L, OX40, OX40-L or CD39 mRNA transcripts; triple helix approaches to inhibit transcription of the IL-17, IL-17R, IL-18, IL-18R, IL-18BP, 4-1BB, 4-1BB-L, CD30, CD30-L, OX40, OX40-L or CD39 gene; or targeted homologous recombination to inactivate or "knock out" the IL-17, IL-17R, IL-18, IL-18R, IL-18BP, 4-1BB, 4-1BB-L, CD30, CD30-L, OX40, OX40-L or CD39 gene or its endogenous promoter.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a mRNA having an IL-17, IL-17R, IL-18, IL-18R, IL-18BP, 4-1BB, 4-1BB-L, CD30, CD30-L, OX40, OX40-L or CD39 polynucleotide sequence. Absolute complementarity, although preferred, is not required. A sequence "complementary" to a portion of RNA, as referred to herein, means a sequence having sufficient complementarity to be able to hybridize with the RNA, thereby forming a stable duplex. Oligonucleotides that are complementary to the 5' end of the message, e.g., the 5' untranslated sequence up to and including the AUG initiation codon, should work most efficiently at inhibiting translation. However, oligonucleotides complementary to either the 5'- or 3'- non- translated, non-coding regions of the IL-17, IL-17R, IL-18, IL-18R, IL-18BP, 4-1BB, 4-1BB-L, CD30, CD30-L, OX40, OX40-L or CD39 gene transcript could be used in an antisense approach to inhibit translation of endogenous IL-17, IL-17R, IL-18, IL-18R, IL-18BP, 4-1BB, 4-1BB-L, CD30, CD30-L, OX40, OX40-L or CD39. Oligonucleotides complementary to the 5' untranslated region of the mRNA should include the complement of the AUG start codon. Antisense nucleic acids should be at least six nucleotides in length, and are preferably oligonucleotides ranging from 6 to about 50 nucleotides in length. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988), or hybridization-triggered cleavage agents or intercalating agents (see, e.g., Zon, 1988, Pharm. Res. 5:539-549).

The antisense molecules are delivered to cells, which express a transcript having an IL-17, IL-17R, IL-18, IL-18R, IL-18BP, 4-1BB, 4-1BB-L, CD30, CD30-L, OX40, OX40-L or CD39 polynucleotide sequence in vivo by, for example, injecting directly into the tissue or cell derivation site, or by use of modified antisense molecules, designed to target the desired cells (e.g., antisense linked to peptides or antibodies that specifically bind receptors or antigens expressed on the target cell surface) can be administered systemically. Another approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous IL-17, IL-17R, IL-18, IL-18R, IL-18BP, 4-1BB, 4-1BB-L, CD30, CD30-L, OX40, OX40-L or CD39 transcripts and thereby prevent translation of the IL-17 mRNA. For example, a vector can be introduced in vivo such that it is taken up by a cell and directs the transcription of an antisense RNA. Such a vector can remain episomal or become chromosomally integrated, so long as it can be transcribed to produce the desired antisense RNA. Vectors can be plasmid, viral, or others known in the art, used for replication and expression in mammalian cells.

Ribozyme molecules designed to catalytically cleave mRNA transcripts having an IL-17, IL-17R, IL-18, IL-18R, IL-18BP, 4-1BB, 4-1BB-L, CD30, CD30-L, OX40, OX40-L or CD39 polynucleotide sequence prevent translation of IL-17, IL-17R, IL-18, IL-18R, IL-18BP, 4-1BB, 4-1BB-L, CD30, CD30-L, OX40, OX40-L or CD39 mRNA (see, e.g., PCT International Publication WO90/11364, published Oct. 4, 1990; U.S. Pat. No. 5,824,519). Ribozymes are RNA molecules possessing the ability to specifically cleave other single-stranded RNA in a manner analogous to DNA restriction endonucleases. A major advantage of this approach is that, because they are sequence-specific, only mRNAs with particular sequences are inactivated. There are two basic types of ribozymes namely, tetrahymena-type (Hasselhoff, Nature, 334:585-591, 1988) and "hammerhead"-type. Tetrahymena-type ribozymes recognize sequences, which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes.

As in the antisense approach, the ribozymes can be composed of modified oligonucleotides (e.g. for improved stability, targeting, and the like). A typical method of delivery involves using a DNA construct "encoding" the ribozyme under the control of a strong constitutive pol III or pol II promoter, so that transfected cells will produce sufficient quantities of the ribozyme to destroy endogenous IL-17, IL-17R, IL-18, IL-18R, IL-18BP, 4-1BB, 4-1BB-L, CD30, CD30-L, OX40, OX40-L or CD39 message and inhibit translation. Because ribozymes, unlike antisense molecules, are catalytic, a lower intracellular concentration is required for efficiency.

Alternatively, endogenous IL-17, IL-17R, IL-18, IL-18R, IL-18BP, 4-1BB, 4-1BB-L, CD30, CD30-L, OX40, OX40-L or CD39 expression can be reduced by targeting deoxyribonucleotide sequences complementary to the regulatory region of the target gene (i.e., the target gene promoter and/or enhancers) to form triple helical structures that prevent transcription of the target IL-17, IL-17R, IL-18, IL-18R, IL-18BP, 4-1BB, 4-1BB-L, CD30, CD30-L, OX40, OX40-L or CD39 gene (see generally, Helene, 1991, Anticancer Drug Des., 6(6), 569-584; Helene, et al., 1992, Ann. N.Y. Acad. Sci., 660, 27-36; and Maher, 1992, Bioassays 14(12), 807-815).

Antisense RNA and DNA, ribozyme, and triple helix molecules of the invention may be prepared by any method known in the art for the synthesis of DNA and RNA molecules and include techniques for chemically synthesizing oligodeoxyribonucleotides and oligoribonucleotides such as, for example, solid phase phosphoramidite chemical synthesis, e.g. by use of an automated DNA synthesizer (such as are commercially available from Biosearch, Applied Biosystems, and the like). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448-7451). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In alternative embodiments IL-17, IL-17R, IL-18, IL-18R, IL-18BP, 4-1BB, 4-1BB-L, CD30, CD30-L, OX40, OX40-L or CD39 expression may be blocked by post-translational gene silencing, such as by double-stranded RNA-induced gene silencing, also known as RNA interference (RNAi). RNA sequences of IL-17, IL-17R, IL-18, IL-18R, IL-18BP, 4-1BB, 4-1BB-L, CD30, CD30-L, OX40, OX40-L or CD39 may be modified to provide double-stranded sequences or short hairpin RNAs for therapeutic use.

J. Screening for IL-17, IL-18, 4-1BB, CD30 and OX40 Antagonists

IL-17, IL-18, 4-1BB, CD30 and OX40 antagonists can be evaluated using screening assays known in the art, such as high throughput test systems. The assays can be performed in a variety of formats, including protein-protein binding assays, competition binding assays, biochemical screening assays, immunoassays, cell based assays, etc. For the sake of clarity, the following examples describe examplary assays in the context of IL-17 and IL-17R and are therefore illustrative and not limiting. The same assay formats and underlying rationale are equally applicable to IL-18:IL-18R, 4-1BB-L: 4-1BB, CD30-L:CD30 and OX40-L:OX40 interactions for screening for respective antagonists.

By observing the effect that an IL-17 antagonist has on the interaction between IL-17 and IL-17 receptor in various binding assays, on IL-17/IL-17 receptor-mediated activity in functional tests, and in cell based screens, molecules that are potential therapeutics are identified because they inhibit the interaction between IL-17 and IL-17 receptor. IL-17 antagonists that partially or completely inhibit IL-17 binding to IL-17 receptor, and hence the activation of IL-17 receptor, can be useful as immunosuppressants or anti-inflammatory agents in the treatment of cardiovascular disease.

One embodiment of a screening assay that can be used to screen IL-17 antagonists for their ability to inhibit the interaction of IL-17 and IL-17 receptor comprises the steps of forming a composition comprising an IL-17 protein, an IL-17 receptor protein, and the test compound (i.e., a putative IL-17 antagonist); assaying for the level of interaction of the IL-17 protein, an IL-17 receptor protein; and comparing the level obtained in the presence of the test compound to that obtained in the absence of the test compound, such that if the level obtained differs, a compound that affects the interaction of IL-17 and IL-17 receptor is identified. In alternative embodiments, at least one of the IL-17 or IL-17 receptor can be labeled with a detectable moiety. In alternative embodiments, one of the IL-17 or IL-17 receptor can be soluble, and the other can be bound, although alternative assay formats are possible and well known. The test compound can be added to the composition after addition of the IL-17 and IL-17 receptor, before both proteins are added, or after one protein is added and before the other is added.

In another aspect, the screening methods comprise forming a composition comprising the test compound, the IL-17 protein and cells expressing IL-17 receptor; determining the level of biological activity of IL-17 on the IL-17 receptor in the composition; and comparing the level of biological activity with that which occurs in the absence of test compound, wherein a difference in the level of biological activity indicates that the test compound affects the biological activity of the IL-17/IL-17 receptor complex. Biological activity of IL-17 on the IL-17 receptor can be assayed in any number of ways, for example but not limited to, determining the phosphorylation state of intracellular proteins (i.e., activation of the IL-17 receptor by IL-17); determining the production of proinflammatory factors, such as IL-6, IL-8, monocyte chemoattractant protein-1 and Groa; determining the production of hematopoietic cytokines, such as G-CSF and GM-CSF and IL-8; and determining increased expression of IL-1β and TNF-α, as well as measuring induction of iNOS in macrophages.

A particular example of an assay for the identification of potential IL-17 antagonists is a competitive assay, which combines IL-17 and an IL-17 receptor-specific antagonist with IL-17 receptor under the appropriate conditions for a competitive assay. Either IL-17 or the IL-17 receptor-specific antagonist can be labeled so that the binding can be measured and the effectiveness of the antagonist judged. The label allows for detection by direct or indirect means. Direct means include, but are not limited to luminescence, radioactivity, optical or electron density. Indirect means include but are not limited to an enzyme or epitope tag.

Another method by which IL-17 antagonists can be identified that inhibit the interaction between IL-17 and IL-17 receptor is the solid phase method, in which IL-17 receptor is bound and placed in a medium with labeled IL-17. The amount of signal produced by the interaction between IL-17 and IL-17 receptor is measured in the presence and in the absence of a test compound. Diminished levels of signal, in comparison to a control, indicate that the test compound inhibited the interaction between IL-17 and IL-17 receptor. Increased levels of signal, in comparison to a control, indicate that the candidate molecule promotes the interaction between IL-17 and IL-17 receptor. In alternative embodiments, IL-17 could be bound and IL-17 receptor labeled. The IL-17 antagonist, IL-17 receptor and/or IL-17 proteins can be directly or indirectly labeled. For example, if the protein is recombinantly produced, one can engineer fusion proteins that can facilitate solubility, labeling, immobilization and/or detection. Fusion proteins which facilitate these processes can include, but are not limited to soluble Ig-tailed fusion proteins and His-tagged proteins. Methods for engineering such soluble Ig-tailed fusion proteins are well known to those of skill in the art. See, for example, U.S. Pat. No. 5,116,964, and the illustrative embodiments described below. Indirect labeling involves the use of a protein, such as a labeled antibody, which specifically binds to a component of the assay. IL-17, IL-18, 4-1BB, CD30 and OX40 antagonists can be identified and evaluated using cells and/or cell lines derived from heart and vascular tissues. For example, cardiomyocyte cells and cell lines may be used to evaluate IL-17, IL-18, 4-1BB, CD30 and OX40 antagonists in any of the suitable assays described herein. Biologically relevant readouts in the cardiomyocyte-based assay (or other cells) may be used to evaluate potential antagonists, such as cell survival; hypertrophic responses; and/or production of ANP and/or BNP in response to hypoxic or environmental stress.

IL-17, IL-18, 4-1BB, CD30 and OX40 antagonists can also be identified using methods that are well suited for high-throughput screening procedures, such as scintillation proximity assays (Udenfriend et al., 1985, *Proc Natl Acad Sci USA* 82: 8672-8676), yeast two-hybrid or interaction trap assays, homogeneous time-resolved fluorescence methods (Park et al., 1999, *Anal Biochem* 269: 94-104), fluorescence resonance energy transfer (FRET) methods (Clegg R M, 1995, Curr Opin Biotechnol 6: 103-110), or methods that measure any changes in surface plasmon resonance when a bound polypeptide is exposed to a potential binding partner, using for example a biosensor such as that supplied by Biacore AB (Uppsala, Sweden).

Compounds that can be assayed that may also be IL-17, IL-18, 4-1BB, CD30 and OX40 antagonists include but are not limited to small organic molecules, such as those that are commercially available - often as part of large combinatorial chemistry compound 'libraries'—from companies such as Sigma-Aldrich (St. Louis, Mo.), Arqule (Woburn, Mass.), Enzymed (Iowa City, Iowa), Maybridge Chemical Co.(Trevillett, Cornwall, UK), MDS Panlabs (Bothell, Wash.), Pharmacopeia (Princeton, N.J,), and Trega (San Diego, Calif.). Preferred small organic molecules for screening using these assays are usually less than 10K molecular weight and can possess a number of physicochemical and pharmacological properties which enhance cell penetration, resist degradation, and/or prolong their physiological half-lives (Gibbs, J., 1994, Pharmaceutical Research in Molecular Oncology, *Cell* 79(2): 193-198). Compounds including natural products, inorganic chemicals, and biologically active materials such as proteins and toxins can also be assayed using these methods for the ability to bind to serve as IL-17, IL-18, 4-1BB, CD30 and OX40 antagonists.

Antagonizing IL-17:IL-17R, IL-18:IL-18R, 4-1BB-L:4-1BB, CD30-L:CD30 and/or OX40-L:OX40 interactions and therefore intercellular communication, cell stimulation, or immune cell activity can be manipulated by IL-17, IL-18, 4-1BB, CD30 and OX40 antagonists to control these activities in target cells. For example, IL-17, IL-18, 4-1BB, CD30 and OX40 antagonists or nucleic acids encoding IL-17, IL-18, 4-1BB, CD30 and OX40 antagonists can be administered to a cell or group of cells to block IL-17:IL-17R, IL-18:IL-18R, 4-1BB-L:4-1BB, CD30-L:CD30 and/or OX40-L:OX40 binding and thereby suppress or arrest cellular communication, cell stimulation, or activity in the target cells. In such an assay, one would determine a rate of communication or cell stimulation in the presence of the IL-17:IL-17R, IL-18:IL-18R, 4-1BB-L:4-1BB, CD30-L:CD30 and/or OX40-L:OX40 binding and then determine if such communication or cell stimulation is altered in the presence of IL-17, IL-18, 4-1BB, CD30 and/or OX40 antagonists. Exemplary assays for this aspect of the invention include cytokine secretion assays, T-cell co-stimulation assays, and mixed lymphocyte reactions involving antigen presenting cells and T cells. These assays are well known to those skilled in the art.

IL-17, IL-18, 4-1BB, CD30 and/or OX40 antagonists may regulate cytokine, cell proliferation (either inducing or inhibiting), or cell differentiation (either inducing or inhibiting) activity, or may induce production of other cytokines in certain cell populations. Many polypeptide factors discovered to date have exhibited such activity in one or more factor-dependent cell proliferation assays, and hence the assays serve as a convenient confirmation of cell stimulatory activity. The activity of IL-17, IL-18, 4-1BB, CD30 and/or OX40 antagonists may be evidenced by any one of a number of routine factor-dependent cell proliferation assays for cell lines including, without limitation, NFκB, 32D, DA2, DA1G, T10, B9, B9/11, BaF3, MC9/G, M+ (preB M+), 2E8, RBS, DA1, 123, T1165, HT2, CTLL2, TF-1, Mole and CMK.

The activity of IL-17, IL-18, 4-1BB, CD30 and/or OX40 antagonists may, among other means, be measured by the following methods:

Assays for receptor-ligand activity include without limitation those described in: *Current Protocols in Immunology* Coligan et al. eds, Greene Publishing Associates and Wiley-Interscience (Chapter 7.28, Measurement of cellular adhesion under static conditions 7.28.1-7.28.22), Takai et al., *PNAS USA* 84:6864-6868, 1987; Bierer et al., *J. Exp. Med.* 168:1145-1156, 1988; Rosenstein et al., *J. Exp. Med.* 169: 149-160 1989; Stoltenborg et al., *J. Immunol. Methods* 175: 59-68, 1994; Stitt et al., *Cell* 80:661-670, 1995.

Assays for T-cell or thymocyte proliferation include without limitation those described in: *Current Protocols in Immunology*, Coligan et al. eds, Greene Publishing Associates and Wiley-Interscience (pp. 3.1-3.19: In vitro assays for mouse lymphocyte function; Chapter 7. Immunologic studies in humans); Takai et al., *J. Immunol.* 137: 3494-3500, 1986; Bertagnolli et al., *J. Immunol.* 145: 1706-1712, 1990; Bertagnolli et al., *Cellular Immunology* 133:327-341, 1991; Bertagnolli, et al., *J. Immunol.* 149:3778-3783, 1992; Bowman et al., *J. Immunol.* 152: 1756-1761, 1994.

Assays for cytokine production and/or proliferation of spleen cells, lymph node cells or thymocytes include, without limitation, those described in: Kruisbeek and Shevach, 1994, Polyclonal T cell stimulation, in Current Protocols in *Immunology*, Coligan et al. eds. Vol 1 pp. 3.12.1-3.12.14, John Wiley and Sons, Toronto; and Schreiber, 1994, Measurement of mouse and human interferon gamma in *Current Protocols in Immunology*, Coligan et al. eds. Vol 1 pp. 6.8.1-6.8.8, John Wiley and Sons, Toronto.

Assays for proliferation and differentiation of hematopoietic and lymphopoietic cells include, without limitation, those described in: Bottomly et al., 1991, Measurement of human and murine interleukin 2 and interleukin 4, in *Current Protocols in Immunology*, Coligan et al. eds. Vol 1 pp. 6.3.1-6.3.12, John Wiley and Sons, Toronto; deVries et al., *J Exp Med* 173: 1205-1211, 1991; Moreau et al., *Nature* 336:690-692, 1988; Greenberger et al., *Proc Natl Acad Sci.USA* 80: 2931-2938, 1983; Nordan, 1991, Measurement of mouse and human interleukin 6, in *Current Protocols in Immunology* Coligan et al. eds. Vol 1 pp. 6.6.1-6.6.5, John Wiley and Sons, Toronto; Smith et al., *Proc Natl Acad Sci USA* 83: 1857-1861, 1986; Bennett et al., 1991, Measurement of human interleukin 11, in *Current Protocols in Immunology* Coligan et al. eds. Vol 1 pp. 6.15.1 John Wiley and Sons, Toronto; Ciarletta et al., 1991, Measurement of mouse and human Interleukin 9, in

*Current Protocols in Immunology*; Coligan et al. eds. Vol 1 pp. 6.13.1, John Wiley and Sons, Toronto.

Assays for T-cell clone responses to antigens (which will identify, among others, polypeptides that affect APC-T cell interactions as well as direct T-cell effects by measuring proliferation and cytokine production) include, without limitation, those described in: *Current Protocols in Immunology*, Coligan et al. eds, Greene Publishing Associates and Wiley-Interscience (Chapter 3: In vitro assays for mouse lymphocyte function; Chapter 6: Cytokines and their cellular receptors; Chapter 7: Immunologic studies in humans); Weinberger et al., *PNAS USA* 77: 6091-6095, 1980; Weinberger et al., *Eur. J. Immun.* 11:405-411, 1981; Takai et al., *J. Immunol.* 137:3494-3500, 1986; Takai et al., *J. Immunol.* 140:508-512, 1988

Assays for thymocyte or splenocyte cytotoxicity include, without limitation, those described in: *Current Protocols in Immunology*, Coligan et al. eds, Greene Publishing Associates and Wiley-Interscience (Chapter 3, In Vitro assays for Mouse Lymphocyte Function 3.1-3.19; Chapter 7, Immunologic studies in Humans); Herrmann et al., *PNAS USA* 78:2488-2492, 1981; Herrmann et al., *J. Immunol.* 128: 1968-1974, 1982; Handa et al., *J. Immunol.* 135:1564-1572, 1985; Takai et al., *J. Immunol.* 137:3494-3500, 1986; Takai et al., *J. Immunol.* 140:508-512, 1988; Herrmann et al., *PNAS USA* 78:2488-2492, 1981; Herrmann et al., *J. Immunol.* 128: 1968-1974, 1982; Handa et al., *J. Immunol.* 135:1564-1572, 1985; Takai et al., *J. Immunol.* 137:3494-3500, 1986; Bowman et al., *J. Virology* 61:1992-1998; Takai et al., *J. Immunol.* 140:508-512, 1988; Bertagnolli et al., *Cellular Immunology* 133:327-341, 1991; Brown et al., *J. Immunol.* 153:3079-3092, 1994.

Assays for T-cell-dependent immunoglobulin responses and isotype switching (which will identify, among others, polypeptides that modulate T-cell dependent antibody responses and that affect Th1/Th2 profiles) include, without limitation, those described in: Maliszewski, *J Immunol* 144: 3028-3033, 1990; and Mond and Brunswick, 1994, Assays for B cell function: in vitro antibody production, in *Current Protocols in Immunology* Coligan et al. eds. Vol 1 pp. 3.8.1-3.8.16, John Wiley and Sons, Toronto.

Mixed lymphocyte reaction (MLR) assays (which will identify, among others, polypeptides that generate predominantly Th1 and CTL responses) include, without limitation, those described in: *Current Protocols in Immunology*, Coligan et al. eds, Greene Publishing Associates and Wiley-Interscience (Chapter 3, In Vitro assays for Mouse Lymphocyte Function 3.1-3.19; Chapter 7, Immunologic studies in Humans); Takai et al., J. Immunol 137:3494-3500, 1986; Takai et al., J. Immunol 140:508-512, 1988; Bertagnolli et al., J. Immunol. 149:3778-3783, 1992.

Dendritic cell-dependent assays (which will identify, among others, polypeptides expressed by dendritic cells that activate naive T-cells) include, without limitation, those described in: Guery et al., *J. Immunol* 134:536-544, 1995; Inaba et al., *J Exp Med* 173:549-559, 1991; Macatonia et al., *J Immunol* 154:5071-5079, 1995; Porgador et al., *J Exp Med* 182:255-260, 1995; Nair et al., *J Virology* 67:4062-4069, 1993; Huang et al., *Science* 264:961-965, 1994; Macatonia et al., *J Exp Med* 169:1255-1264, 1989; Bhardwaj et al., *J Clin Invest* 94:797-807, 1994; and Inaba et al., *J Exp Med* 172: 631-640,1990.

Assays for lymphocyte survival/apoptosis (which will identify, among others, polypeptides that prevent apoptosis after superantigen induction and polypeptides that regulate lymphocyte homeostasis) include, without limitation, those described in: Darzynkiewicz et al., *Cytometry* 13:795-808, 1992; Gorczyca et al., *Leukemia* 7:659-670, 1993; Gorczyca et al., *Cancer Research* 53:1945-1951, 1993; Itoh et al., *Cell* 66:233-243, 1991; Zacharchuk, *J Immunol* 145:4037-4045, 1990; Zamai et al., *Cytometry* 14:891-897, 1993; Gorczyca et al., *International Journal of Oncology* 1:639-648, 1992.

Assays for polypeptides that influence early steps of T-cell commitment and development include, without limitation, those described in: Antica et al., *Blood* 84:111-117, 1994; Fine et al., *Cell Immunol* 155:111-122, 1994; Galy et al., *Blood* 85:2770-2778, 1995; Toki et al., *PNAS USA* 88:7548-7551, 1991

Assays for embryonic stem cell differentiation (which will identify, among others, polypeptides that influence embryonic differentiation hematopoiesis) include, without limitation, those described in: Johansson et al. *Cellular Biology* 15:141-151, 1995; Keller et al., *Molecular and Cellular Biology* 13:473-486, 1993; McClanahan et al., *Blood* 81:2903-2915, 1993.

Assays for cell movement and adhesion include, without limitation, those described in: *Current Protocols in Immunology* Coligan et al. eds, Greene Publishing Associates and Wiley-Interscience (Chapter 6.12, Measurement of alpha and beta chemokines 6.12.1-6.12.28); Taub et al. *J. Clin. Invest.* 95:1370-1376, 1995; Lind et al. *APMIS* 103:140-146, 1995; Muller et al *Eur. J. Immunol.* 25: 1744-1748; Gruber et al. *J Immunol.* 152:5860-5867, 1994; Johnston et al. *J Immunol.* 153: 1762-1768, 1994

Assay for hemostatic and thrombolytic activity include, without limitation, those described in: Linet et al., *J. Clin. Pharmacol.* 26:131-140, 1986; Burdick et al., *Thrombosis Res.* 45:413-419,1987; Humphrey et al., *Fibrinolysis* 5:71-79 (1991); Schaub, *Prostaglandins* 35:467-474, 1988.

II. Therapeutic Compositions and Administration Thereof

This invention provides compounds, compositions, and methods for treating a subject, preferably a human patient, who is suffering from cardiovascular disease. The terms "treat", "treating", and "treatment" used herein includes curative, preventative (e.g., prophylactic) and palliative or ameliorative treatment. Therapeutic compositions of IL-17, IL-18, 4-1BB, CD30 and/or OX40 antagonist and/or CD39 may therefore need to be administered before, during, or after the presentation of symptoms. For therapeutic use, a soluble IL-17, IL-18, 4-1BB, CD30 and/or OX40 antagonist and/or CD39 is administered to a subject for treatment in a manner appropriate to the indication.

Embodiments of the invention include therapeutic compositions (also referred to as pharmaceutical compositions) comprising one or more soluble IL-17, IL-18, 4-1BB, CD30 and/or OX40 antagonists and/or CD39. A "therapeutic composition," as used herein, comprises one or more soluble IL-17, IL-18, 4-1BB, CD30 and/or OX40 antagonists and/or CD39 and a pharmaceutically acceptable diluent, preservative, solubilizer, emulsifier, adjuvant and/or carrier. As used herein, the terms "pharmaceutically" acceptable and "physiologically" acceptable are used interchangeably. The term "pharmaceutically acceptable" means a non-toxic material that does not interfere with the effectiveness of the biological activity of the active ingredient(s).

Therefore, therapeutic compositions comprise all of the antagonists described in the sections above: e.g., soluble receptor molecules, ligands and/or binding proteins, such as IL-17, IL-17R, IL-18, IL-18R, IL-18 binding protein (IL-18BP), 4-1BB, 4-1BB-L, CD30, CD30-L, OX40, OX40-L and CD39, as well as biologically active fragments, muteins, variants, derivatives, fusions, etc. thereof; antibodies, fusion proteins and/or peptibodies directed against one or more of the following: IL-17, IL-17R, IL-18, IL-18R, IL-18 binding protein (IL-18BP), 4-1BB, 4-1BB-L, CD30, CD30-L, OX40, OX40-L and CD39; small molecules, such as peptidomimetics, mimotopes and the like, that antagonize the interaction between IL-17 and IL-17R, IL-18 and IL-18R, CD30-L and CD30, 4-1BB-L and 4-1BB and/or OX40-L and OX40; anti-sense oligonucleotides that specifically target and hybridize to the mRNA of endogenous IL-17, IL-17R, IL-18, IL-18R, IL-18BP, 4-1BB, 4-1BB-L, CD30, CD30-L, OX40, OX40-L or CD39 to inhibit or prevent translation of IL-17, IL-17R, IL-18, IL-18R, IL-18BP, 4-1BB, 4-1BB-L, CD30, CD30-L, OX40, OX40-L or CD39 mRNA transcripts; and RNA-interference molecules tailored to silence expression of IL-17, IL-17R, IL-18, IL-18R, IL-18BP, 4-1BB, 4-1BB-L, CD30, CD30-L, OX40, OX40-L or CD39.

Physiologically acceptable carriers, excipients or diluents are nontoxic to recipients at the dosages and concentrations employed. Ordinarily, preparing such compositions entails combining the IL-17, IL-18, 4-1BB, CD30 and/or OX40 antagonist and/or CD39 with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with conspecific serum albumin are exemplary appropriate diluents. The IL-17, IL-18, 4-1BB, CD30 and/or OX40 antagonist and/or CD39 preferably is formulated as a lyophilizate using appropriate excipient solutions (e.g., sucrose) as diluents. Appropriate dosages can be determined in standard dosing trials, and may vary according to the chosen route of administration. In accordance with appropriate industry standards, preservatives may also be added, such as benzyl alcohol. The amount and frequency of administration will depend, of course, on such factors as the nature and severity of the indication being treated, the desired response, the age and condition of the patient, and so forth In one embodiment, sustained-release forms of soluble IL-17, IL-18, 4-1BB, CD30 and/or OX40 antagonist and/or CD39 described herein, are used. Sustained-release forms suitable for use in the disclosed methods include, but are not limited to, IL-17, IL-18, 4-1BB, CD30 and/or OX40 antagonist and/or CD39, that is encapsulated in a slowly-dissolving biocompatible polymer, admixed with such a polymer, and or encased in a biocompatible semi-permeable implant. In addition, the IL-17, IL-18, 4-1BB, CD30 and/or OX40 antagonist and/or CD39 may be conjugated with polyethylene glycol (pegylated) to prolong its serum half-life or to enhance protein delivery (as described in detail above).

One type of sustained release technology that may be used in administering soluble IL-17, IL-18, 4-1BB, CD30 and/or OX40 antagonist and/or CD39 therapeutic compositions is that utilizing hydrogel materials, for example, photopolymerizable hydrogels (Sawhney et al., *Macromolecules* 26:581; 1993). Similar hydrogels have been used to prevent postsurgical adhesion formation (Hill-West et al., *Obstet. Gynecol.* 83:59, 1994) and to prevent thrombosis and vessel narrowing following vascular injury (Hill-West et al., *Proc. Natl. Acad. Sci. USA* 91:5967, 1994). Polypeptides can be incorporated into such hydrogels to provide sustained, localized release of active agents (West and Hubbel, *Reactive Polymers* 25:139, 1995; Hill-West et al., *J. Surg. Res.* 58:759; 1995). The sustained, localized release of IL-17, IL-18, 4-1BB, CD30 and/or OX40 antagonist and/or CD39 when incorporated into hydrogels would be amplified by the long half life of IL-17, IL-18, 4-1BB, CD30 and/or OX40 antagonist and/or CD39.

Therapeutic compositions may be for administration for injection, or for oral, pulmonary, nasal, transdermal or other forms of administration. In general, the invention encompasses therapeutic compositions comprising effective amounts one or more IL-17, IL-18, 4-1BB, CD30 and/or OX40 antagonist and/or CD39 together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., *Remington's Pharmaceutical Sciences*, 18th Ed. (1990, Mack Publishing Co., Easton, Pa. 18042) pages 1435-1712 which are herein incorporated by reference in their entirety. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Chapter 89 of *Remington's Pharmaceutical Sciences* (1990), 18th Ed., Mack Publishing Co. Easton Pa. 18042, which is herein incorporated by reference in its entirety. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., *Modern Pharmaceutics* (1979), edited by G. S. Banker and C. T. Rhodes, herein incorporated by reference in its entirety. In general, the formulation will include one or more IL-17, IL-18, 4-1BB, CD30 and/or OX40 antagonist and/or CD39, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, *Soluble Polymer-Enzyme Adducts, Enzymes as Drugs* (1981), Hocenberg and Roberts, eds., Wiley-Interscience, New York, N.Y., pp. 367-83; Newmark, et al. (1982), *J. Appl. Biochem.* 4:185-9. Other polymers that could be used are poly-1,3-dioxolane and poly-1,3,6-tioxocane. Preferred for pharmaceutical usage, as indicated above, are PEG moieties. For oral delivery dosage forms, it is also possible to use a salt of a modified aliphatic amino acid, such as sodium N-(8-[2-hydroxybenzoyl]amino)caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, a-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms; e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7: 565-9; Adjei et al. (1990), *Internatl. J. Pharmaceutics* 63: 135-44 (leuprolide acetate); Braquet et al. (1989), *J. Cardiovasc. Pharmacol.* 13 (suppl.5): s.143-146 (endothelin-1); Hubbard et al. (1989), *Annals Int. Med.* 3: 206-12 (α1-antitrypsin); Smith et al. (1989), *J. Clin. Invest.* 84: 1145-6 (α1-proteinase); Oswein et al. (March 1990), "Aerosolization of Proteins", *Proc. Symp. Resp. Drug Delivery II*, Keystone, Colo. (recombinant human growth hormone); Debs et al. (1988), *J. Immunol.* 140: 3482-8 (interferon-y and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of IL-17, IL-18, 4-1BB, CD30 and/or OX40 antagonist and/or CD39 is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

In practicing the method of treatment or use of IL-17, IL-18, 4-1BB, CD30 and/or OX40 antagonist and/or CD39, a therapeutically effective amount is administered to a subject. As used herein, the term "therapeutically effective amount" means the total amount of each therapeutic composition that is sufficient to show a meaningful patient benefit, i.e., treatment, healing, prevention or amelioration of the relevant medical condition, or an increase in rate of treatment, healing, prevention or amelioration of such conditions. When applied to an individual therapeutic composition, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the patient is treated with said therapeutic composition in an amount and for a time sufficient to induce an improvement, and preferably a sustained improvement, in at least one indicator that reflects the severity of the disorder. An improvement is considered "sustained" if the patient exhibits the improvement on at least two occasions separated by one or more days, or more preferably, by one or more weeks. The degree of improvement is determined based on signs or symptoms, and determinations can also employ questionnaires that are administered to the patient, such as quality-of-life questionnaires. Various indicators that reflect the extent of the patient's illness can be assessed for determining whether the amount and time of the treatment is sufficient. The baseline value for the chosen indicator or indicators is established by examination of the patient prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic compositions such as IL-17, IL-18, 4-1BB, CD30 and/or OX40 antagonist and/or CD39 until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating injuries or other acute conditions. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

One skilled in the pertinent art will recognize that suitable dosages will vary, depending upon such factors as the nature and severity of the disorder to be treated, the patient's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose can be formulated in animal models to achieve a circulating plasma concentration range that includes the IC50 (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of polypeptide of the present invention with which to treat each individual patient. Initially, the attending physician will administer low doses of polypeptide of the present invention and observe the patient's response. Larger doses of polypeptide of the present invention can be administered until the optimal therapeutic effect is obtained for the patient, and at that point the dosage is not increased further. It is contemplated that the various therapeutic compositions used to practice the method of the present invention should contain about 0.01 ng to about 100 mg (preferably about 0.1 ng to about 10 mg, more preferably about 0.1 microgram to about 1 mg) of polypeptide of the present invention per kg body weight. In one embodiment of the invention, IL-17, IL-18, 4-1BB, CD30 and/or OX40 antagonist and/or CD39 are administered one time per week to treat the various medical disorders disclosed herein, in another embodiment is administered at least two times per week, and in another embodiment is administered at least three times per week. If injected, the effective amount of IL-17, IL-18, 4-1BB, CD30 and/or OX40 antagonist and/or CD39 per adult dose ranges from 1-20 mg/m$^2$, and preferably is about 5-12 mg/m$^2$. Alternatively, a flat dose can be administered, whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described below are treated by administering a preparation acceptable for injection containing IL-17, IL-18, 4-1BB, CD30 and/or OX40 antagonist and/or CD39 at 25 mg/dose, or alternatively, containing 50 mg per dose. The 25 mg or 50 mg dose can be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of IL-17, IL-18, 4-1BB, CD30 and/or OX40 antagonist and/or CD39 one to three times per week over a period of at least three weeks, or a dose of 50 mg of IL-17, IL-18, 4-1BB, CD30 and/or OX40 antagonist and/or CD39 one or two times per week for at least three weeks, though treatment for longer periods may be necessary to induce the desired degree of improvement. For incurable chronic conditions, the regimen can be continued indefinitely, with adjustments being made to dose and frequency if such are deemed necessary by the patient's physician. The foregoing doses are examples for an adult patient who is a person who is 18 years of age or older. For pediatric patients (age 4-17), a suitable regimen involves the subcutaneous injection of 0.4 mg/kg, up to a maximum dose of 25 mg of IL-17, IL-18, 4-1BB, CD30 and/or OX40 antagonist and/or CD39, administered by subcutaneous injection one or more times per week. If an IL-17, IL-18, 4-1BB, CD30 and/or OX40 antagonist is in the form of an antibody, a preferred dose range is 0.1 to 20 mg/kg, and more preferably is 1-10 mg/kg. Another embodiment of a dose range is 0.75 to 7.5 mg/kg of body weight. Humanized antibodies are preferred, that is, antibodies in which only the antigen-binding portion of the antibody molecule is derived from a non-human source. Such antibodies can be injected or administered intravenously.

III. Therapeutic Applications

IL-17, IL-18, 4-1BB, CD30 and OX40 antagonists may be used to treat cardiovascular disease. Embodiments of the present invention include methods of treating cardiovascular disease in a subject having having cardiovascular disease comprising administering an effective amount of one or more IL-17, IL-18, 4-1BB, CD30 and/or OX40 antagonists and/or CD39, alone or in any combination.

Cardiovascular disease includes disease states having pathophysiology of the heart and vasculature systems, as well as organs and systems compromised by disease states of the heart and vasculature systems. Examples include, but are not limited to: inflammation of the heart and/or vasculature such as myocarditis, chronic autoimmune myocarditis, bacterial and viral myocarditis, as well as infective endocarditis; heart failure; congestive heart failure; chronic heart failure; cachexia of heart failure; cardiomyopathy, including non-ischemic (dilated cardiomyopathy; idiopathic dilated cardiomyopathy; cardiogenic shock, heart failure secondary to extracorporeal circulatory support ("post-pump syndrome"), heart failure following ischemia/reperfusion injury, brain death associated heart failure (as described in Owen et al., 1999 (Circulation. 1999 May 18; 99(19):2565-70)); hypertrophic cardiomyopathy; restrictive cardiomyopathy; non-ischemic systemic hypertension;

valvular disease; arythmogenic right ventricular cardiomyopathy) and ischemic (atherogenesis; atherosclerosis; arteriosclerosis; peripheral vascular disease; coronary artery disease; infarctions, including stroke, transient ischemic attacks and myocardial infarctions). Additional disease states encompassed by the definition of cardiovascular disease include: aneurysms; arteritis; angina; embolism; platelet-associated ischemic disorders; ischemia/reperfusion injury; restenosis; mitral and/or tricuspid regurgitation; mitral stenosis; silent myocardial ischemia; Raynaud's phenomena; thrombosis; deep venous thrombosis; pulmonary embolism; thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surfacethrombophlebitis; vasculitis, including Kawasaki's vasculitis; Takayasu's arteritis; veno-occlusive disease, giant cell arteritis, Wegener's granulomatosis; Schoenlein-Henoch purpura, as well as cardiovascular disease arising from periodontal infections by one or more oral pathogens, such as bacteria.

Additional examples of the therapeutic uses of one or more IL-17, IL-18, 4-1BB, CD30 and/or OX40 antagonists alone or in combination with CD39 include the treatment of individuals who suffer from coronary artery disease or injury following platelet-associated ischemic disorders including lung ischemia, coronary ischemia, and cerebral ischemia, and for the prevention of reocclusion following thrombosis, thrombotic disorders including coronary artery thrombosis, cerebral artery thrombosis, intracardiac thrombosis, peripheral artery thrombosis, venous thrombosis, thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surface, in combination with angioplasty, carotid endarterectomy, anastomosis of vascular grafts, and chronic cardiovascular devices such as in-dwelling catheters or shunts.

Further indications include subjects that are or will be undergoing angioplasty procedures (i.e., balloon angioplasty, laser angioplasty, coronary atherectomy and similar techniques), placement of endovascular prosthetic devices such as carotid, coronary, peripheral arterial or other endovascular stents, dialysis access devices, or procedures to treat peripheral vascular disease; individuals undergoing surgery that has a high risk of thrombus formation (i.e., coronary bypass surgery, insertion of a prosthetic valve or vessel and the like).

In addition, IL-17 and/or IL-18 are prognostic indicators of cardiovascular disease and disease severity. IL-17 and/or IL-18 are also prognostic indicators of donor adequacy and post-transplant outcome. Therefore, further embodiments of the invention include assays for measuring IL-17 and/or IL-18 levels in subjects being screened for cardiovascular disease, cardiovascular disease severity, donor adequacy and post-transplant outcome.

Various indicators that reflect the extent of the patient's illness may be assessed for determining whether the amount and time of the treatment is sufficient. The baseline value for the chosen indicator or indicators is established by examination of the patient prior to administration of the first dose of IL-17, IL-18, 4-1BB, CD30 and/or OX40 antagonists alone or in combination with soluble CD39. Preferably, the baseline examination is done within about 60 days of administering the first dose.

Improvement is induced by repeatedly administering a dose of IL-17, IL-18, 4-1BB, CD30 and/or OX40 antagonists alone or in combination with soluble CD39 until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Therapeutic compositions of the invention may be administered alone or in combination with a therapeutically effective amount of other drugs. The invention includes the administration of IL-17, IL-18, 4-1BB, CD30 and/or OX40 antagonists alone or in combination with soluble CD39 concurrently with one or more other drugs that are administered to the same patient in combination with the IL-17, IL-18, 4-1BB, CD30 and/or OX40 antagonists and/or CD39, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components can be administered in the same or in separate compositions, and by the same or different routes of administration.

Examples of other drugs or therapeutic compostions that may be used in combination with IL-17, IL-18, 4-1BB, CD30 and/or OX40 antagonists alone or in combination with soluble CD39 include: analgesic agents, disease-modifying anti-rheumatic drugs (DMARDs), non-steroidal anti-inflammatory drugs (NSAIDs), and any immune and/or inflammatory modulators. Non-steroidal anti-inflammatories may include, but are not limited to: salicylic acid (aspirin); ibuprofen; indomethacin; celecoxib; rofecoxib; ketorolac; nambumetone; piroxicam; naproxen; oxaprozin; sulindac; ketoprofen; diclofenac; other COX-1 and/or COX-2 inhibitors, salicylic acid derivatives, propionic acid derivatives, acetic acid derivatives, fumaric acid derivatives, carboxylic acid derivatives, butyric acid derivatives, oxicams, pyrazoles and pyrazolones, including newly developed anti-inflammatories.

Therapeutic compositions of this invention may be administered with one or more of the following: modulators of other members of the TNF/TNF receptor family, including TNF antagonists, such as etanercept (Enbrel™), sTNF-RI, onercept, D2E7, and Remicade™; IL-1 inhibitors, including IL-1ra molecules such as anakinra and more recently discovered IL-1ra-like molecules such as IL-1Hy1 and IL-1Hy2; IL-1 "trap" molecules as described in U.S. Pat. No. 5,844,099; IL-1 antibodies; solubilized IL-1 receptor, and the like; IL-6 inhibitors (e.g., antibodies to IL-6); IL-8 inhibitors (e.g., antibodies to IL-8); Interleukin-1 converting enzyme (ICE) modulators; insulin-like growth factors (IGF-1, IGF-2) and modulators thereof; transforming growth factor-β (TGF-β), TGF-β family members, and TGF-β modulators; fibroblast growth factors FGF-1 to FGF-10, and FGF modulators; COX-2 inhibitors, such as Celebrex™ and Vioxx™; prostaglandin analogs (e.g., E series prostaglandins); matrix metalloproteinase (MMP) modulators; nitric oxide synthase (NOS) modulators, including modulators of inducible NOS; modulators of glucocorticoid receptor; modulators of glutamate receptor; modulators of lipopolysaccharide (LPS) levels; anti-cancer agents, including inhibitors of oncogenes (e.g., fos, jun) and interferons; noradrenaline and modulators and mimetics thereof.

Additional embodiments of compositions that can be administered concurrently with the pharmaceutical compositions of the invention are: cytokines, lymphokines, or other hematopoietic factors such as M-CSF, GM-CSF, F1t3-Ligand, TNF, IL-1, IL-2, IL-3, IL4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin, or inhibitors or antagonists of any of these factors. The pharmaceutical composition can further contain other agents which either enhance the activity of the polypeptide or compliment its activity or use in treatment. Such additional factors and/or agents may be included in the pharmaceutical composition to produce a synergistic effect with polypeptide of the invention, or to minimize side effects. Conversely, IL-17, IL-18, 4-1BB, CD30 and/or OX40 antagonists and/or soluble CD39 may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

Further embodiments of drugs to be administered concurrently include but are not limited to antivirals, antibiotics, analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose.

Of course, IL-17, IL-18, 4-1BB, CD30 and/or OX40 antagonists and/or soluble CD39, as well as other therapeutic compostions described above, may be administered inconjuction with other recognized therapies or treatments, such as any surgical procedures involving the heart and vaculature (coronary bypass, heart transplant, valve replacement, angioplasty, stenting, atherectomy, aortic aneurysm repair, valve plication, ventricular assist device insertion, ventricular volume reduction surgery, any form of peripheral arterial surgery including bypass, vessel recanalisation or reconstruction, pediatric cardiovascular surgery including repair and correction of complex congenital lesions); Lipid-lowering drugs (such as, but not limited to Lipitor, simvastatin, pravastatin, atorvastatin, non-HMG CoA reductase inhibitors); blood pressure-regulating drugs (including but not limited to calcium channel antagonists, ACE-inthibitors, beta-blockers, orally and systemically available nitric oxide donors such as GTN); angiotensin-converting enzyme inhibitors, and peroxisome proliferator-activated receptor ligands.

In other embodiments of the invention, 4-1BB, CD30 and/or OX40 antagonists may be used to prevent, reduce and/or ameliorate the cardiotoxicity of chemotherapeutics. Drug toxicity remains a significant barrier to the delivery of curative doses of cancer chemotherapy. Many chemotherapeutic drugs cause direct injury to the heart, either acutely in the form of myocardial tissue injury or dysrhythmias, or in a chronic fashion associated with congestive heart failure. Examples of acute cardiotoxicity include supraventricular tachyarrhymias, which may be associated ECG changes, such as ST-T sgement changes, decreased voltage, T-wave flattening, as well as atrial and ventricular ectopy. Acute effects occur in up to 40% of patients receiving bolus doxorubicin and are usually transient. Chronic anthracycline cardiotoxicity may be manifested as arrythmias, myocarditis, pericarditis, myocardial infarction and cardiomyopathy that is dose- and schedule-dependent. Above cumulative bolus doses of 550 mg/m$^2$ the risk of congestive heart failure increases rapidly. Doses of less than 450 mg/m$^2$ pose a risk of less than 10%. Patients receiving anthracyclines also demontrate late-appearing cardiac toxicity occuring greater than 5 years after exposure to doxorubucin. Cardiac dysfunction is manifested as congestive heart failure or dysrhythmias and can occur in patients that were previously asymptomatic. It is estimated that approximtely 5% of patients surviving ten years after exposre to doxorubicin will experience this toxicity (see, Page, R., *Cancer Management: A Multidisciplinary Approach*, PRR Inc., Fifth Edition (2001).

Principal among the cardiotoxic agents are cytostatic antibiotics of the anthracycline class. The class of anthracylines includes, but is not limited to, Adriamycin (Doxorubicin), Daunorubicin, Ellence (Epirubicin), Idarubicin, Mitroxantrone, and the like. Therefore, embodiments of the invention provide methods of preventing, reducing and/or ameliorating the cardiotoxic effects of anthracylines comprising administrating an effective amount of a 4-1BB antagonists, CD30 antagonists and/or OX40 antagonists. Embodiments of the invention also provide compositions for preventing, reducing and/or ameliorating the cardiotoxic effects of anthracylines comprising an antagonist selected from the group consisting of a 4-1BB antagonists, CD30 antagonists and/or OX40 antagonists.

Embodiments of the invention provide methods of preventing, reducing and/or ameliorating the cardiotoxic effects of anthracylines selected from the group consisting of Adriamycin (Doxorubicin), Daunorubicin, Ellence (Epirubicin), Idarubicin and Mitroxantrone, comprising administrating an effective amount of a 4-1BB antagonists, CD30 antagonists and/or OX40 antagonists. Embodiments of the invention also provide compositions for preventing, reducing and/or ameliorating the cardiotoxic effects of anthracylines selected from the group consisting of Adriamycin (Doxorubicin), Daunorubicin, Ellence (Epirubicin), Idarubicin and Mitroxantrone, comprising an antagonist selected from the group consisting of a 4-1BB antagonists, CD30 antagonists and/or OX40 antagonists.

4-1BB antagonists, CD30 antagonists and/or OX40 antagonists may be used to prevent, reduce and/or ameliorate the cardiotoxic effects of other chemotherapeutics having cardiotoxicity, such as, but not limited to: Amsacrine, Busulfan, Cisplatin, Cyclophosphamide, Fluorouracil, Herceptin (and other Her2/neu-targeted modalities), Ifosfamide, Interferons, Interleukin-2, Mitomycin, Paclitaxel, Vinblastine, Vincristine and Xeloda (capecitabine).

Therefore, embodiments of the invention provide methods of preventing, reducing and/or ameliorating the cardiotoxic effects of chemotherapeutics having cardiotoxic side effects, comprising administrating an effective amount of a 4-1BB antagonists, CD30 antagonists and/or OX40 antagonists. Embodiments of the invention also provide compositions for preventing, reducing and/or ameliorating the cardiotoxic effects of chemotherapeutics having cardiotoxic side effects comprising an antagonist selected from the group consisting of a 4-1BB antagonists, CD30 antagonists and/or OX40 antagonists.

Embodiments of the invention provide methods of preventing, reducing and/or ameliorating the cardiotoxic effects of chemotherapeutics selected from the group consisting of Amsacrine, Busulfan, Cisplatin, Cyclophosphamide, Fluorouracil, Herceptin (and other Her2/neu-targeted modalities), Ifosfamide, Interferons, Interleukin-2, Mitomycin, Paclitaxel, Vinblastine, Vincristine and Xeloda (capecitabine), comprising administrating an effective amount of a 4-1BB antagonists, CD30 antagonists and/or OX40 antagonists. Embodiments of the invention also provide compositions for preventing, reducing and/or ameliorating the cardiotoxic effects of chemotherapeutics selected from the group consisting of Amsacrine, Busulfan, Cisplatin, Cyclophosphamide, Fluorouracil, Herceptin (and other Her2/neu-targeted modalities), Ifosfamide, Interferons, Interleukin-2, Mitomycin, Paclitaxel, Vinblastine, Vincristine and Xeloda (capecitabine), comprising an antagonist selected from the group consisting of a 4-1BB antagonists, CD30 antagonists and/or OX40 antagonists.

Embodiments of the invention provide methods of treating cancer in a subject in need thereof, wherein the dosage of a chemotherapeutic having cardiotoxicity is increased to more effectively treat the cancer but the cardiotoxic effects of the chemotherapeutic is prevented, reduced and/or ameiorated by administering an antagonist selected from the group consisting of a 4-1BB antagonists, CD30 antagonists and/or OX40 antagonists. Embodiments of the invention provide methods of treating cancer in a subject in need thereof, wherein the dosage of an anthracyline is increased to more effectively treat the cancer but the cardiotoxic effects of the anthracycline is prevented, reduced and/or ameiorated by administering an antagonist selected from the group consisting of a 4-1BB antagonists, CD30 antagonists and/or OX40 antagonists. Embodiments of the invention provide methods of treating cancer in a subject in need thereof, wherein the dosage of an anthracyline selected from the group consisting of Adriamycin (Doxorubicin), Daunorubicin, Ellence (Epirubicin), Idarubicin and Mitroxantrone is increased to more effectively treat the cancer but the cardiotoxic effects of the anthracycline is prevented, reduced and/or ameiorated by administering an antagonist selected from the group consisting of a 4-1BB antagonists, CD30 antagonists and/or OX40 antagonists. Embodiments of the invention provide methods of treating cancer in a subject in need thereof, wherein the dosage of a chemotherapeutic selected from the group consisting of Amsacrine, Busulfan, Cisplatin, Cyclophosphamide, Fluorouracil, Herceptin (and other Her2/neu-targeted modalities), Ifosfamide, Interferons, Interleukin-2, Mitomycin, Paclitaxel, Vinblastine, Vincristine and Xeloda (capecitabine) is increased to more effectively treat the cancer but the cardiotoxic effects of the chemotherapeutic is prevented, reduced and/or ameiorated by administering an antagonist selected from the group consisting of a 4-1BB antagonists, CD30 antagonists and/or OX40 antagonists.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are offered by way of illustration, and not limitation.

Sequence Identity Numbers and Associated Molecules

| SEQ ID NO. | Molecule |
|---|---|
| 1 | IL-17 polynucleotide sequence |
| 2 | IL-17 amino acid sequence |
| 3 | IL-17 Receptor polynucleotide sequence |
| 4 | IL-17 Receptor amino acid sequence |
| 5 | IL-18 Receptor: IL-1Rrp1 polynucleotide sequence |
| 6 | IL-18 Receptor: IL-1Rrp1 amino acid sequence |
| 7 | IL-18 Receptor: AcPL polynucleotide sequence |
| 8 | IL-18 Receptor: AcPL amino acid sequence |
| 9 | IL-18 Binding Protein a polynucleotide sequence |
| 10 | IL-18 Binding Protein a amino acid sequence |
| 11 | IL-18 Binding Protein-Fc fusion amino acid sequence |
| 12 | IL-18 polynucleotide sequence (unprocessed) |
| 13 | IL-18 amino acid sequence (unprocessed) |
| 14 | IL-18 amino acid sequence (ICE-processed) |
| 15 | 4-1BB-L polynucleotide sequence |
| 16 | 4-1BB-L amino acid sequence |
| 17 | 4-1BB polynucleotide sequence |
| 18 | 4-1BB amino acid sequence |
| 19 | CD30-L polynucleotide sequence (nt 1-648) |
| 20 | CD30-L polypeptide sequence (aa 1-215) |
| 21 | CD30-L polynucleotide sequence (nt 1-705) |
| 22 | CD30-L polypeptide sequence (aa 1-234) |
| 23 | CD30 polynucleotide sequence |
| 24 | CD30 polypeptide sequence |
| 25 | OX40-L polynucleotide sequence |
| 26 | OX40-L polypeptide sequence |
| 27 | OX40 polynucleotide sequence |
| 28 | OX40 polypeptide sequence |
| 29 | CD39 polynucleotide sequence |
| 30 | CD39 polypeptide sequence |
| 31 | Flag ® octapeptide |
| 32 | Linker - $(Gly)_4Ser(Gly)_5Ser$ |
| 33 | Linker - $GlyAlaGlyGlyAlaGlySer(Gly)_5Ser$ |
| 34 | Linker - $(Gly_4Ser)_2$ |
| 35 | Linker - $(GlyThrPro)_3$ |
| 36 | Linker - $(Gly_4Ser)_3Gly_4SerGly_5Ser$ |

EXAMPLES

Example 1

IL-17 AND IL-18 Plasma Levels are Elevated in Cardiomyopathy Patients

These studies demonstrate IL-17 and IL-18 are elevated in human patients having various forms and severity of cardiovascular disease.

In a series of studies, plasma levels of IL-17 and IL-18 were found to be elevated in patients having acute and chronic heart failure. Plasma from brain-dead organ donors was obtained at the time of heart removal and stored. The clinical outcome of the recipient that received the various organs was noted. A group of recipients that survived and did well was collected along with a group that died within 72 hours of transplantation due to cardiac failure refractory to maximal medical support. The plasma from the original donors, recipients and unused donors having an ejection fraction (EF) of less than 30% was assayed for IL-17 and IL-18. Cytokine levels were measured in plasma samples essentially as described in the protocols provided in commercially available ELISA kits (see, for example, QUANTKINE® R&D Systems, Minneapolis, Minn, which provides assays for the quantitative determination of human IL-17 and human IL-18).

Figure 1B:
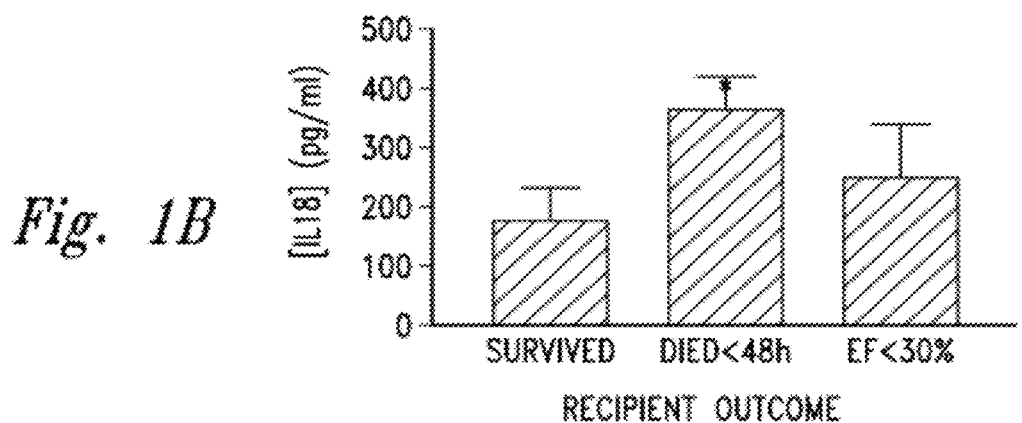

As shown in FIGS. 1A and 1B, IL-17 and IL-18 were elevated in patients that died shortly after transplantation in contrast to patients that survived. IL-17 and IL-18 were also elevated in unused donors having an ejection fraction (EF) of less than 30%, suggesting a correlation between circulating IL-17 and IL-18 levels and disease severity. This study further shows the diagnostic and prognostic value of assaying for IL-17 and IL-18 cytokine levels in heart patients, such as for the assessment of post-transplant survival.

Using the samples described above, IL-18 receptor expression was assessed. Heart samples were homogenized in ice-cold lysis buffer (New England Biolabs, Beverly, Mass.). The homogenate was centrifuged at 4° C. (12000×5 mins) and the supernatant assayed for protein content (Pierce BCA kit). The same total amount of protein (20 mg/lane) was subjected to SDS-PAGE using 5% gels. Proteins were then transferred to nitrocellulose membrane and IL-18 receptor visualized using a polyclonal antibody raised against IL-18R alpha (AF840-R&D Systems, Mineapolis, Minn.), and the ECL kit.

Figure 2:
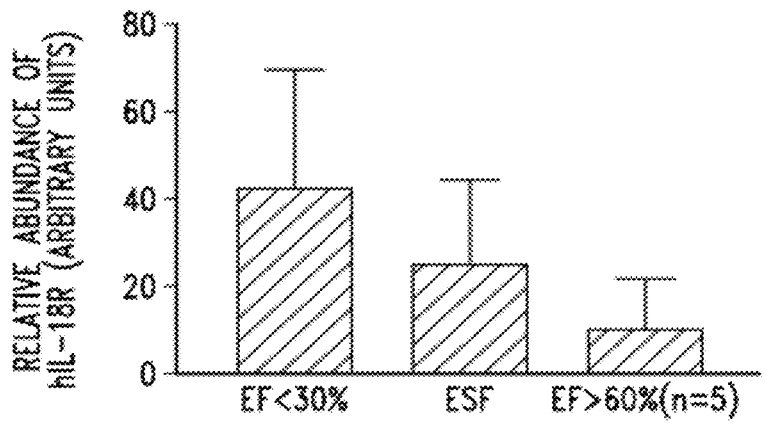
FIG. 2 shows relative abundance of IL-18 Receptor in patients having an ejection fraction (EF) of less than 30%, patients in end-stage failure (ESF) and patients having an ejection fraction of greater than 60% (i.e., normal myocardium).

As shown in FIG. 2 the relative abundance of IL-18 receptor is higher in patients having an ejection fraction (EF) of less than 30% as compared to patients in end stage heart failure-ESF (i.e., NYHA stage 4 cardiomyopathy) and patients havng an ejection fraction of greater than 60%. These data demonstrate that elevated IL-18 receptor expression is associated with impaired myocardial function. Given that IL-18 signals through the Toll-IL-1 receptor pathway (TIR) and that both lipopolysacharide and IL-1 are negatively inotropic, elevated expression of the IL-18 receptor could well account for part of the myocardial dysfunction seen in these patients.

Samples from cardiac patients participating in the multi-center Renaissance Trial were evaluated. The patients exhibited a continuim of functional capacity and objective evidence of cardiovascular disease, as classifed by the Criteria Committee of the New York Heart Association (*Nomenclature and Criteria for Diagnosis of Diseases of the Heart and Great Vessels.* 9$^{th}$ ed. Boston Mass: Little, Brown & co; 1994: 253-256). Samples were evaluated for cytokine levels using the assays described above.

FIGS. 3A-3D depict the plasma concentration of IL-17 and IL-18 (pg/ml) in cardiomypoathy patients diagnosed in NYHA classes 1, 2, 3a, 3b and 4. This data shows a dramatic and unexpected increase in the amount of circulating IL-17 in NYHA classes 2, 3a and 3b (FIG. 1A). Elevated IL-17 levels were found in both non-ischemic and ischemic cardiomyopathy for the same classes (FIG. 1B). IL-17 levels were significantly higher in NYHA class 3a for ischemic cardiomyopathy. Significantly, this data shows a direct correlation between IL-17 levels and progression of disease up to NYHA class 3b and a decrease in IL-17 in NYHA class 4.

Figure 3A:
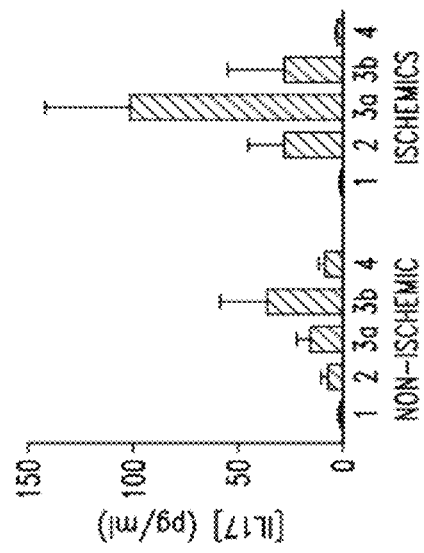
FIGS. 3A through 3D show comparative levels of IL-17 and IL-18 plasma levels among patients in various stages of cardiomyopathy.
Figure 3B:
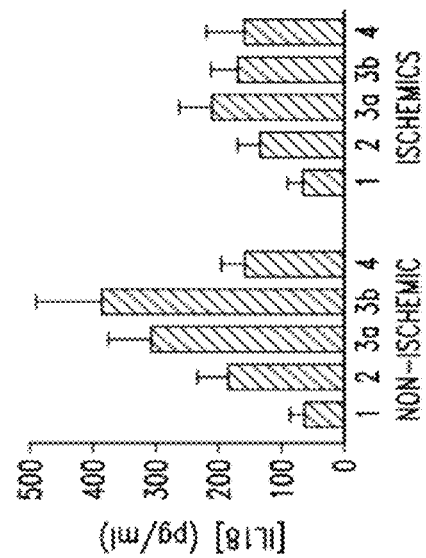
Figure 3C:
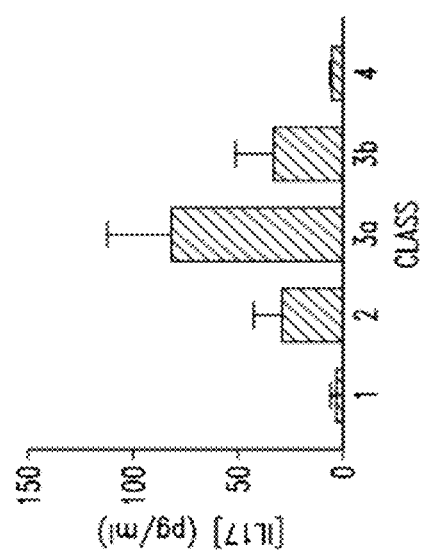
Figure 3D:
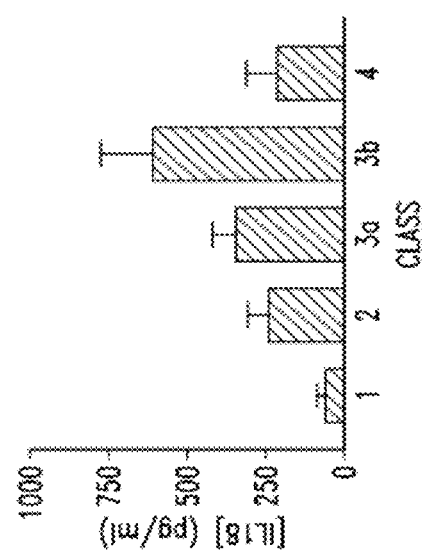

Plasma levels of IL-18 were also elevated in NYHA classes 2, 3a, 3b and 4 (FIG. 3C). Similar to IL-17, this data shows a direct correlation between IL-18 levels and progression of disease up to NYHA class 3b with a decrease in IL-18 in NYHA class 4 (FIG. 3C). When broken down into non-ischemic and ischemic cardiomyopathy, IL-18 levels were elevated in both non-ischemic and ischemic cardiomyopathy for the same NYHA classes (FIG. 3D). Non-ischemic cardiomyopathy patients had comparatively higher levels of IL-18 for NYHA classes 2, 3a and 3b.

This data demonstrates that IL-17 plasma levels can be used as a prognostic indicator of cardiovascular disease and disease severity. Without being bound by theory, the relative expression of IL-17 and IL-18 may be diagnostic of non-ischemic versus ischemic cardiomyopathy (compare FIGS. 3B and 3D). Therefore, assays to detect circulating levels of IL-17 and IL-18 may be used to diagnose cardiovascular disease and qualitatively assess disease severity. Taken together, this data shows IL-17 and IL-18 are implicated in cardiovascular disease and provides a basis for treating cardiovascular disease by administering IL-17 and/or IL-18 antagonists, alone or in combination.

Example 2

Cytokine Profiles of Heart Transplant Recipients

This study shows, inter alia, that IL-17, IL-18 and soluble 4-1BB are elevated in heart transplant recipients that died within 72 hours of transplantation. This data shows that myocardial dysfunction is associated with significantly elevated levels of IL-17, IL-18 and soluble 4-1BB.

Cardiac transplantation remains a major therapeutic modality for patients with end-stage heart failure; however, the number of donor organs significantly limits its availability. This situation is worsened by the fact that around 20% of organ donors have such severe acute myocardial dysfunction associated with brain death that their hearts are unable to be used for transplantation (Hosenpud J D, et al., *Heart Lung Transplant.* 2001, 20(8):805-15). Brain death is a catastrophic event associated with marked activation of the immune system and elevated plasma levels of cytokines such as TNFα and IL6 (Takada, M, et al., *Transplantation* 1998, 65(12):1533-42 and Birks, E J, et al., *Transplant Proc.* 2001; 33(5):2749-51). Cytokines are critical regulators of the T-helper 1 (Th1) and Th2 T-cell responses (Neurath, M F, et al., *Nat Med.* 2002, 8(6):567-73). The Th1 response results in pro-inflammatory cytokine release characterized by macrophage activation and, if unopposed, may result in tissue damage. The Th2 response results in a humoral immune response that in general opposes the Th1 response.

We hypothesized that death early after heart transplantation could be due to donor derived factors impacting on heart function either directly or indirectly, for example by initiating an acute rejection episode, ultimately resulting in myocardial dysfunction. To test this hypothesis we obtained plasma from two groups of heart transplant donors (as described above). Group A comprised samples from 16 organ donors where the recipient had an uneventful postoperative course and survived greater than 1 year. Group B samples were obtained from 14 donors where the recipients died within 72 hours of transplantation with myocardial dysfunction refractory to maximal medical therapy. The circulating levels of the Th1 (pro-inflammatory) cytokines interferon gamma (IFNγ), IL-12, IL-15, IL-17 and IL-18 along with the Th2 (anti-inflammatory) cytokines IL-4, IL-5, IL-10 and IL-13 were measured. Cytokine levels were determined using LUNIMEX® technology (Upstate, Waltham, Mass.), QUANTIKINE® ELISA kits (R&D Systems) or a custom made ELISA for soluble 4-1BB (using capture and detection antibodies, also from R&D systems). The control group consisted of 21 healthy patients with echocardiographically normal myocardial function undergoing routine coronary artery bypass graft surgery. The circulating Th2/Th1 ratio was obtained by dividing the sum of the Th2 cytokines by the sum of Th1 cytokines, both in pg/ml. In addition, as a potential marker of T-cell interaction with antigen presenting cells, we also measured the level of the soluble receptor 4-1BB. 4-1BB is present on activated T-cells and 4-1BB ligand (4-1BB-L) is present on antigen presenting cells; engagement of 4-1BB by 4-1BB-L acts as a co-stimulatory signal (Kwon, B., et al., *Mol Cells.* 2000; 10(2):119-26). Inflammatory mediator levels in groups A and B were compared to those in 21 non-brain dead control subjects.

Figure 9:
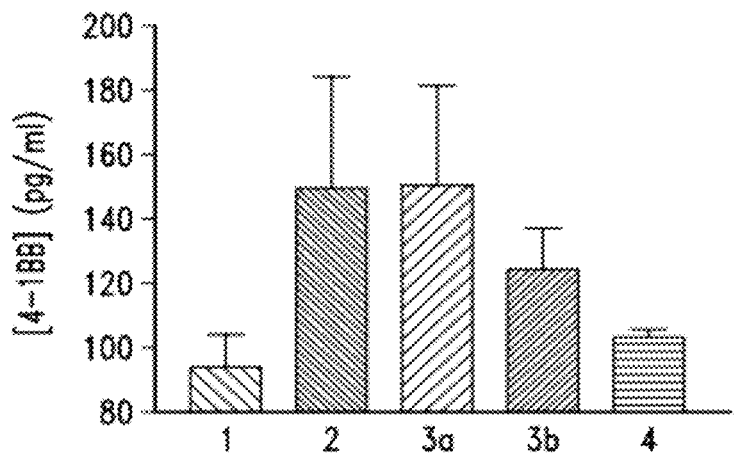
FIG. 9 illustrates that 4-1BB plasma levels were significantly elevated in patients with heart failure compared to normal subjects thereby suggesting activation of this system in human heart failure.

FIG. 9 shows that 4-1BB levels were significantly elevated in the patients with heart failure compared to normal subjects suggesting activation of this system in human heart failure, in common with rheumatoid arthritis patients (Eur J Immunol. 1998 January; 28(1):290-5).

As shown in the Table 2, plasma samples from brain dead organ donors, where the recipients had an uneventful outcome post-transplantation (group A), contained significantly elevated levels of the Th2 cytokines IL-4, 10 and 13, along with the Th1 cytokines IFNγ, IL-12, 17 and 18 compared to control subjects. Overall, however, this maintained a circulating Th2/Th1 ratio of 0.32, which was not significantly different from 0.45 seen in control subjects. In group B, where the recipients died within 72 hours of transplantation, the Th2 cytokines IL-4 and 13 were unchanged from control levels, IL-10 was elevated compared to control subjects, but significantly reduced compared to Group A samples. IFNγ was elevated compared to control samples and IL-12 was unaltered. However, marked elevations in the levels of IL-17 and IL-18 were identified, resulting in a reduction in the Th2/Th1 ratio to 0.028 ($P<0.05$). Whilst soluble 4-1BB levels were similar in control and group A patients, significantly elevated levels were found in the plasma of group B patients (see FIG. 4).

These data identify a change in the circulating cytokine balance towards a pro-inflammatory (Th1) environment in the plasma of donors associated with early recipient death post-transplantation. Elevations in the levels of IL-17 and IL-18 are predominantly responsible for this. IL-18 utilizes the same signaling pathway as IL-1 and lipopolysacharide (Sims, J E, *Curr Opin Immunol.* 2002; 14(1):117-22), both of which are negatively inotropic. IL-17 induces nitric oxide production from a variety of cells, and also stimulates production of a number of cytokines and prostaglandins from a variety of cell types. The elevated levels of IL-17 and IL-18 seen, in particular, in group B patients could well contribute to the adverse recipient outcome early after transplantation. Significantly elevated levels of soluble 4-1BB were also observed in the plasma samples of donors in group B, suggesting that enhanced antigen presenting cell:T-cell interaction may occur in these patients.

Analysis of donor cytokine expression and levels of molecules such as IL-17, IL-18 and 4-1BB is valuable in identifying hearts from donors that may require intensive supportive therapy post-transplantation, or indeed that should not be used for transplantation. These data emphasize the importance of immune activation in brain death, its potential impact on outcome post-transplantation and the idea that therapies aimed at altering the donor cytokine balance may result in improved recipient outcome. These results suggest that elevated 4-1BB, as well as other cytokines such as IL-17 and IL-18, primes the heart for rejection in a recipient soon after transplantation or that these 4-1BB, IL-17 and/or IL-18 may directly mediate impaired myocardial performance. Thus, the studies presented herein demonstrate that IL-17, IL-18 and 4-1BB are implicated in cardiovascular disease and provides a basis for treating cardiovascular disease by administering IL-17, IL-18 and/or 4-1BB antagonists, alone or in combination.

TABLE 2

|  | IL-4 | IL-5 | IL-10 | IL-13 | IFNγ | IL-12 | IL-15 | IL-17 | IL-18 | 4-1BB |
|---|---|---|---|---|---|---|---|---|---|---|
| Control mean | 2.6 | 0.9 | 1.7 | 1.9 | 1.9 | 10.4 | 38.7 | 1.1 | 68.1 | 30 |
| (SE) | (0.9) | (0.3) | (0.3) | (0.7) | (0.4) | (4.7) | (13.85) | (0.5) | (23) | (20) |
| Group A mean | 14 | 2.4 | 19.9 | 8.8 | 20.7 | 41.5 | 8.6 | 18 | 186 | 90 |
| (SE) | (5.3) | (1.6) | (4.8) | (5.9) | (8.6) | (31.6) | (3.1) | (18) | (50) | (80) |
| Group B mean | 3.5 | 0.45 | 7 | 1.1 | 8.4 | 7.4 | 5.4 | 292 | 373 | 420 |
| (SE) | (0.4) | (0.1) | (2) | (0.2) | (1.5) | (1.9) | (1.8) | (70) | (51) | (170) |

Example 3

IL-17 Levels and Heart Chamber Dimensions

These studies demonstrate that exposure to IL-17 results in a drop in left ventricle dimensions.

Figure 4:
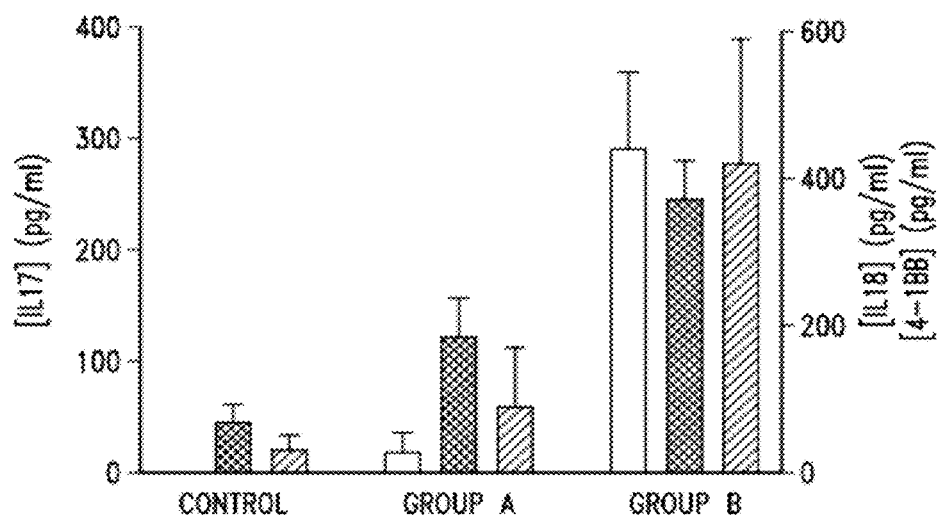
FIG. 4 illustrates the plasma levels of IL-17 (open bars) and IL-18 (closed bars) and 4-1BB (hatched bars) of control subjects or donors with favorable recipient outcome (group A) or adverse recipient outcome (group B) post-transplantation.

Female C57/Black6 mice were anethetised with avertin. A midline laparotomy was performed and the inferior vena cava was cannulated. A base line echocardiogram was then performed. Human IL-17 (200 ng) was then administered in a bolus of 200 ml of PBS (pH 7.4). At the indicated time points the echocardiogram was repeated and left ventricular internal diameter in diastole and systole were determined As shown in FIG. 4, these data demonstrate that IL-17, following acute administration, results in diminished chamber dimensions with maintained ejection fraction. The reduction in diastolic dimensions may suggest that IL-17 plays some part in mediating diastolic dysfunction, though it may also be involved in systolic heart failure. This data suggests IL-17 is implicated in cardiovascular disease and provides a basis for treating cardiovascular disease by administering IL-17 antagonists.

Example 4

IL-17 and IL-18 Levels are Elevated in a Murine Myosin-Induced Myocarditis Model This study shows that IL-17 and IL-18 are elevated in an experimental autoimmune myocarditis (EAM) model, which shows a similar course of disease as seen in humans. The terms "EAM" and "cardiac myosin-induced myocarditis" are used interchangeably to describe similar models.

It is well known in the art that myocarditis is associated with an autoimmune process in which cardiac myosin is a major autoantigen. Cardiac myosin-induced myocarditis histologically resembles viral-induced myocarditis. It is generally agreed that both antibody and T-cells are implicated in inflammatory heart disease, such as myocarditis. Experimental autoimmune myocarditis models that mimic the disease in humans have been developed in a variety of rodent models and are well known in the art (see, for example, in A/J mice: Neu, N, et al., *J. Immunol.* 1987, 139:3630-3636 and Smith, S C, et al., *J. Immunol.* 1991, 147:2141-2147; in BALB/c mice: Pummarer, C L, et al., *J. Clin. Invest.* 1996, 97:2057-2062 and Liao, L, et al., *J. Clin. Invest.* 1993, 92:2877-2882; and in Lewis rats: Kodama, M, et al., *Clin. Immunol Immunopath.* 1991, 57:250-262 and Wegmann, K W, et al., *J. Immunol.* 1994, 153:892-900).

It has been shown in the A/J mouse EAM model that blocking IL-4 with anti-IL-4 monoclonal antibody reduced the severity of EAM by shifting the immune response from a Th2-like response to a Th1-like response with a concomitant increase in INF-γ production, which suggested INF-γ limits the disease. Blockade of INF-γ was shown to exacerbate disease, thereby establishing the basis for using an INF-γ knockout (INF-γ$^{-/-}$) in a EAM model (Afanasyeva, M, et al., *Am J Pathol* 2001, 159:193-203).

Autoimmune myocarditis was induced in mice by immunizing BALB/c and INF-γ$^{-/-}$ knockout mice with 200 ug a-myosin heavy chain plus MTB (mycobacterium tuberculosis was included at 5 mg/ml H37Ra; Difco/Bectin Dickinson, Franklin Lakes, N.J.) and Pertussis toxin at 500 ng (List biological laboratories, Campbell, Calif.) intraperitoneally in a volume of 400 ul. Interferon gamma-deficient mice were obtained from Jackson Laboratories, Bar Harbor, Me. BALB/c and INF-γ$^{-/-}$ were boosted on Day 7 by immunization with myosin formulated in Complete Freund's Adjuvant (CFA) with omission of Pertussis toxin. Animals were sacrificed at days 35, 55 or 85 and the following analysis were preformed: histology, anti-myosin antibody titre, serum cytokine profile and antigen specific T-cell proliferation assays. Some animals underwent echocardiography.

BALB/c and INF-γ$^{-/-}$ mice that were immunized with a-myosin heavy chain developed antibodies against myosin peptide as measured by standard ELISA techniques. Myosin-immunized BALB/c and INF-γ$^{-/-}$ mice developed myocardial lesions, with the knockout mice showing an increase in lesion number and severity over negative controls and BALB/c mice. In addition, INF-γ knockout mice showed a greater degree of myocardial inflammation and fibrosis, as well as a greater percent increase in heart/body weight ratio over negative controls and BALB/c mice. Mysoin-specific T-cell proliferation responses were shown in myosin-immunized INF-γ knockout and BALB/c mice, as measure by standard thymidine incorporation assays.

Figure 5:
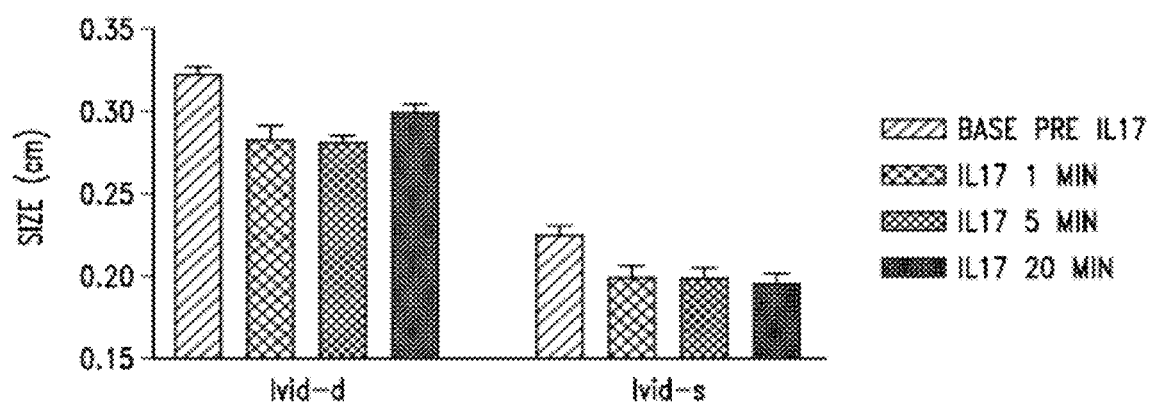
FIG. 5 illustrates the effect of administering IL-17 on heart chamber dimensions over time.

Furthermore, plasma levels of IL-17 and IL-18 were elevated in the cardiac myosin-induced myocarditis model. IL-17 and IL-18 were assayed using commercially available ELISA kits, such as described in Example 1. As shown in FIG. 5A, IL-17 levels were markedly increased in INF-γ$^{-/-}$ mice at day 28 and 35 post immunization. Plasma levels of I1-18 rose sharply at 9 days post immunization and remained elevated out to day 28 (FIG. 5B). This data clearly shows that circulating plasma levels of IL-17 and IL-18 are elevated in the myosin-induced model and that IL-17 and IL-18 are associated with myocarditis immunopathology. This data provides a basis for treating cardiovascular disease by administering IL-17 and/or IL-18 antagonists, alone or in combination.

Example 5

IL-17 Expression in T-Cells in the Myosin-Induced Myocarditis Model

These experiments demonstrate that IL-17 is expressed at high levels in T-cell populations isolated from EAM mice. Details of the EAM model are provided in the previous Example.

Figure 6A:
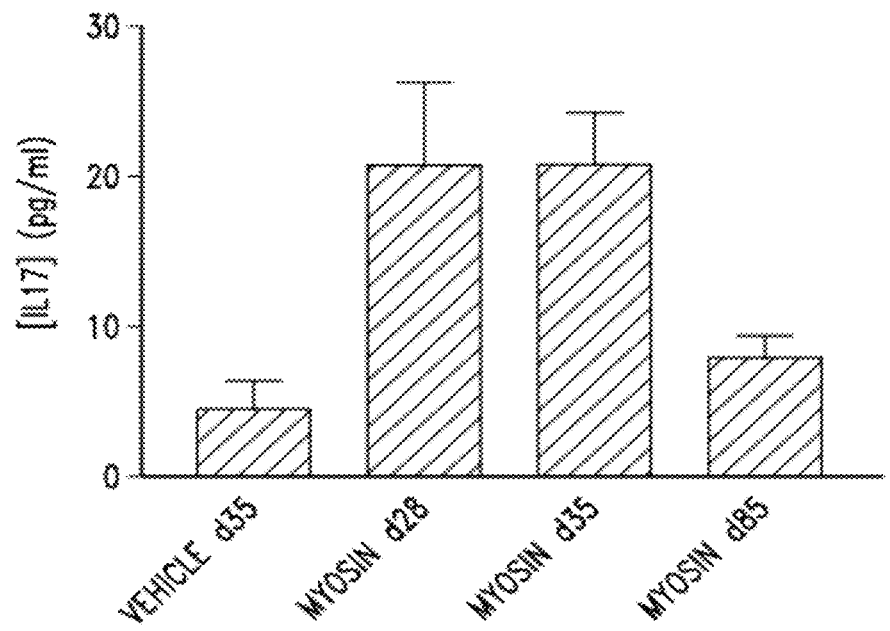
FIGS. 6A and 6B depict IL-17 and IL-18 plasma levels in IFN-$\gamma^{-/-}$ mice immunized with cardiac myosin peptide that induces an inflammatory myocarditis and cardiomyopathy.

T-cells were isolated from EAM mice using standard techniques and stimulated with anti-CD3 antibody. As shown in FIG. 6A, the animal immunized with cardiac myosin having histologically demonstrated cardiopathology (animal B) had significantly higher expression levels of IL-17 over negative controls (animals C and D), as well as an animal immunized with cardiac myosin, but not exhibiting signs of cardiopathology (animal A).

Figure 6B:
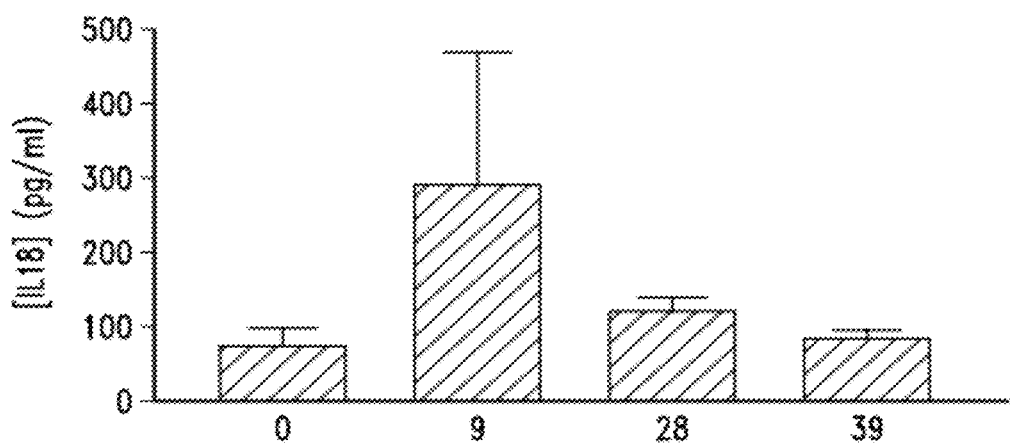
Figure 7A:
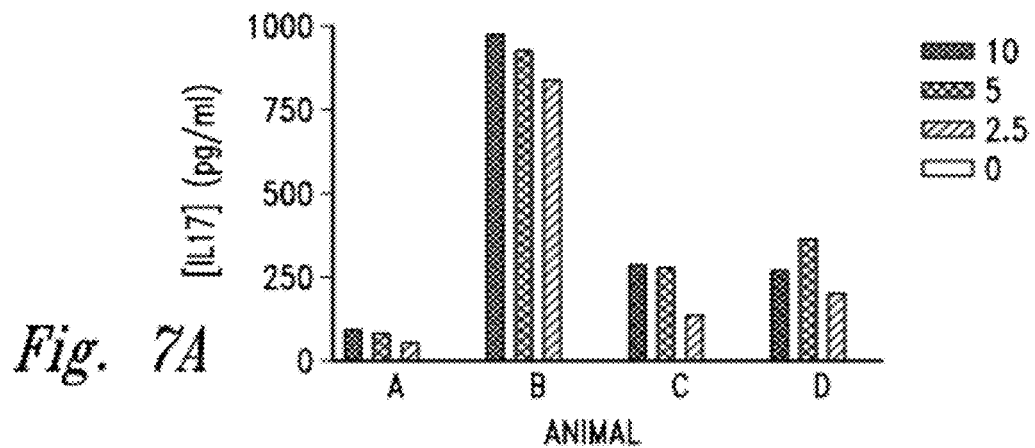
FIGS. 7A through 7C.
Figure 7B:
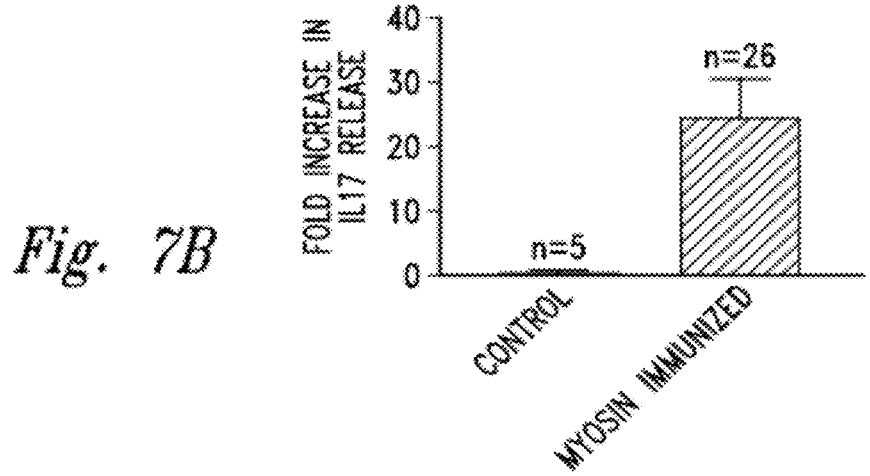
Figure 7C:
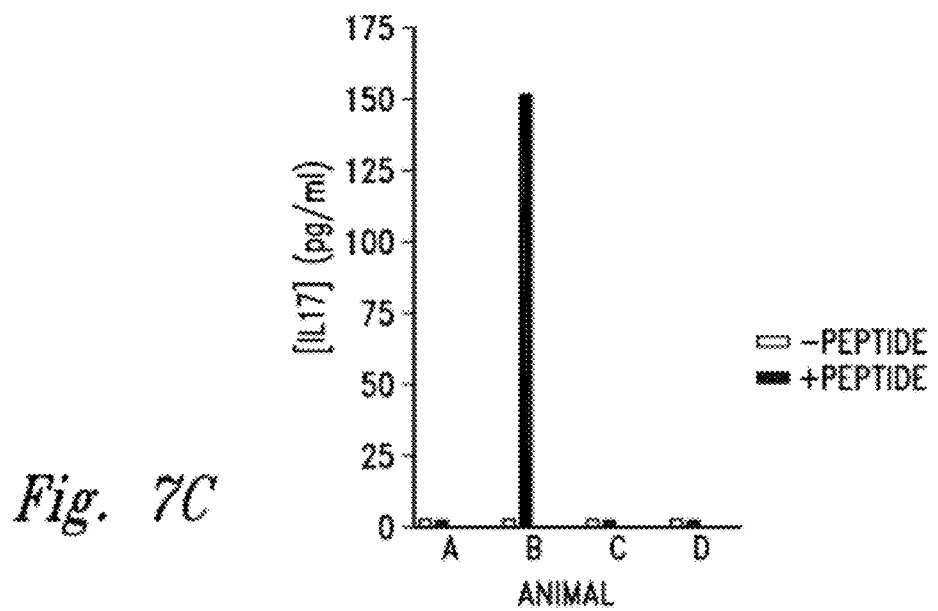

IL-17 expression in EAM mice was shown to be a myosin-specific T-cell response. On average, IL-17 levels were approximately 25 fold higher in T-cells isolated from animals immunized with cardiac muyosin and exposed to antigen presenting cells fed myosin over antigen presenting cells not exposed to myosin (FIG. 6B).

In a related study, the antigen presenting cells were exposed to a-myosin peptide rather than being fed whole a-myosin protein. As in the previous study, T-cells from the animal immunized with cardiac myosin and having histological evidence of cardiopathology (animal B) released surprisingly high levels of IL-17 in response to antigen-specific stimulation by peptide-pulsed antigen presenting cells (FIG. 6C). Without being bound by theory, this study suggests that activated (likely CD4+) T-cells when encountering antigen presenting cells bearing heart antigens proliferate and release IL-17. The released IL-17 may contribute to inflammatory cell infiltration into the heart, direct myocardial damage or may also have a direct depressant effect on heart function.

Example 6

IL-18 and IL-18 Binding Protein Plasma Levels in Acute Coronary Syndrome Patients These studies show that IL-18 is elevated in patients having acute coronary syndrome and that IL-18 correlates with increased risk for major adverse cardiac events (MACEs).

Patients were stratified into three patient groups: those having stable coronary artery disease (CAD), acute coronary syndrome (ACS) with cardiac troponin I (cTnI) plasma levels less than 0.4 ng/ml or acute coronary syndrome (ACS) with cardiac troponin I (cTnI) plasma levels greater than 0.4 ng/ml. The CAD group included patients having stable angina and the ACS group included patients having unstable angina, non-ST elevation myocardial infarction, ST elevation myocardial infarction and sudden ischemic death.

Cardiac troponin I is recognized as a reliable biochemical marker for the diagnosis of myocardial injury, such as myocardial necrosis resulting from ischemia. Elevated cardiac troponin I is strongly associated with a high-risk profile for short and long term adverse cardiac events. Measuring the relative levels of cardiac troponin I provides a reliable stratification of risk and prediction of outcome for acute coronary syndrome patients. In this study, patients having a cardiac troponin I level of greater than 0.4 ng/ml suffered a serious adverse cardiac event, often resulting in death, within ten days.

Cytokine levels were measured in plasma samples from patients from each of the three groups essentially as described in the protocols provided in commercially available ELISA kits (see, for example, QUANTKINE® R&D Systems, Minneapolis, Minn., which provides assays for the quantitative determination of human IL-18). IL-18 Binding Protein A (IL-18Bpa) was measured using commercially available antibodies from R&D. Plates were coated with a capture antibody. Samples were then added to wells and incubated at room temperature for 2 hours. Wells were then washed, incubated with a biotinylated detection antibody and the immunoreaction detected using standard techniques and TMB as chromogen. IL-18 Binding Protein produced in house was used as standard.

Figure 8A:
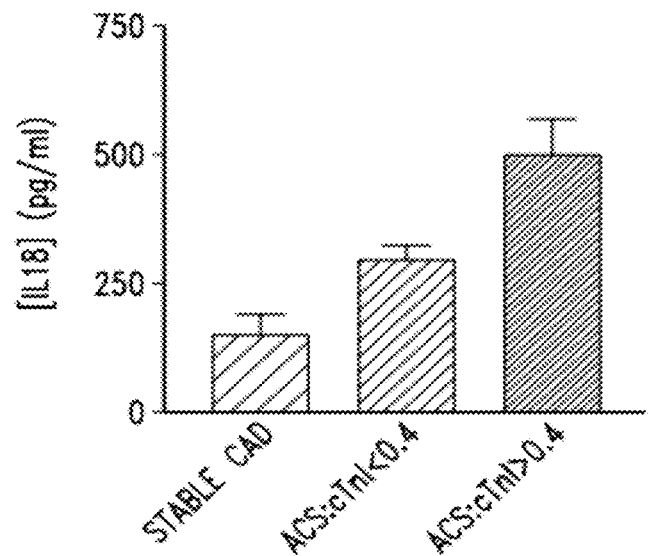
FIGS. 8A and 8B show IL-18 levels and the ratio of IL-18 to IL-18 Binding Protein, respectively, in patients stratified into three patient groups: those having stable coronary artery disease (CAD), acute coronary syndrome (ACS) with cardiac troponin I (cTnI) plasma levels less than 0.4 ng/ml or acute coronary syndrome (ACS) with cardiac troponin I (cTnI) plasma levels greater than 0.4 ng/ml.
Figure 8B:
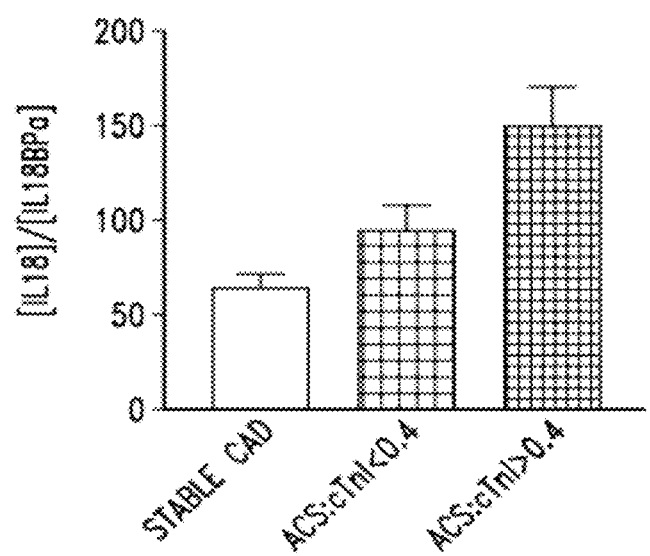

As shown in FIG. 8A, plasma levels of IL-18 was elevated in the ACS group having a cTnI level of less than 0.4 ng/ml, and more significantly, IL-18 levels were even higher in patients in the ACS group having a cTnI level of greater than 0.4 ng/ml. FIG. 8B shows the ratio of IL-18:IL-18 BPa among the three groups and illustrates that IL-18 Binding Protein levels are not elevated in either the ACS groups, which demonstrates that the elevated IL-18 levels are unopposed by this immune mechanism.

This data shows that circulating levels of IL-18 are elevated in ACS patients at high risk of subsequent major adverse cardiac events and that IL-18 Binding Protein levels do not rise concomitantly to counteract the immune response. Thus, IL-18 is implicated in cardiovascular disease and provides a basis for treating cardiovascular disease by administering IL-18 antagonists, alone or in combination with other antagonists described herein.

In addition, elevated IL-18 levels correlate with elevated cTnI levels and disease progression or disease severity. Therefore, IL-18 may also serve as a surrogate marker for increased risk for serious adverse cardiac events. Embodiments of the present invention include diagnostic assays for determining the level of IL-18 in patients having cardiovascular disease for the purpose of assessing disease progression or severity.

Example 7

4-1BB Ligand Knockout Mice are Protected in Adriamycin®-Induced Murine Model of Dilated Cardiomyopathy These experiments demonstrate that 4-1BB-L knockout mice (4-1BB-L$^{-/-}$ or 4-1BB-L KO) showed no mortality and had a delayed onset of cardiac dysfunction in an Adriamycin®-induced murine model of dilated cardiomyuopathy.

Adriamycin® (Doxorubicin Hydrochloride, an anthracycline antibiotic- Pharmacia, Milan, Italy) has been shown to exhibit myocardial toxicity resulting in congestive heart failure, i.e., ischemic or dilated cardiomyopathy. Many animal models have been developed over the years using using Adriamycin® and are well-known in the art.

Male 4-1BB-L$^{-/-}$ (53 days old) and C57B1/6 (59 days old, Taconic, Germantown, N.Y.) were used in the study. Mice were anesthetized with 100-150u1 ketamine-xylazine, weighed and ear tagged. Baseline echocardiographic (echo) measurements were taken from the parasternal long axis view while the mouse lay prone on a 1cm thick agarose gel pad (Sonos5500- Philips Co., with a S12 probe and a Instec heated microscope stage with 1 cm thick 1% agarose gelpad). Measurements taken included: AoR diameter, LA dimension, ACS, RVd, IVSd, LVIDd, LVPWd, IVSs, LVIDs, LVPWs, and HR. Echo evaluations were perfomred at weeks 0, 2.5, 5 and 7 and a phenotype assigned to each mouse based on the weekly echo measurements. Fractional shortening (FS) was calculated by the echo instrument. Measurements were normalized between mice by obtaining a PSLA image where the AoR and LA dimensions had a 1:1 ratio. Additionally, LV dimensions were taken from a Mmode image obtained by dissecting the LV perpendicularly through the PW, just distal to the tips of the mitral valve leaflets (sweep speed 100). Diastolic measurements were taken at the peak of the QRS complex of the EKG, while systolic measurements were recorded at the point of maximal contraction of the PW. All measurements were recorded onto optical disk, videotaped and printed.

After all echo measurements were obtained, the mice were injected retroorbitally with 22.5 mg/kg Adriamycin® (Sigma-Aldrich/Fluka, St. Louis, Mo.) and allowed to recover from anesthesia. Adriamycin was prepared from a powdered stock by dissolving 10 mg in 1 ml sterile water for a stock concentration of 10 mg/ml. Further dilutions were made with sterile saline. Solutions were made on the day of injection. The mice that received a dose of 22.5 mg/kg were injected with 150 ul of a 3.75 mg/ml working dilution for a total dose of 0.5625 mg. Body weights were recorded daily.

If an animal was sacrificed due to a greater than 15% loss in body weight or at the end of the study, the hearts were harvested and fixed in 10% NBF (neutral buffered formalin). Briefly, thoracic insicions were made to expose the heart. Using a 27 g needle, 1M KCl (final concentration=50 mM) was injected directly into the heart to stop the hearts in diastole; PBS was then injected directly into the heart to flush blood out of the chambers. The heart was carefully removed, rinsed in PBS and placed into 10% NBF.

As mentioned above, a phenotype was assigned to each mouse based on the echo results and each mouse was classified according to the degree of cardiotoxicity into stages I, II, III or IV. The following criteria was used to phenotype the mice: Diastolic Dysfunction: LVIDd % Δ and LVIDs % Δ reduced >10% and FS same or increased; Systolic Dysfunction: LVIDd % Δ plus LVIDs % Δ increased >25% and FS reduced >12%; Diastolic and Systolic Dysfunction: LVIDd % Δ plus LVIDs % Δ reduced >20% and FS reduced >12%; Dilated: LVIDd % Δ>12% and LVIDs % Δ>12%.

4 of 10 wild type mice died between 8 and 10 days after Adriamycin® injection. These deaths are considered chronic heart failure deaths. Wild-type mice challenged with Adriamycin® had an approximate 2-week mortality rate of 50% and approximately 66% of the mice exhibited evidence of cardiac dysfunction 2 to 2.5 weeks post Adriamycin®-challenge. The wild-type survivors generally showed two phenotypes: (a) systolic dysfunction with LV chamber dilation with diminished ejection fraction (EF), and (b) diastolic disfunction with progressive reduction in chamber dimensions with diminished ventricular filling but maintained EF.

In contrast, no mortality was observed in the 4-1BB-L KO mice and none of the 4-1BB-L KO mice showed signs of the most severe cardiotoxicity following Adriamycin® challenge compared to 59 to 71% of wild type mice.

TABLE 3

|  | 4-1BB-L KO | Wild Type Bl6 | Historical Bl6 cntls |
|---|---|---|---|
| No Dysfunction (Class I) | 7/14 (50%) | 2/7 (29%) | 9/22 (41%) |
| Transient Dysfunction (Class II) | 1/14 (7%) | 0/7 (0%) | 1/22 (5%) |
| Progressive Dysfunction (Class III) | 6/14 (43%) | 1/7 (14%) | 5/22 (23%) |
| Chronic Failure (Class IV) | 0/14 (0%) | 4/7 (57%) | 7/22 (32%) |
| Total cardiotoxicity | 7/14 (50%) | 5/7 (71%) | 13/22 (59%) |

These results demonstate that the 4-1BB and 4-1BB-L receptor:ligand pair are implicated in immune responses associated with cardiovascular disease, and in particular play a role in ischemic cardiomyopathy. These data establish a sound basis for preventing, treating or alleviating the symptoms of cardiovascular disease, and in particular ischemic cardiomyopathy, by antagonizing the interaction of 4-1BB and 4-1BB-L. Furthermore, these results demonstrate that antagonizing 4-1BB-L:4-1BB interactions reduces Adriamycin®-induced cardiotoxicity. Therefore, 4-1BB, CD30 and/or OX40 antagonists, may be used prior to or in combination with chemotherapeutic compositions in order to reduce the cardiotoxic side-effects of such chemotherapeutics.

Example 8

4-1BB is Expressed by Damaged Cardiac Interstitial Cells and 4-1BB/4-1BBL Signaling Contributes to Adriamycin®-Induced cardiomyopathy in Mice Co-stimulatory pathways have been implicated in myocarditis and dilated cardiomyopathy in mice and humans. Expression of co-stimulatory ligands is increased on cardiac myocytes, while the receptors are expressed on infiltrating immune/inflammatory cells (Seko et al, 2002; Seko et al, 2001; Seko et al, 1998). The aim of these studies was to determine the role of the 4-1BB/4-1BBL co-stimulatory pathway in the onset and progression of Adriamycin®-induced cardiomyopathy, which is not associated with the extensive inflammatory infiltrate seen with other forms of dilated cardiomyopathy. These studies demonstrate a role for the 4-1BB/4-1BBL immune co-stimulatory pathway in Adriamycin®-induced cardiomyopathy, deomonstrated a novel cardiac expression pattern of 4-1BB and implicated apoptosis as a mechanism of co-stimulatory contribution to Adriamycin®-induced cardiomyopathy.

1. 4-1BB and 4-1BBL Expression is Up-Regulated in Adriamycin®-Treated Myocardium.

Six-week old C57Bl/6 mice were injected retrorbitally with 45 mg/kg Adriamycin® and the hearts were collected at 0, 24, 48, 72, and 96 hrs post treatment. Immunohistochemical staining on cryo-sections for CD45 was performed to detect inflammatory infiltrate, as well as staining for 4-1BB. Immunohistochemistry of CD45 did not recognize positive cells in Adriamycin®-treated myocardium. As positive control, CD45 positive cells were detected in spleen. While no inflammatory infiltrate was observed in the Adriamycin®-cardiomyopathy, we found expression of 4-1BB induced on 1-5% of cardiac interstitial cells within 2 days after Adriamycin® administration. As a percentage of animals demonstrating 4-1BB positive cells, 50% mice were positive for 4-1BB in myocardium at 48 hrs and 75% at 72 hrs. In immunohistochemical analysis, 4-1BBL increased in positivity after Adriamycin® treatment. Leukocyte counts in wild type and 4-1BBL−/− demonstrated similar level of neutrophils, monocytes and lymphocytes in peripheral blood, indicating the improvement of cardiac function by loss of 4-1BBL is unrelated to hematopoietic and inflammatory changes.

2. Treatment with Agonistic anti-4-1BB Antibody (M6) Accelerated Cardiac Dysfunction and m4-1BB-Fc Delayed and Reduced Cardiac Dysfunction.

An agonistic antibody to 4-1BB (M6) accelerated and exacerbated cardiac dysfunction in an Adriamycin® challenge model. In contrast, m4-1BB-Fc, which is a soluble decoy receptor for 4-1BBL, delayed and reduced cardiac dysfunction.

Figure 10:
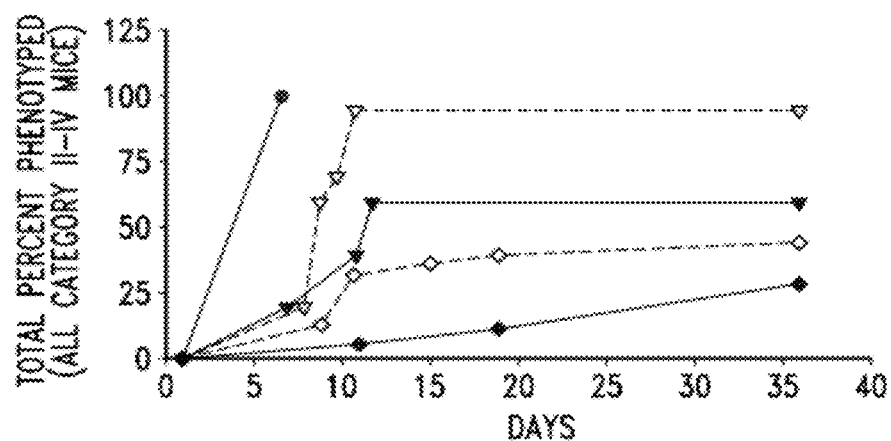
FIG. 10 represents a dose-response of Adriamycin® in wild type and 4-1BBL−/− knock out mice. At 22.5 mg/kg and 25 mg/kg, the percentage of Adriamycin®-induced cardiac dysfunction was decreased in 4-1BBL−/−. At high dosage (30 mg/kg), no difference was observed between wild type and 4-1BBL−/− group.
Figure 11:
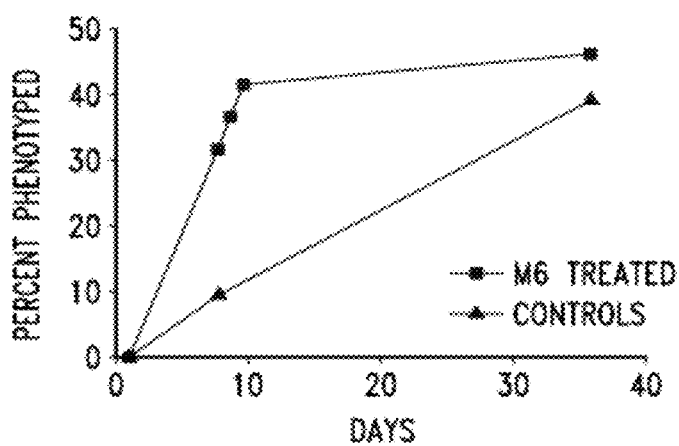
FIG. 11 is a graph showing 4-1BB activating antibody (M6) administered 3, 6, 9 days after Adriamycin® treatment. The onset of dysfunction was accelerated by M6 antibody, but the final penetrance was similar to control group.

100 ug/mouse of agonistic antibody to 4-1BB (M6, lot 9159-069 from Amgen Hybrodima Group) was administered IP on days 0, 3 and 6. Day 0 being the date of Adriamycin® challenge. NaCl controls were included for each treatment regimen. Wild type (WT), 4-1BBL KO, or WT mice treated with an activating antibody to 4-1BB (M6) were challenged with Adriamycin® in doses ranging from 22.5 to 45 mg/kg by retroorbital injection, immediately following baseline echocardiographic (ECHO) analysis of cardiac function. Serial ECHO analysis was performed at 1, 2.5 and/or 5 weeks after Adriamycin® challenge. In one study, WT and 4-1BBL KO mice were challenged with Adriamycin® (45 mg/kg) and hearts were collected at 24, 48 and 72 hours. TUNEL positivity by IHC and caspase 3 activation by western blot were determined as indices of apoptosis. 4-1BBL KO mice had improved cardiovascular function and decreased penetrance of cardiomyopathy, as evaluated by M-mode echocardiography compared to WT controls (see Table 4, below and FIG. 10). For Table 4, combination of stroke volume, systolic, diastolic end volume was used to categorize functional phenotype. 4-1BBL KO mice have reduced cardiotoxicity and improved function post-Adriamycin®. Treatment of WT C57B1/6 mice with the 4-1BB activating antibody (M6) accelerated the onset of ADR-induced cardiomyopathy (FIG. 11).

TABLE 4

| Phenotype | WT | 4-1BB-/- KO | M6 antibody | M4-1BB-Fc |
|---|---|---|---|---|
| Normal | 48% | 79% | 53% | 70% |
| Dysfunction | 52% | 21% | 47% | 30% |

3. Apoptosis was Increased in Adriamycin Myocardium.

C57B1/6 mice were treated with 45 mg/kg adriamycin. Heart tissues were harvested at different time points and analyzed for TUNEL positive nuclei. TUNEL positivity increased at 48 hrs and peaked at 72 hrs. Whole heart digests were collected from Adriamycin®-treated mice were stained with troponin-I(TnI) antibody and FITC conjugated secondary antibody and propidium iodide. TnI positive cells were analyzed for sub-G1 DNA fragments. In WT mice, cardiac TUNEL positivity increased at 48 and 72 hr after Adriamycin® injection.

Cardiac apoptosis, measured by TUNEL and sub-G1 DNA, was increased 3 days after Adriamycin®, concomitant with the increased expression of 4-1BB on interstitial cells. Chronic ongoing apoptosis, determined 5 weeks after Adriamycin® challenge when cardiac dysfunction is maximal in wild type but largely absent in 4-1BBL-/- mice, was lower in 4-1BBL-/- mice (1.5-fold vs baseline), compared to WT mice (4 fold). In a separate study, caspase 3 activation, determined by Western blot, was increased at 48 to 72 hrs post-Adriamycin® (45 mg/kg). In contrast, Adriamycin® did not induce caspase 3 cleavage in 4-1BBL-/- myocardium. Determined by western blot, Adriamycin® reduced phosphorylation of Akt in wild type but not 4-1BBL-/- hearts. Phosphorylation of JNK and p38 was not impacted by Adriamycin®. Therefore, 4-1BB/4-1BBL immune co-stimulatory pathway contributes to Adriamycin®-induced cardiomyopathy, possibly through modulation of Akt signaling to regulate In conclusion, 4-1BBL deficient mice and 4-1BBL decoy receptor-treated mice conferred partial resistance to adriamycin induced cardiac damage, whereas 4-1BB activating antibody accelerated onset of damage, implying the contribution of 4-1BB to Adriamycin® effects in heart. Apoptosis, measured by TUNEL, sub-G1 DNA and activated caspase-3, was increased in Adriamycin®-treated wild type myocardium, but reduced in 4-1BBL-/-. Phosphorylation of Akt was selectively suppressed by Adriamycin®, but maintained by loss of 4-1BBL, indicating the modulation of apoptosis by co-stimulatory pathway in heart is possibly through Akt, but not Jnk and p38 signaling. The consistency of decreased index of apoptosis and the improved cardiac function in 4-1BBL-/- suggests apoptosis play a pivotal role in Adriamycin®-induced cardiac deficiency.

Example 9

Antibodies Generated against IL-17, IL-17R, IL-18, IL-18R, 4-1BB, 4-1BB-L, CD30, CD30-L AND CD39

Monclonal and/or polyclonal antibodies were generated against IL-17, IL-17R, IL-18, IL-18R, 4-1BB, 4-1BB-L, OX40, CD30, CD30-L and CD39 using standard techniques. One or more of these antibodies, or other antibodies directed against IL-17, IL-17R, IL-18, IL-18R, 4-1BB, 4-1BB-L, OX40, OX40-L, CD30, CD30-L or CD39 may be used as an antagonist for the treatment of cardiovascular disease Immunogens used to generate antibodies included purified polypeptides, fragment thereof such as the extracellular domain, Fc-fusion proteins of the extracellular domains, and leucine-zipper derivatives of the extracellular domains (refer to Table 3 below). Of course, other forms of the proteins could be used to generate antibodies, such as any immunogenic fragment, alone or fused with other proteins. In addition, DNA encoding a polypeptide can be used as an immunogen, for example, DNA may be given intradermally (Raz et al., 1994, *Proc. Natl. Acad. Sci. USA* 91: 9519) or intamuscularly (Wang et al., 1993, *Proc. Nati. Acad. Sci. USA* 90: 4156); saline has been found to be a suitable diluent for DNA-based antigens, or by other similar techniqes, as reviewed by Pardoll and Beckerleg in *Immunity* 3: 165, 1995.

In general, the antibodies were generated by the following method: rodents (BALB/c mice or Lewis rats, for example) were immunized with the polypeptide immunogen emulsified in an adjuvant (such as complete or incomplete Freund's adjuvant, alum, or another adjuvant, such as Ribi adjuvant R700 (Ribi, Hamilton, Mont.)), and injected in amounts ranging from 10-100 micrograms subcutaneously or intraperitoneally. Ten days to three weeks days later, the immunized animals were boosted with additional immunogen and periodically boosted thereafter on a weekly, biweekly or every third week immunization schedule.

Serum samples were periodically taken by retro-orbital bleeding or tail-tip excision to test for polypeptide-specific antibodies by dot-blot assay, ELISA (enzyme-linked immunosorbent assay), immunoprecipitation, or other suitable assays, such as FACS analysis of antibody binding to its original immunogen. Following detection of an appropriate antibody titer, positive animals were provided one last intravenous injection of respective immunogen in saline. Three to four days later, the animals were sacrificed, spleen cells harvested and fused to a murine myeloma cell line, e.g., NS1 or preferably P3X63Ag8.653 (ATCC CRL-1580). The hybridoma cells were plated in multiple microtiter plates in a HAT (hypoxanthine, aminopterin and thymidine) selective medium to inhibit proliferation of non-fused cells, myeloma hybrids, and spleen cell hybrids.

Positive hybridoma cells were injected intraperitoneally into syngeneic rodents to produce ascites containing high concentrations of monoclonal antibodies. Alternatively, hybridoma cells were be grown in vitro in flasks or roller bottles by various techniques. Monoclonal antibodies were purified by ammonium sulfate precipitation, followed by gel exclusion chromatography. Alternatively, affinity chromatography based upon binding of antibody to protein A or protein G has also been used.

Of course other conventional techniques may be used, such as those described in U.S. Pat. No. 4,411,993. For example, the immunogen preparation, choice of adjuvant and immunization protocol are well known in the art and may be found, for example in *Antibodies*: A Laboratory Manual, Harlow and Land (eds.), Cold Spring Harbor Laboratory Press, Cold Spring Harbor, N.Y., (1988).

TABLE 4

| Molecule | Ab name | Immunogen | Species | Type/Isotype |
|---|---|---|---|---|
| IL-17 | mIL-17-M210 | mCTLA8-Fc | Rat | mAb |
| IL-17 | mIL-17-P1 | mIL-17 | Rabbit | polyclonal |
| IL-17R | hIL-17R-M202 | hIL-17R-Fc (cos) | Mouse | IgG2a |
| IL-17R | hIL-17R-M203 | hIL-17R-Fc (cos) | Mouse | IgG1 |
| IL-17R | hIL-17R-M204 | hIL-17R-Fc (cos) | Mouse | IgG2a |
| IL-17R | mIL-17R-M177 | mIL-17R-Fc | Rat | IgG2a |
| IL-17R | mIL-17R-M178 | mIL-17R-Fc | Rat | IgG2a |
| IL-17RH | mIL-17RH-M561 | mIL-17RH-Fc | Rat | IgG2a |
| IL-17RH | mIL-17RH-M561 | mIL-17RH-Fc | Rat | IgG2a |
| IL-18 | hIL-1R/AcpL-P1 | hIL-1R/AcpL-Fc | Rabbit | Polyclonal |
| IL-18 | mIL-1R/AcpL-P1 | mIL-1R/AcpL-Fc | Rabbit | Polyclonal |
| IL-18R | hIL-18R-M495 | hIL-18R | Rat | IgG2b |
| IL-18R | hIL-18R-M496 | hIL-18R | Rat | undetermined |
| IL-18R | hIL-18R-M497 | hIL-18R | Rat | IgG2b |
| IL-18R | mIL-18R-M375 | mRp1-Fc | Rat | IgG1 |
| IL-18R | mIL-18R-M376 | mIL-1R/RpL-Fc | Rat | IgG2a |

TABLE 4-continued

| Molecule | Ab name | Immunogen | Species | Type/Isotype |
|---|---|---|---|---|
| IL-18R | mIL-18R-M377 | mIL-1R/RpL-Fc | Rat | IgG1 |
| IL-18R | hIl-18R-P1 | h2F1 GST | Rabbit | polyclonal |
| IL-18R | hIl-18R-P1 | sol m2F1 | Rabbit | polyclonal |
| 4-1BB | h41BB-M121 | h4-1BB-Fc | Mouse | mAb/IgG1 |
| 4-1BB | h41BB-M127 | h4-1BB-Fc | Mouse | mAb/IgG1 |
| 4-1BB | h41BB-M135 | h4-1BB-Fc | Mouse | mAb/IgG1 |
| 4-1BB | h41BB-M4 | sol h4-1BB-Fc | Mouse | mAb/IgM |
| 4-1BB | h41BB-M8 | sol h4-1BB-Fc | Mouse | mAb/IgG3 |
| 4-1BB | h41BB-M6 | sol m4-1BB-Fc | Rat | mAb/IgG2a |
| 4-1BB | m41BB-P1 | sol m4-1BB-Fc | Rabbit | polyclonal |
| 4-1BB-L | m41BBL-M520 | m4-1BBL-leuzip | Rat | mAb/IgG2a |
| 4-1BB-L | m41BBL-P2 | flag m4-1BBL | Rabbit | polyclonal |
| CD30 | hCD30-M44 | hCD30-Fc | Mouse | mAb/IgG1 |
| CD30 | hCD30-M67 | hCD30-Fc | Mouse | mAb/IgG1 |
| CD30-L | hCD30L-M80 | hCD30L-Fc/CV-1 | Mouse | mAb/IgG2b |
| CD30-L | hCD30L-M81 | hCD30L-Fc/CV-1 | Mouse | mAb/IgG2b |
| CD30-L | hCD30L-M82 | hCD30L(CHO) | Mouse | mAb/IgG2a |
| CD30-L | mCD30L-M15 | mCD30L(CHO) | Rat | mAb/IgG2a |
| CD30-L | mCD30L-M30 | mCD30L(CHO) | Rat | mAb/IgG2a |
| OX40 | mOX40-M5 | mOX40-Fc | Rat | IgG1 |
| OX40 | mOX40-M6 | mOX40-Fc | Rat | IgG2b |
| CD39 | mCD39-M105 | | Rat | mAb/IgG2a |

What is claimed is:

1. A method of reducing inflammation in cardiomyopathy, comprising administering to a subject having cardiomyopathy an effective amount of a composition comprising an antibody that specifically binds a human IL-17 receptor of SEQ ID NO:4 and inhibits human IL-17 of SEQ ID NO:2 from binding said receptor.

2. The method of claim 1, wherein the composition further comprises a pharmaceutically acceptable diluent.

3. The method of claim 2, wherein the composition is administered by injection.

* * * * *